US011524073B2

United States Patent
Zheng et al.

(10) Patent No.: US 11,524,073 B2
(45) Date of Patent: Dec. 13, 2022

(54) ANTI-HUMAN ADRB3 MONOCLONAL ANTIBODY AND APPLICATION THEREOF IN DISEASE DIAGNOSIS AND TREATMENT

(71) Applicants: Meng Zheng, Guangdong (CN); Shuguang Lin, Guangdong (CN)

(72) Inventors: Meng Zheng, Guangdong (CN); Shuguang Lin, Guangdong (CN)

( * ) Notice: Subject to any disclaimer, the term of this patent is extended or adjusted under 35 U.S.C. 154(b) by 478 days.

(21) Appl. No.: 15/933,406

(22) Filed: Mar. 23, 2018

(65) Prior Publication Data

US 2018/0355037 A1 Dec. 13, 2018

(30) Foreign Application Priority Data

Mar. 24, 2017 (CN) .......................... 201710183354.8

(51) Int. Cl.
| | | |
|---|---|---|
| *C07K 16/28* | (2006.01) | |
| *A61K 39/395* | (2006.01) | |
| *C07K 14/705* | (2006.01) | |
| *G01N 33/74* | (2006.01) | |
| *A61P 25/36* | (2006.01) | |
| *A61P 3/10* | (2006.01) | |
| *A61P 37/00* | (2006.01) | |
| *A61P 35/00* | (2006.01) | |
| *G01N 33/94* | (2006.01) | |
| *A61P 15/10* | (2006.01) | |
| *A61P 31/12* | (2006.01) | |
| *A61P 25/18* | (2006.01) | |
| *G01N 33/569* | (2006.01) | |
| *C07K 14/725* | (2006.01) | |
| *G01N 33/574* | (2006.01) | |
| *G01N 33/577* | (2006.01) | |
| *G01N 33/68* | (2006.01) | |
| *A61K 39/00* | (2006.01) | |

(52) U.S. Cl.
CPC .............. *A61K 39/395* (2013.01); *A61P 3/10* (2018.01); *A61P 15/10* (2018.01); *A61P 25/18* (2018.01); *A61P 25/36* (2018.01); *A61P 31/12* (2018.01); *A61P 35/00* (2018.01); *A61P 37/00* (2018.01); *C07K 14/705* (2013.01); *C07K 14/7051* (2013.01); *C07K 14/70517* (2013.01); *C07K 14/70571* (2013.01); *C07K 14/70578* (2013.01); *C07K 16/286* (2013.01); *C07K 16/2869* (2013.01); *G01N 33/56966* (2013.01); *G01N 33/56972* (2013.01); *G01N 33/577* (2013.01); *G01N 33/57484* (2013.01); *G01N 33/6893* (2013.01); *G01N 33/6896* (2013.01); *G01N 33/74* (2013.01); *G01N 33/9433* (2013.01); *A61K 2039/505* (2013.01); *C07K 2317/24* (2013.01); *C07K 2317/622* (2013.01); *C07K 2317/73* (2013.01); *C07K 2319/00* (2013.01); *C07K 2319/03* (2013.01); *C07K 2319/33* (2013.01); *G01N 2333/70571* (2013.01); *G01N 2333/726* (2013.01)

(58) Field of Classification Search
None
See application file for complete search history.

(56) References Cited

U.S. PATENT DOCUMENTS

| | | | | |
|---|---|---|---|---|
| 9,622,996 | B2 * | 4/2017 | Lin | ..................... A61K 31/138 |
| 2002/0127639 | A1 * | 9/2002 | Emorine | .......... C07K 14/70571 |
| | | | | 435/69.1 |

OTHER PUBLICATIONS

Calvani et al. (2014) Oncotarget 6: 4615-4632.*

* cited by examiner

*Primary Examiner* — Michael D Pak
(74) *Attorney, Agent, or Firm* — JCIPRNET

(57) ABSTRACT

The present invention discloses an application of a β3 adrenergic receptor (ADRB3) as a marker for detecting a plurality of diseases, and an application of anti-human ADRB3 monoclonal antibody in diagnosing a disease and preparing a drug for treating the disease. The present invention finds through research that the ADRB3 is a key receptor in nerve-endocrine-immunoregulatory network, and an ADRB3-mediated signaling pathway regulates proliferation and differentiation of neutrophils, lymphocytes and tumor cells. Under normal circumstances, the ADRB3 maintains the non-specific immunocompetence and specific immunocompetence of an organism, and eliminates pathogenic microorganisms and aged organism tissues to play a role in protecting the organism and anti-aging. Under pathological conditions, excessive activation of the signaling pathway will cause systemic chronic inflammation, and destroy immune homeostasis. Therefore, the ADRB3 can be used as a diagnostic marker and a therapeutic target for a plurality of diseases. Anti-human ADRB3 antibody can specifically bond with the ADRB3, regulate the activity of the ADRB3, has the functions of resisting cancer, inflammation, poisoning, shock, allergy, viral infection, autoimmune disease, disease caused by regenerative dysfunction, autoimmune disease, cachexia, cardiovascular and cerebrovascular disease, neurodegenerative disease and aging, regulating autophagy, treating aging disease, etc., and has important medical value and research and application prospects.

2 Claims, 48 Drawing Sheets

Specification includes a Sequence Listing.

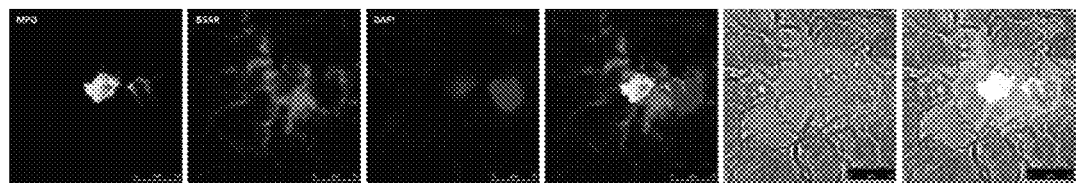
Fig. 32
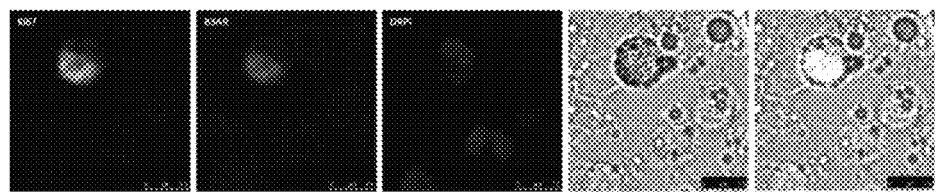
Fig. 33
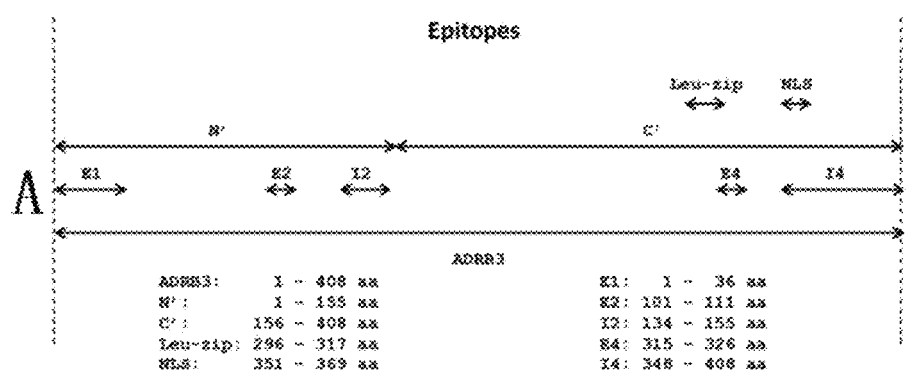
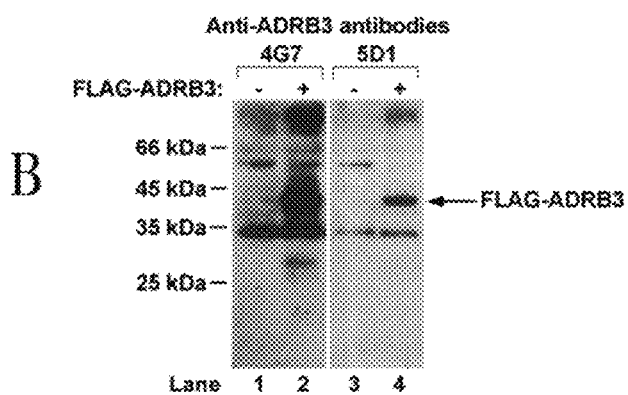
Fig. 34

The insert fragment Gene sequence information of pcDNA3-CNF-L:
Insert Size: 729 bp ATGGACTTCCAGTCCAGATTATCTCCTTCCTGCTGATTTCTGCCTCTGTGATAATGAGTAGGGAGACATCGTGATGACCAGGCCGCCCCTAGCGTGCCTGTGAC
CCCTGGGGAGAGCGTGAGCATCAGCTGAGGAGCAGCAAGAGCCTGCTGCACAGCAACACCTACCTGTACTGGTTCCTGAGAGGCCCCAGGCCCCAGTCCCC
CAGTGCCTGTATCACAGAATGTCCAATCTGGCCTCCGGATCGCTTTTCCGGTCCCAGATCGTTTACATTGAGGATCAGCAGCCTTACTGACAGCATCAAGCTGGAG
GCCGAGGATGTGGGCGTACTACTGTATGCAGCAGCGTGGAGTACCATTACATTGGAAACTGCCTCTGTGTGTCGCTGAATAACTTCTATCCAGGAGGCCAAAGTACAGTGGAA
TCTGTCTTCATCTTCCCGCCATCGGAAATCGGGATAACCTCCAATCGGGTAACTCACAGAGAGTGTCACAGAGGACAGGACAGCATCACAAGAGAGGTTCAACAGGGGAGAGTGTTAA
GGTGGATAACGCCCCTCCAATCGGGTAACTCACAGAGAGTGTCACAGAGGACAGGACAGCATCACAAGAGAGGTTCAACAGGGGAGAGTGTTAA
CAGAACTACGAGAAACACAAAGTTCACCGCTGCGAAGTCACCCATCAGGGGCCTGAAGCTGCCCCTCAACAAGAGAGGTTCAACAGGGGAGAGTGTTAA Expressed Protein Sequence of pcDNA3-CNF-L:
>CNF-L:
MDFQVQHSFLLISASVIMSREDIVMTQAAPSVPVTPGESVSISCRSSKSLLHSNGNTYLYWFLQRPGQSPQLLIYRMSNLASGVPDRFSGSGSGTAFTLRISRVEAEDVGVY
YCMQHLEYPFTFGTGTRKLEIKRRTVAAPSVFIFPPSDEQLKSGTASVVCLLNNFYPREAKVQWKVDNALQSGNSQESVTEQDSKDSTYSLSSTLTLSKADYEKHKVYACEVT
HQGLSSPVTKSFNRGEC

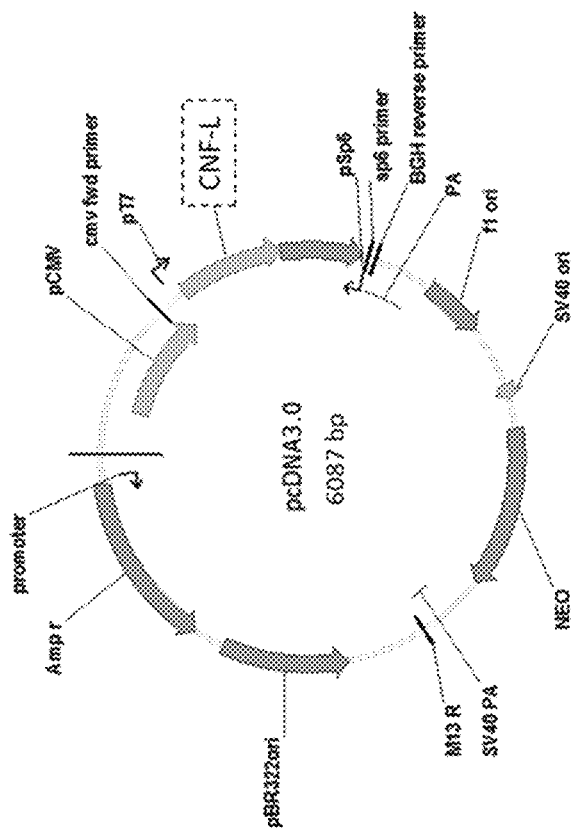

FIG. 35

The Insert fragment Gene sequence information of pcDNA3-CNF-H:
Insert Size: 1413 bp ATGGGCTGGTCCCTGATTCTGCTGTTCCTGGTGGCTGTGGCTACCAGGGTGCTGAGCGAGGTGCAGCTGCAGCAGTCCGGCAGCGAGCTGGTGAAGCCAGGCGC
CAGCGTGAAGATCTCCTGTAAGGCCTCCGGCTACTCCTTTACAGGCTACTACATGAATTGGGTGAAGCAGTCCCCTGAGAAGTCCCTGGAGTGGATCGGCGAGAT
CAATCCCTCCACCGGCGGCACCTACAACCAGAAGTTCAAGGCCAAGGCCACCCTGACCGTGGACAAGAGCAGCAGCACCGCCTACATGCAGCTGAAGAGCCT
GACAAGCGAGGACGCCGTGTACTACTGCGCCCGGGTGCTGTACGATTACGAGGGCTCCGGCTTTGCCTACTGGGGCCAGGGCACACTGGTGACAGTGTCCG
CCGCTAGCACCAAGGGCCCATCGGTCTTCCCCCTGGCACCCTCCTCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACC
GTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAA
ACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGA
GGTCACGTGCGTGGTGGTGGACGTGAGCCACGAAGACCCTGAGGTCAAGTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGC
CCTCCCAGCCCCCATCGAGAAAACCATCTCCAAAGCCAAAGGGCAGCCCCGAGAACCACAGGTGTACACCCTGCCCCCATCCCGGGATGAGCTGACCAAGAACCA
GGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCT
GCACAACCACTACACGCAGAAGAGCCTCTCCCTGTCTCCGGGTAAATAA

Expressed Protein Sequence of pcDNA3-CNF-H:
>CNF-H
MGWSLILFLVAVATRVLSEVQLQQSGSELVKPGASVKISCKASGYSFTGYYMNWVKQSPEKSLEWIGEINPSTGGTYYNQKFKAKATLTVDKSSSTAYMQLKSLTSEDSA
VYYCARVLYDYEGSGFAYWGQGTLVTVSAASTKGPSVFPLAPSSKSTSGGTAALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQG
NVFSCSVMHEALHNHYTQKSLSLSPGK

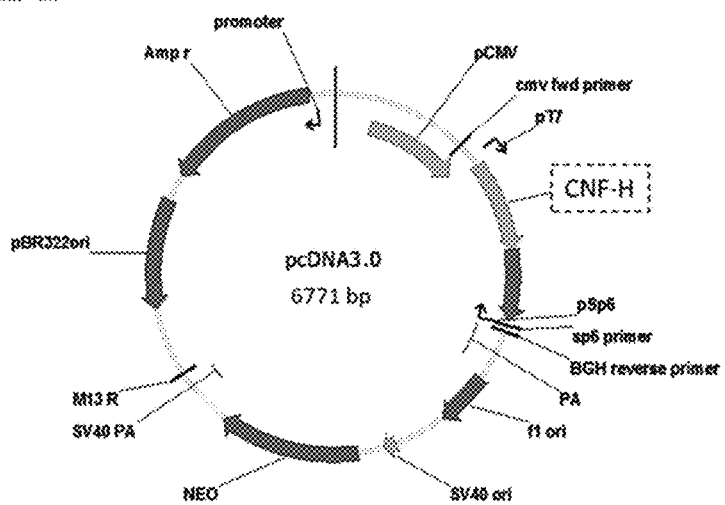

FIG. 36

SEQUENCE LISTING

<160> NUMBER OF SEQ ID NOS: 26

<210> SEQ ID NO 1
<211> LENGTH: 8

```
<212> TYPE: PRT
<213> ORGANISM: Artificial Sequence
<220> FEATURE:
<223> OTHER INFORMATION: Heavy chain complementarity determining region

<400> SEQUENCE: 1

Gly Phe Thr Phe Ser Ser Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Heavy chain complementarity determining region

<400> SEQUENCE: 2

Ile Ser Pro Gly Gly Ser Tyr Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Heavy chain complementarity determining region

<400> SEQUENCE: 3

Ala Arg Arg Asp Leu Asp Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: Heavy chain complementarity determining region

<400> SEQUENCE: 4

Gly Tyr Thr Phe Thr Ser Tyr Trp
1               5

<210> SEQ ID NO 5
<211> LENGTH: 8
<212> TYPE: PRT
<213> ORGANISM: Artificial Sequence
<220> FEATURE:
<223> OTHER INFORMATION: Heavy chain complementarity determining region

<400> SEQUENCE: 5

Ile Tyr Pro Gly Asn Ser Asp Thr
1               5

<210> SEQ ID NO 6
<211> LENGTH: 13
<212> TYPE: PRT
<213> ORGANISM: Artificial Sequence
<220> FEATURE:
<223> OTHER INFORMATION: Heavy chain complementarity determining region

<400> SEQUENCE: 6

Thr Arg Glu Asp Tyr Asp Tyr Asp Trp Tyr Phe Asp Val
1               5                   10

<210> SEQ ID NO 7
<211> LENGTH: 8
<212> TYPE: PRT
```

```
<213> ORGANISM: Artificial Sequence
<220> FEATURE:
<223> OTHER INFORMATION: Heavy chain complementarity determining region

<400> SEQUENCE: 7

Gly Tyr Ser Phe Thr Gly Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Heavy chain complementarity determining region

<400> SEQUENCE: 8

Ile Asn Pro Ser Thr Gly Gly Thr
1               5

<210> SEQ ID NO 9
<211> LENGTH: 14
<212> TYPE: PRT
<213> ORGANISM: Artificial Sequence
<220> FEATURE:
<223> OTHER INFORMATION: Heavy chain complementarity determining region

<400> SEQUENCE: 9

Ala Arg Val Leu Tyr Asp Tyr Glu Gly Ser Gly Phe Ala Tyr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Heavy chain complementarity determining region

<400> SEQUENCE: 10

Gly Tyr Ser Phe Thr Gly Tyr Thr
1               5

<210> SEQ ID NO 11
<211> LENGTH: 8
<212> TYPE: PRT
<213> ORGANISM: Artificial Sequence
<220> FEATURE:
<223> OTHER INFORMATION: Heavy chain complementarity determining region

<400> SEQUENCE: 11

Ile Asn Pro Ser Thr Gly Asp Thr
1               5

<210> SEQ ID NO 12
<211> LENGTH: 14
<212> TYPE: PRT
<213> ORGANISM: Artificial Sequence
<220> FEATURE:
<223> OTHER INFORMATION: Heavy chain complementarity determining region

<400> SEQUENCE: 12

Ala Arg Val Leu Tyr Asp Tyr Glu Gly Pro Gly Phe Ala Tyr
1               5                   10

<210> SEQ ID NO 13
<211> LENGTH: 11
<212> TYPE: PRT
<213> ORGANISM: Artificial Sequence
```

```
<220> FEATURE:
<223> OTHER INFORMATION: Heavy chain complementarity determining region

<400> SEQUENCE: 13

Gln Ser Leu Leu Tyr Ser Asp Gly Lys Thr Tyr
1               5                   10

<210> SEQ ID NO 14
<211> LENGTH: 3
<212> TYPE: PRT
<213> ORGANISM: Artificial Sequence
<220> FEATURE:
<223> OTHER INFORMATION: Heavy chain complementarity determining region

<400> SEQUENCE: 14

Gln Val Ser
1

<210> SEQ ID NO 15
<211> LENGTH: 9
<212> TYPE: PRT
<213> ORGANISM: Artificial Sequence
<220> FEATURE:
<223> OTHER INFORMATION: Heavy chain complementarity determining region

<400> SEQUENCE: 15

Leu Gln Gly Thr Tyr Phe Pro His Thr
1               5

<210> SEQ ID NO 16
<211> LENGTH: 10
<212> TYPE: PRT
<213> ORGANISM: Artificial Sequence
<220> FEATURE:
<223> OTHER INFORMATION: Heavy chain complementarity determining region

<400> SEQUENCE: 16

Glu Ser Val Glu Tyr Tyr Gly Thr Ser Leu
1               5                   10

<210> SEQ ID NO 17
<211> LENGTH: 3
<212> TYPE: PRT
<213> ORGANISM: Artificial Sequence
<220> FEATURE:
<223> OTHER INFORMATION: Heavy chain complementarity determining region

<400> SEQUENCE: 17

Gly Ala Ser
1

<210> SEQ ID NO 18
<211> LENGTH: 8
<212> TYPE: PRT
<213> ORGANISM: Artificial Sequence
<220> FEATURE:
<223> OTHER INFORMATION: Heavy chain complementarity determining region

<400> SEQUENCE: 18

Gln Gln Ser Arg Lys Val Arg Thr
1               5

<210> SEQ ID NO 19
<211> LENGTH: 11
<212> TYPE: PRT
<213> ORGANISM: Artificial Sequence
<220> FEATURE:
```

```
<223> OTHER INFORMATION: Heavy chain complementarity determining region

<400> SEQUENCE: 19

Lys Ser Leu Leu His Ser Asn Gly Asn Thr Tyr
1               5                   10

<210> SEQ ID NO 20
<211> LENGTH: 3
<212> TYPE: PRT
<213> ORGANISM: Artificial Sequence
<220> FEATURE:
<223> OTHER INFORMATION: Heavy chain complementarity determining region

<400> SEQUENCE: 20

Arg Met Ser
1

<210> SEQ ID NO 21
<211> LENGTH: 9
<212> TYPE: PRT
<213> ORGANISM: Artificial Sequence
<220> FEATURE:
<223> OTHER INFORMATION: Heavy chain complementarity determining region

<400> SEQUENCE: 21

Met Gln His Leu Glu Tyr Pro Phe Thr
1               5

<210> SEQ ID NO 22
<211> LENGTH: 13
<212> TYPE: PRT
<213> ORGANISM: Artificial Sequence
<220> FEATURE:
<223> OTHER INFORMATION: Heavy chain complementarity determining region

<400> SEQUENCE: 22

Lys Ser Leu Leu Tyr His Ser Asn Gly Leu Asn Thr Tyr
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Heavy chain complementarity determining region

<400> SEQUENCE: 23

Arg Ala Ser Thr
1

<210> SEQ ID NO 24
<211> LENGTH: 10
<212> TYPE: PRT
<213> ORGANISM: Artificial Sequence
<220> FEATURE:
<223> OTHER INFORMATION: Heavy chain complementarity determining region

<400> SEQUENCE: 24

Met Gln His Leu Glu Tyr Pro Phe Ala Thr
1               5                   10

<210> SEQ ID NO 25
<211> LENGTH: 96
<212> TYPE: PRT
<213> ORGANISM: Artificial Sequence
<220> FEATURE:
<223> OTHER INFORMATION: A heavy chain V region of a humanized antibody
```

<400> SEQUENCE: 25

```
Glu Val Gln Leu Gln Gln Ser Gly Ser Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met Asn Trp Val Lys Gln Ser Pro Glu Lys Ser Leu Glu Trp Ile
        35                  40                  45

Gly Glu Ile Asn Pro Ser Thr Gly Gly Thr Thr Tyr Asn Gln Lys Phe
    50                  55                  60

Lys Ala Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95
```

<210> SEQ ID NO 26
<211> LENGTH: 98
<212> TYPE: PRT
<213> ORGANISM: Artificial Sequence
<220> FEATURE:
<223> OTHER INFORMATION: A heavy chain V region of a humanized antibody

<400> SEQUENCE: 26

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu
```

ANTI-HUMAN ADRB3 MONOCLONAL ANTIBODY AND APPLICATION THEREOF IN DISEASE DIAGNOSIS AND TREATMENT

CROSS-REFERENCE TO RELATED APPLICATION

This application claims the priority benefit of China application serial no. 201710183354.8, filed on Mar. 24, 2017. The entirety of the above-mentioned patent application is hereby incorporated by reference herein and made a part of this specification.

TECHNICAL FIELD

The present invention belongs to the field of biopharmaceutical technology, specifically relates to the technology of immunomodulation signaling pathway, and more specifically relates to a new application of anti-human ADRB3 monoclonal antibody in preparing a drug against cancer, inflammation, poisoning, allergy, viral infection, autoimmune disease, cachexia, shock, atherosclerosis, bone joint degeneration, neurodegeneration or aging.

BACKGROUND ART

As a G protein-coupled receptor, human β3 adrenoceptor (adrenoceptor Beta3, ADRB3, B3AR, beta3 adrenoceptor and β3 receptor) is one of tissue receptors that mediate the function of catecholamine. At present, the research on ADRB3 is mainly focused on the effect on body fat, blood glucose and lipid level, insulin secretion and function.

There are no relevant researches or reports on the effect of ADRB3 in the field of disease, such as malignant tumor, atherosclerosis, Alzheimer disease, inflammation, pyohemia, multiple organ dysfunction syndrome, viral infection, autoimmune disease, organ transplantation immunity rejection, aging, osteoporosis, severe trauma, poisoning and cachexia.

SUMMARY

An object of the present invention is to provide an application of a human ADRB3 and its monoclonal antibody in treating a disease, such as tumor (malignant tumor), inflammation (chronic systemic inflammation of an organism), pyohemia, asthma, diabetes, multiple organ dysfunction syndrome, viral infection, aging disease, anemia, severe trauma, allergic disease, cachexia, poisoning, autoimmune disease, organ transplantation immunity rejection, pulmonary hypertension, atherosclerosis, neurodegenerative disease, osteoporosis or other degenerative bone diseases, hypertrophic cardiomyopathy or Alzheimer disease.

The object of the invention is implemented by disclosing the following technical solutions:

The present invention finds through a lot of researches and exploratory experiments that the ADRB3 is a key receptor in nerve-endocrine-immunoregulatory network, and an ADRB3-mediated signaling pathway regulates proliferation and differentiation of neutrophils, lymphocytes and tumor cells. Under normal circumstances, the ADRB3 maintains the non-specific immunocompetence and specific immunocompetence of an organism, and eliminates exogenous pathogenic microorganisms and aged organism tissues to play a role in protecting the organism and anti-aging. Under pathological conditions, excessive activation of the signaling pathway will cause systemic chronic inflammation, and destroy immune homeostasis. Based on this common mechanism, the ADRB3 is associated with a plurality of diseases. A monoclonal antibody for the ADRB3 can specifically bind to the ADRB3, regulate (block or excite) its activity, and be used to treat inflammation, viral infection, atherosclerosis, diabetes, neurodegeneration, autoimmune disease, lalignant tumor, aging disease and the like. That is, in essence, the treatment mechanisms of these diseases are all associated with the ADRB3, and the disease prevention, control and treatment are realized by inhibiting or activating the ADRB3.

Therefore, the present invention discloses the following applications of an ADRB3 and an anti-ADRB3 monoclonal antibody:

an application of an ADRB3 in regulating human immune functions.

The immune dysfunction caused by an ADRB3 is a common pathological mechanism of autoimmune disease, tumor, inflammation, viral or pathogen infection, atherosclerosis, diabetes, Alzheimer disease, Parkinson's disease, aging, chronic fatigue syndrome, cachexia, pulmonary hypertension, hypertension, thrombotic disease, schizophrenia, depression, addictive disease, stress disorder, organ transplantation immunity rejection, tissue degeneration, fibrous degeneration disease, organ dysfunction, reproductive and sexual dysfunction and regenerative dysfunction.

An application of an ADRB3 as a target site of a drug for regulating human immune functions.

An application of an ADRB3 as a biomarker for detecting cells at G0 phase, tumor cells, human myeloid-derived suppressor cells, lymphocytes, regulatory T cells, dendritic cells, natural killer cells, neutrophils, monocytes-macrophages, hematopoietic stem cells, megakaryocytes, lymphocyte progenitor cells, myeloid progenitor cells, myeloid cells, platelets, osteoclasts or microglial cells. Especially an application as a marker for detecting myeloblasts, promyelocytes, myelocytes, neutrophils, eosinophils, myeloid-derived suppressor cells, tumor-associated macrophages, mastocytes, dendritic cells, regulatory T cells, abnormal lymphocytes, T cells, B cells, natural killer cells (NK cells), antigen presenting cells, plasmocytes, primitive lymphocytes or naive lymphocytes.

An application of an ADRB3 as a biomarker for evaluating malignancy degree of tumor cells, metastasis prognosis and/or curative effect monitoring, a marker for evaluating cell proliferation and/or cell differentiation ability, and a marker for evaluating specific immunocompetence and/or aging degree.

An application of an ADRB3 as a diagnostic and/or therapeutic target of tumor, inflammation, pyohemia, asthma, diabetes, multiple organ dysfunction syndrome, viral infection, aging disease, allergic disease, cachexia, poisoning disease, autoimmune disease, organ transplantation immunity rejection, pulmonary hypertension, acute coronary syndrome, bone joint degeneration or neurodegenerative disease.

An application of an ADRB3 as a marker for evaluating specific immunocompetence.

An application of the ADRB3 as a cosupression signal molecule of T-lymphocytes.

An application of a soluble ADRB3 in regulating immune functions of an organism.

An application of an anti-human ADRB3 monoclonal antibody in detecting and regulating a body fluid-soluble ADRB3.

An application of an anti-human ADRB3 monoclonal antibody in detecting and regulating the content of an ADRB3 protein in a cell or tissue.

An application of an anti-human ADRB3 monoclonal antibody in immunological experiments, such as Western blot, fluorescence in situ hybridization technique, immunoprecipitation, immunohistochemical analysis, enzyme-linked immunosorbent assay (ELISA), immunofluorescence, magnetic bead separation, immune colloidal gold test or flow cytometry, and in detecting an ADRB3 protein in human serum, histocytes, human secreta or cell cultures.

An application of an anti-human ADRB3 monoclonal antibody in regulating the functions of an ADRB3.

An application of an anti-human ADRB3 monoclonal antibody in regulating the functions of a chemotactic factor, an immunosuppressive receptor and/or a neural cell adhesion molecule.

An application of an anti-human ADRB3 monoclonal antibody in diagnosing and/or treating an immune-related disease.

An application of an anti-human ADRB3 monoclonal antibody in preparing an immune checkpoint inhibitor.

An application of an anti-human ADRB3 monoclonal antibody in preparing a drug for regulating the cosuppression function of T-lymphocytes.

An application of an anti-human ADRB3 monoclonal antibody in regulating congenital immune functions.

An application of an anti-human ADRB3 monoclonal antibody in regulating the functions of a complement.

An application of an anti-human ADRB3 monoclonal antibody in regulating immune tolerance functions.

An application of an anti-human ADRB3 monoclonal antibody in regulating antigen presentation functions.

An application of an anti-human ADRB3 monoclonal antibody as an immune adjuvant in regulating vaccine functions.

An application of an anti-human ADRB3 monoclonal antibody in diagnosing and/or treating a malignant tumor.

An application of an anti-human ADRB3 monoclonal antibody in preparing an anticancer or antitumor drug or vaccine.

An application of an anti-human ADRB3 monoclonal antibody in diagnosing and/or treating breast cancer, lung cancer, pancreatic cancer, liver cancer, cerebral glioma, colon cancer, rectal cancer, kidney cancer, bladder cancer, gastric cancer, esophageal cancer, melanoma, lymphoma, prostate cancer, ovarian cancer, endometrial cancer, cholangiocarcinoma, osteosarcoma, thyroid cancer or leukemia. In specific diagnosis, an ADRB3 antibody can be used to detect the soluble ADRB3 in body fluids, such as blood, cerebrospinal fluid, hydrothorax and ascites to realize disease diagnosis.

An application of an anti-human ADRB3 monoclonal antibody in preparing a drug against tumor metastasis.

An application of an anti-human ADRB3 monoclonal antibody in preparing a multidrug resistance reversal agent.

An application of an anti-human ADRB3 monoclonal antibody in evaluating prognosis of a patient with a malignant tumor and/or monitoring the curative effect.

An application of an anti-human ADRB3 monoclonal antibody in diagnosing and/or treating cachexia.

An application of an anti-human ADRB3 monoclonal antibody in diagnosing and/or treating an inflammatory disease.

An application of an anti-human ADRB3 monoclonal antibody in preparing an anti-inflammatory drug.

An application of an anti-human ADRB3 monoclonal antibody in diagnosing and/or treating a disease caused by infection of pathogen, such as bacterium, virus, fungi, *mycoplasma, chlamydia*, prion, or the like.

An application of an anti-human ADRB3 monoclonal antibody in diagnosing and/or treating gonococcus infectious disease.

An application of an anti-human ADRB3 monoclonal antibody in diagnosing and/or treating virus infectious disease.

An application of an anti-human ADRB3 monoclonal antibody in diagnosing and/or treating respiratory virus infectious disease.

An application of an anti-human ADRB3 monoclonal antibody in diagnosing and/or treating hepatitis B virus infectious disease.

An application of an anti-human ADRB3 monoclonal antibody in diagnosing and/or treating Aids.

An application of an anti-human ADRB3 monoclonal antibody in preparing an anti-viral vaccine.

An application of an anti-human ADRB3 monoclonal antibody in diagnosing and/or treating nephritis, hepatitis, pneumonia, myocarditis or cerebritis.

An application of an anti-human ADRB3 monoclonal antibody in diagnosing and/or treating endotoxemia.

An application of an anti-human ADRB3 monoclonal antibody in diagnosing and/or treating infectious shock.

An application of an anti-human ADRB3 monoclonal antibody in diagnosing and/or treating pyohemia.

An application of an anti-human ADRB3 monoclonal antibody in diagnosing and/or treating multiple organ dysfunction syndrome.

An application of an anti-human ADRB3 monoclonal antibody in diagnosing and/or treating an autoimmune disease.

An application of an anti-human ADRB3 monoclonal antibody in preparing a drug for treating an autoimmune disease.

An application of an anti-human ADRB3 monoclonal antibody in diagnosing and/or treating systemic lupus erythematosus.

An application of an anti-human ADRB3 monoclonal antibody in diagnosing and/or treating rheumatoid arthritis.

An application of an anti-human ADRB3 monoclonal antibody in diagnosing and/or treating chronic ulcerative colitis.

An application of an anti-human ADRB3 monoclonal antibody in diagnosing and/or treating psoriasis.

An application of an anti-human ADRB3 monoclonal antibody in diagnosing and/or treating sjogren syndrome.

An application of an anti-human ADRB3 monoclonal antibody in diagnosing and/or treating multiple sclerosis.

An application of an anti-human ADRB3 monoclonal antibody in diagnosing and/or treating diabetes.

An application of an anti-human ADRB3 monoclonal antibody in diagnosing and/or treating a poisoning disease.

An application of an anti-human ADRB3 monoclonal antibody in diagnosing and/or treating neurodegenerative disease.

An application of an anti-human ADRB3 monoclonal antibody in diagnosing and/or treating Alzheimer disease or Parkinson's disease.

An application of an anti-human ADRB3 monoclonal antibody in preparing a drug for improving memory.

An application of an anti-human ADRB3 monoclonal antibody in diagnosing and/or treating a mental disease.

An application of an anti-human ADRB3 monoclonal antibody in diagnosing and/or treating schizophrenia.

An application of an anti-human ADRB3 monoclonal antibody in preparing an anti-depressant drug.

An application of an anti-human ADRB3 monoclonal antibody in preparing a drug against stress disorder.

An application of an anti-human ADRB3 monoclonal antibody in diagnosing and/or treating an addictive disease.

An application of an anti-human ADRB3 monoclonal antibody in preparing a drug against alcohol or drug addiction.

An application of an anti-human ADRB3 monoclonal antibody in preparing a drug against amphetamine or heroin addiction.

An application of an anti-human ADRB3 monoclonal antibody in diagnosing and/or treating cardiovascular and cerebrovascular disease.

An application of an anti-human ADRB3 monoclonal antibody in preparing a drug against atheroscerosis.

An application of an anti-human ADRB3 monoclonal antibody in preparing an anti-platelet or antithrombotic drug.

An application of an anti-human ADRB3 monoclonal antibody in preparing a drug for treating a thromboembolistic disease.

An application of an anti-human ADRB3 monoclonal antibody in preparing a drug for treating cerebral, hepatic, pulmonary, intestinal, renal, myocardial ischemia or reperfusion injury.

An application of an anti-human ADRB3 monoclonal antibody in preparing a drug for treating cerebral stroke.

An application of an anti-human ADRB3 monoclonal antibody in preparing a drug for treating pulmonary embolism.

An application of an anti-human ADRB3 monoclonal antibody in preparing a drug against neutrophils.

An application of an anti-human ADRB3 monoclonal antibody in diagnosing and/or treating acute coronary syndrome.

An application of an anti-human ADRB3 monoclonal antibody in diagnosing and/or treating heart failure.

An application of an anti-human ADRB3 monoclonal antibody in diagnosing and/or treating hypertension.

An application of an anti-human ADRB3 monoclonal antibody in regulating blood lipids.

An application of an anti-human ADRB3 monoclonal antibody in diagnosing and/or treating pulmonary hypertension.

An application of an anti-human ADRB3 monoclonal antibody in regulating a drug eluting stent or a drug eluting balloon.

An application of an anti-human ADRB3 monoclonal antibody in diagnosing and/or treating an aging disease.

An application of an anti-human ADRB3 monoclonal antibody in preparing an anti-aging drug.

An application of an anti-human ADRB3 monoclonal antibody as or in preparing a drug for treating the above diseases, an anti-granulocyte drug, a chemosensitizer, a hemostatic drug, a complement antagonist, an immune adjuvant, a bispecific antibody, a differentiation inducer, a deacetylase inhibitor or an elastase inhibitor.

An application of an anti-human ADRB3 monoclonal antibody in preparing a cosmetic for skin care or against skin aging or for facial beauty. Having an effect of delaying skin aging, restoring skin elasticity, reducing wrinkles, or reducing pigmentation.

An application of an anti-human ADRB3 monoclonal antibody in antifatigue or sleep improvement and preparing a drug or preparation for antifatigue or sleep improvement.

An application of an anti-human ADRB3 monoclonal antibody in preparing a drug against chronic fatigue syndrome.

An application of an anti-human ADRB3 monoclonal antibody in preparing a drug for promoting regeneration capacity of a human tissue.

An application of an anti-human ADRB3 monoclonal antibody in preparing a drug for promoting liver regeneration capacity.

An application of an anti-human ADRB3 monoclonal antibody in preparing a drug for promoting regeneration of a tissue, such as myocardium, liver, marrow, pancreas, cerebrum, nerve, kidney, lung or muscle.

An application of an anti-human ADRB3 monoclonal antibody in treating a disease, such as leukopenia, neutropenia, lymphocytopenia, aplastic anemia, age related muscular dystrophy or age related macular degeneration.

An application of an anti-human ADRB3 monoclonal antibody in diagnosing and/or treating a fibrous degeneration disease.

An application of an anti-human ADRB3 monoclonal antibody in diagnosing and/or treating pulmonary fibrosis or silicosis.

An application of an anti-human ADRB3 monoclonal antibody in preventing and/or treating organ transplantation immunity rejection.

An application of an anti-human ADRB3 monoclonal antibody in preparing an organ transplantation immunity inhibitor.

An application of an anti-human ADRB3 monoclonal antibody in diagnosing and/or treating degenerative osteoarthropathy.

An application of an anti-human ADRB3 monoclonal antibody in diagnosing and/or treating osteoporosis.

An application of an anti-human ADRB3 monoclonal antibody in diagnosing and/or treating an allergic disease.

An application of an anti-human ADRB3 monoclonal antibody in preparing an antiallergic drug.

An application of an anti-human ADRB3 monoclonal antibody in diagnosing and/or treating asthma.

An application of an anti-human ADRB3 monoclonal antibody in diagnosing and/or treating reproductive or sexual dysfunction.

An application of an anti-human ADRB3 monoclonal antibody in treating infertility.

An application of an anti-human ADRB3 monoclonal antibody in treating sterility.

An application of an anti-human ADRB3 monoclonal antibody in preparing chimeric antigen receptor-modified T-cells.

An application of an anti-ADRB3 chimeric antigen receptor-modified T-lymphocyte in treating a malignant tumor.

An application of an anti-ADRB3 chimeric antigen receptor-modified T-lymphocyte in treating an autoimmune disease or preparing a drug for treating the autoimmune disease.

An application of an anti-ADRB3 chimeric antigen receptor-modified T-lymphocyte in treating an inflammatory disease or preparing a drug for treating the inflammatory disease.

An application of an anti-ADRB3 chimeric antigen receptor-modified T-lymphocyte in treating atherosclerosis or preparing a drug for treating atherosclerosis.

An application of an anti-ADRB3 chimeric antigen receptor-modified T-lymphocyte in treating a virus infectious disease or preparing a drug for treating the virus infectious disease.

An application of an anti-ADRB3 chimeric antigen receptor-modified T-lymphocyte in treating a neurodegenerative disease or preparing a drug for treating the neurodegenerative disease.

An application of an anti-ADRB3 chimeric antigen receptor-modified T-lymphocyte in antiaging or preparing an antiaging drug.

An application of an anti-ADRB3 chimeric antigen receptor-modified macrophagocyte, dendritic cell or natural killer cell in treating a malignant tumor, an autoimmune disease, atherosclerosis, inflammation, viral infection, a neurodegenerative disease or an aging disease or in preparing a drug for treating the same.

An application of an anti-human ADRB3 monoclonal antibody in regulating proliferation and differentiation of tumor cells, neutrophils, monocytes-macrophages, myeloid-derived suppressor cells, regulatory T cells, dendritic cells, natural killer cells, platelets or lymphocytes.

An application of an anti-human ADRB3 monoclonal antibody in regulating the functions of a dendritic cell.

An application of an anti-human ADRB3 monoclonal antibody in regulating the functions of a B-lymphocyte.

An application of an anti-human ADRB3 monoclonal antibody in regulating the functions of a natural killer cell.

An application of an anti-human ADRB3 monoclonal antibody in regulating the functions of a mononuclear phagocyte.

An application of an anti-human ADRB3 monoclonal antibody in regulating the functions of an erythrocyte.

An application of an anti-human ADRB3 monoclonal antibody in regulating the functions of a neurogliocyte.

An application of an anti-human ADRB3 monoclonal antibody in regulating the functions of a hematopoietic stem cell.

An application of an anti-human ADRB3 monoclonal antibody in regulating mitochondrial functions.

An application of an anti-human ADRB3 monoclonal antibody in regulating ribosomal functions.

An application of an anti-human ADRB3 monoclonal antibody in regulating nucleolar functions.

An application of an anti-human ADRB3 monoclonal antibody in regulating lysosomal functions.

An application of an anti-human ADRB3 monoclonal antibody in regulating cytoskeleton and cell migration ability.

An application of an anti-human ADRB3 monoclonal antibody in regulating microtubule functions.

An application of an anti-human ADRB3 monoclonal antibody in regulating cell adhesion ability.

An application of an anti-human ADRB3 monoclonal antibody in regulating an epigenetic modification.

An application of an anti-human ADRB3 monoclonal antibody in regulating amino acid acetylation.

An application of an anti-human ADRB3 monoclonal antibody in regulating autophagy function.

An application of an anti-human ADRB3 monoclonal antibody in regulating cell glycolysis.

An application of an anti-human ADRB3 monoclonal antibody in regulating the functions of a cell at G0 phase.

An application of an anti-human ADRB3 monoclonal antibody in identifying and selecting a cell at G0 phase.

An application of an anti-human ADRB3 monoclonal antibody in regulating cell cycle. Including regulating the cell cycle and mitotic function of tumor cells, stem cells, granulocytes, monocytes-macrophages and lymphocytes.

An application of an anti-human ADRB3 monoclonal antibody in regulating mitosis.

An application of an anti-human ADRB3 monoclonal antibody in regulating cell differentiation and proliferation functions.

An application of an anti-human ADRB3 monoclonal antibody in regulating cell apoptosis.

An application of an anti-human ADRB3 monoclonal antibody in preparing a drug eluting stent or a drug eluting balloon as a drug coating.

An application of an ADRB3 antibody with ADRB3 activity, an ADRB3 agonist or a human ADRB3 protein produced using a gene recombination technology in preparing a hemameba growth promoter.

An application of an ADRB3 protein or polypeptide in preparing a drug for promoting myeloid hematopoiesis.

The present invention further discloses an ADRB3 epitope associated with an anti-ADRB3 antibody, including but not limited to the following antigenic epitopes: S212, S239, S349, C110, C189, T65, T140, S191, Y336, Y346, K151, R152, C153, P343, P350, P368, P369, P371, P377, P381, P391, P394, H190, H288, N8, N26, T150, T108, T114, G41, G106, G146, G271, G295, G383, G402, C275, C363, Y145, Y204, Y214, Y236 and Y346. An antibody according to the present invention binds to, but is not limited to, the above epitopes to play a role in regulating ADRB3 functions. (S: serine, C: cysteine, T: threonine, Y: tyrosine, K: lysine, R: arginine, C: cysteine, P: proline, H: histidine, N: asparagine).

The present invention discloses a polypeptide fragment required to prepare an anti-ADRB3 antibody, including but not limited to the following polypeptides:

a human ADRB3 full length protein (1 st-408th amino acid residues), a fragment of 1st-155th N-terminal amino acid residues in an ADRB3 protein, a fragment of 156th-408th C-terminal amino acid residues in an ADRB3 protein, a leucine zipper fragment of 296th-317th amino acid residues in an ADRB3 protein, a nuclear localization sequence (NLS) of 351st-369th amino acid residues in an ADRB3 protein, an E1 fragment of 1st-36th amino acid residues in an ADRB3 protein, an E2 fragment of 101st-111th amino acid residues in an ADRB3 protein, an I2 fragment of 134th-155th amino acid residues in an ADRB3 protein, an E4 fragment of 315th-326th amino acid residues in an ADRB3 protein, an I4 fragment of 348th-408th amino acid residues in an ADRB3 protein, a fragment of 344th-349th amino acid residues, an ITIM1 fragment of 143th-148th amino acid residues, an ITIM1 fragment of 140th-146th amino acid residues, an ITIM2 fragment of 202nd-207th amino acid residues, an ITIM2 fragment of 199th-204th amino acid residues and an ITIM3 fragment of 212th-217th amino acid residues.

The present invention further relates to an anti-human ADRB3 monoclonal antibody selected from:

(1) a monoclonal antibody produced from hybridoma cell line 5D1 deposited with the China Center for Type Culture Collection (CCTCC) under accession number CCTCC No: C2015146 on Sep. 3, 2015;

(2) a monoclonal antibody produced from hybridoma cell line 5B8 deposited with the China Center for Type Culture Collection (CCTCC) under accession number C2016202 on Dec. 12, 2016;

(3) a monoclonal antibody produced from hybridoma cell line 4G7 deposited with the China Center for Type Culture Collection (CCTCC) under accession number CCTCC No: C2015147 on Sep. 3, 2015;

(4) a monoclonal antibody produced from hybridoma cell line 5D9 deposited with the China Center for Type Culture Collection (CCTCC) under accession number C2016203 on Dec. 12, 2016;

(5) a monoclonal antibody having a binding specificity of a monoclonal antibody produced from hybridoma cell line 5D1, 5B8, 4G7 or 5D9;

(6) a monoclonal antibody bound to epitopes capable of binding to a monoclonal antibody produced from hybridoma cell line 5D1, 5B8, 4G7 or 5D9;

(7) a monoclonal antibody competing with a monoclonal antibody produced from hybridoma cell line 5D1, 5B8, 4G7 or 5D9 in a competitive binding test;

(8) a rabbit monoclonal antibody, a rat-derived antibody, a chimeric antibody, a fully human antibody, a single domain antibody, a single chain antibody, a Fab antibody fragment and a synthetic antibody capable of specifically binding to an ADRB3;

(9) an anti-ADRB3 antibody binding to a number of the following antigenic epitopes of the ADRB3 to regulate the activity of an ADRB3 protein: S212, S239, S349, C110, C189, T65, T140, S191, Y336, Y346, K151, R152, C153, P343, P350, P368, P369, P371, P377, P381, P391, P394, H190, H288, N8, N26, T150, T108, T114, G41, G106, G146, G271, G295, G383, G402, C275, C363, Y145, Y145, Y204, Y214, Y236 and Y346; including but not limited to the above epitopes; where S is serine, C is cysteine, T is threonine, Y is tyrosine, K is lysine, R is arginine, C is cysteine, P is proline, H is histidine, and N is asparaginate; and

(10) an antibody specifically binding to an ADRB3, comprising:

(a) a heavy chain complementarity determining region (CDR) comprising:

i) a first complementarity determining region containing an amino acid sequence having at least 70% sequence identity to SEQ ID NO: 1, 4, 7 and 10;

ii) a second complementarity determining region containing an amino acid sequence having at least 80% sequence identity to SEQ ID NO: 2, 5, 8 and 11; and iii) a third complementarity determining region containing an amino acid sequence having at least 80% sequence identity to SEQ ID NO: 3, 6, 9 and 12; and (b) a light chain complementarity determining region comprising:

i) a first complementarity determining region containing an amino acid sequence having at least 80% sequence identity to SEQ ID NO: 13, 16, 19 and 22;

ii) a second complementarity determining region containing an amino acid sequence having at least 80% sequence identity to SEQ ID NO: 14, 17, 20 and 23; and iii) a third complementarity determining region containing an amino acid sequence having at least 80% sequence identity to SEQ ID NO: 15, 18, 21 and 24;

(c) a heavy chain variable region (V region) of a humanized antibody containing an amino acid sequence having at least 70% sequence identity to SEQ ID NO: 25; and/or (d) a light chain complementarity determining region of a humanized antibody containing an amino acid sequence having at least 70% sequence identity to SEQ ID NO: 26.

As accepted by those skilled in the art, a CDR disclosed herein may include a variant of the CDR, and is reversely mutated to a different frame area. Usually, an individual variant of the CDR has at least 70% or 80% identity to the amino acid sequence herein, and more typically has an increasing identity, preferably at least 75%, 85%, 90%, 91%, 92%, 93%, 94%, 95%, 96%, 97%, 98%, 99% or almost 100% identify.

TABLE 1

Sequence List

| Serial number | Sequence title | Amino acid sequence |
| --- | --- | --- |
| SEQ ID NO: 1 | CDR1 | GFTFSSYG |
| SEQ ID NO: 2 | CDR2 | ISPGGSYT |
| SEQ ID NO: 3 | CDR3 | ARRDLDY |
| SEQ ID NO: 4 | CDR1 | GYTFTSYW |
| SEQ ID NO: 5 | CDR2 | IYPGNSDT |
| SEQ ID NO: 6 | CDR3 | TREDYDYDWYFDV |
| SEQ ID NO: 7 | CDR1 | GYSFTGYY |
| SEQ ID NO: 8 | CDR2 | INPSTGGT |
| SEQ ID NO: 9 | CDR3 | ARVLYDYEGSGFAY |
| SEQ ID NO: 10 | CDR1 | GYSFTGYT |
| SEQ ID NO: 11 | CDR2 | INPSTGDT |
| SEQ ID NO: 12 | CDR3 | ARVLYDYEGPGFAY |
| SEQ ID NO: 13 | CDR1 | QSLLYSDGKTY |
| SEQ ID NO: 14 | CDR2 | QVS |
| SEQ ID NO: 15 | CDR3 | LQGTYFPHT |
| SEQ ID NO: 16 | CDR1 | ESVEYYGTSL |
| SEQ ID NO: 17 | CDR2 | GAS |
| SEQ ID NO: 18 | CDR3 | QQSRKVRT |
| SEQ ID NO: 19 | CDR1 | KSLLHSNGNTY |
| SEQ ID NO: 20 | CDR2 | RMS |
| SEQ ID NO: 21 | CDR3 | MQHLEYPFT |
| SEQ ID NO: 22 | CDR1 | KSLLYHSNGLNTY |
| SEQ ID NO: 23 | CDR2 | RAST |
| SEQ ID NO: 24 | CDR3 | MQHLEYPFAT |
| SEQ ID NO: 25 | A heavy chain V region of a humanized antibody | EVQLQQSGSELVKP GASVKISCKASGYS FTGYYMNWVKQSPE KSLEWIGEINPSTG GTTYNQKFKAKATL TVDKSSSTAYMQLK SLTSEDSAVYYC |
| SEQ ID NO: 26 | A light chain V region of a humanized antibody | DIVMTQAAPSVPVT PGESVSISCRSSKS LLHSNGNTYLYWFL QRPGQSPQLLIYRM SNLASGVPDRFSGS GSGTAFTLRISRVE AEDVGVYYCMQHLE |

An ADRB3 antibody involved in the present invention further includes a rabbit monoclonal antibody, a rat-derived antibody, a chimeric antibody, a fully human antibody, a single domain antibody, a single chain antibody (scFv), a bispecific antibody, a Fab antibody fragment, a synthetic antibody and the like, which are characterized by being capable of specifically binding to an ADRB3. Cells used to produce antibodies include CHO, SP2/0, BHK-21, Vero, etc.

Furthermore, it should be understood that, after reading the above contents of the invention, those skilled in the art may make various alterations or modifications to the invention, which likewise fall within the scope defined by appended claims of the application.

Specifically, the present invention finds through a lot of researches the following effects of an ADRB3 and an anti-ADRB3 polyclonal antibody:

The present invention discloses that an ADRB3 is a new immunoregulation receptor and tumor marker, discloses physiological functions of the ADRB3 and its role in a pathological mechanism of a disease, and discloses an anti-human ADRB3 monoclonal antibody and application thereof. The antibody according to the invention is specific to a human ADRB3 amino acid sequence, and can specifically bind to the ADRB3 and regulate the biological activity thereof. The antibody regulates differentiation and functions of tumor cells, hematopoietic stem cells, myeloid progenitor cells, lymphocyte progenitor cells, dendritic cells, natural killer cells, neutrophils, lymphocytes and monocytes-macrophages, and plays a role in anti-cancer, anti-inflammation and reversing tumor immune tolerance. The antibody can induce differentiation and maturation of T-lymphocytes (T cells), and recover apoptosis ability thereof to enhance specific immune functions thereof. The antibody can also induce differentiation of tumor cells, inhibit proliferation thereof, and kill tumor cells by antibody-dependent cell-mediated cytotoxicity (ADCC), complement-dependent cytotoxicity (CDC) and direct action (including the mechanisms, such as blocking cell cycle, inhibiting ribosomal synthesis, reducing mitochondrial membrane potential, inducing apoptosis, inhibiting mitochondrial autophagy, inhibiting pentose phosphate pathway, inhibiting glycolysis, reducing ketone body synthesis and reducing lipid metabolism. The antibody according to the invention is obtained by a mouse hybridoma technique and is transformed by humanization. The present invention discloses antigenic epitopes of the antibodies and a hybridoma cell train for producing a monoclonal antibody. The hybridoma cell train includes, but is not limited to, 5D9 and 5B8 deposited with the China Center for Type Culture Collection (CCTCC) of Wuhan University under accession number CCTCC NO: C2016203 and CCTCC NO: C2016202 on Dec. 12, 2016, and the hybridoma cell can secrete an ADRB3 monoclonal antibody. An amino acid sequence of an ADRB3 antibody "variant" according to the invention contains one or more "conservative" amino acid changes relative to the sequence, and a preferred antibody structure and a constant domain are a human structure and a human constant domain. The present invention discloses an application of the antibody and development of a detection kit thereof. The anti-human ADRB3 monoclonal antibody can be used for immunological experiments, such as Western blot, fluorescence in situ hybridization technique, immunoprecipitation, immunohistochemical analysis, enzyme-linked immunosorbent assay (ELISA), immunofluorescence, magnetic bead separation, immune colloidal gold test and flow cytometry, and quantitatively and qualitatively detect a soluble ADRB3 protein or an ADRB3 protein fragment in human serum, human histocytes, human secreta and human cell cultures. The anti-human ADRB3 monoclonal antibody according to the present invention can be used for activating or blocking the ADRB3 effects.

The present invention discloses that the ADRB3 is a new T cell co-inhibitory molecule and a tumor marker, regulates the activation, proliferation, differentiation, apoptosis and immune response of immune cells, and regulates the expression of immune cells in immunosuppressive regulatory T cells (Treg), myeloid-derived suppressor cells (MDSC), tumor infiltrating neutrophils (TINs) and many types of cancer cells. The ADRB3 exists in a membrane form or in a soluble form, and detection of ADRB3 content in histocytes or body fluids helps to predict therapeutic effects, therapy applicability and disease diagnosis. The ADRB3 in tumor cells induce immune suppression of an organism, and changes T cell behaviors, so that T cells can neither differentiate to sensitized effector cells, nor destroy tumors. Pathogens, such as tumor cells, senescent cells, viruses and bacteria, can induce high expression of the ADRB3 in lymphocytes, granulocytes, monocytes, dendritic cells, and NK cells, and inhibit antigen presentation and immune cell activation by an ADRB3-mediated signaling pathway, so that pathogens, such as tumor cells, senescent cells and viruses, are not identified by the immune system to avoid being eliminated. An ADRB3 antibody blocks the ADRB3 signaling pathway, eliminates immune cells capable of high expression of ADRB3, and recovers normal functions of lymphocytes, so that the immune system can identify and eliminate pathogens, cancer cells and senescent cells.

An ADRB3 has the functions of a chemotactic factor, an immunosuppressive receptor and a neural cell adhesion molecule. An ADRB3 binds to a tumor marker protein (tumor polypeptide) in a nucleolus, and then a complex "MHC class I molecule-tumor polypeptide-ADRB3" is displayed on the surface of cancer cells. A CD8+ T cell binds to a MHC class I molecule to result in direct contact between the CD8+ T cell and cancer cells. The ADRB3 will be adhered to the CD8+ T cell from the surface of the cancer cells to inhibit the CD8+ T cell using an immunoreceptor tyrosine-based inhibition motif (ITIM) of the ADRB3, so that CD8+ T cells cannot kill cancer cells.

Abundant ADRB3 are present in poorly differentiated cells, such as naive immune cells and cancer cells. An ADRB3 inhibits the attack of T cells on a tumor by overexpression in the tumor and inhibiting lymphocyte activation. An ADRB3 is an inducible protein, is rarely present in normal cells, is present in tumor cells and immune cells in a tumor microenvironment under pathological conditions, and promotes the formation of an immune microenvironment for tumor proliferation. A PD-1 or CTLA-4 knockout mouse will have a severe autoimmune disease. An ADRB3 knockout mouse will not suffer from a cancer, atherosclerosis, senile dementia or an autoimmune disease, and will have a significantly prolonged life. An ADRB3 antibody has not only a function of directly killing a cancer cell, but also an effect like an immune checkpoint inhibitor (ICI) effect, and eliminates a cancer cell by activation of specific immunity. A compound inhibitor or a neutralizing antibody may be used to block an ADRB3 signaling pathway, so as to effectively inhibit tumor growth, kill cancer cells at a proliferation phase and a resting phase, and induce differentiation and maturation of tumor cells and naive lymphocytes. It can not only reduce the malignancy degree of a tumor, but also restore the anti-cancer function of an immune cell. Because normal lymphocytes and histocytes almost have no ADRB3, the antibody will not damage normal immune systems or tissues, and is an efficient broad-spectrum anticancer drug with low toxicity and target specificity.

Sympathetic-adrenal medulla regulates the immune function through an ADRB3, which is a key protein to maintaining the homeostasis of a nerve-endocrine-immune network. Diseases and senility are abnormal life activities caused by homeostatic regulation disorder of the nerve-endocrine-immune network. An ADRB3 antibody inhibits the ADRB3 activity, enables the immune system to re-identify and eliminate tumor cells infected with a pathogen and senescent cells, and has anti-cancer, anti-inflammatory and anti-aging effects, and an effect of promoting regeneration.

The present invention discloses that an ADRB3 is a new lymphocyte suppressor molecule, and has 3 immune receptor tyrosine-based inhibitory motifs (ITIM) with the following ITIM amino acid sequences: ITIM 1: (143) LRYGAL (148) or (143) LRYGTL (148) or (140) LRYRAV (146); ITIM 2: (202) IPYALL (207) or (202) MPYVLL (207) or (199) VPYALL (204); ITIM 3: (212) SFYLPL (217). An ADRB3 inhibits differentiation, maturation and self-identification of T cells, NK cells and macrophages, so that T cells, NK cells and macrophages are unable to eliminate aged and damaged cells, but immunologically kill normal cells. Unlike innate immunosuppressive molecules, e.g., CD28 family proteins, of lymphocytes, an ADRB3 is a disease-induced expression. Under normal circumstances, there is a small amount of ADRB3 on lymphocyte membranes. In a pathological state of a tumor, viral infection, an autoimmune diseases or the like, innate immunocytes (e.g., neutrophils) or tumor cells induce lymphocytes to produce a large amount of the ADRB3, which shuttle from cytoplasm to cytoblast, regulate gene expression, alters lymphocytic phenotypes, promotes inhibitory lymphocyte proliferation and inhibits specific immunity, thereby accelerating disease progression. The immunosuppressive effect of an ADRB3 on lymphocytes will enhance activities of innate immune cells, particularly neutrophils and macrophages, by feedback, thereby resulting in inflammation in an organism. Tumors and virus induce ADRB3 expression in lymphocytes, and block lymphocytic apoptosis. Dead lymphocytes are danger signals for the immune system. Dead immune cells convert antigen-presenting cells (APC) in a resting state into an activated state, then activate T cells by antigen presentation, and play a role in anticancer and eliminating pathogens. An ADRB3 antibody induces apoptosis of granulocytes, macrophages and lymphocyte capable of high expression of the ADRB3, releases danger signals, activates a specific immune system, and recovers anti-cancer function of lymphocytes. An ADRB3 antibody specifically eliminates "pathogenic" lymphocytes containing inducible ADRB3 without damaging normal lymphocytes, restores normal death and apoptosis of lymphocyte, and normalizes the immune system to avoid autoimmunity.

The present invention discloses that an overexpressed or functionally enhanced ADRB3 causes a cancer, an inflammation, an autoimmune disease and aging. An overactivated ADRB3 interferes with the regulation of innate immunity over specific immunity, so that lymphocytes become non-functional naive cells because differentiation is blocked. Poorly differentiated lymphocytes fail to identify nonself and self-organization, so that tumor cells escape from immunity and cause an autoimmune disease. After blocking the ADRB3 signaling pathway, normal immunity can be restored, so that T cells can eliminate cancer cells and senescent cells to avoid autoimmune injury. An ADRB3 is a key link between natural immunity and specific immunity, enhances the natural immune response induced by neutrophils, NK cells and macrophages, and stimulates lymphocyte proliferation. The inventor has found that a MMTV-PyVT ADRB3 knockout mouse carrying a mouse breast cancer virus will not have a breast tumor. An ADRB3 knockout mouse has a extended life, and will not have an autoimmune disease or cancer. An exogenous tumor cell cannot grow in its body. The level of an inflammatory factor, such as IL-4 and IL-6, in the serum of an ADRB3 knockout mouse is significantly reduced, and the count of primitive and naive granulocytes is reduced. The inventor has developed a monoclonal antibody blocking human ADRB3, and has applied it in treating a cancer, an inflammation and an autoimmune disease. An ADRB3 antibody enhances specific antitumor response of a mouse, and reduces a systematic inflammation. An ADRB3 antibody treats 4T1 breast cancer-bearing mice, inhibits proliferation and distant metastasis of a carcinoma in situ, reduces neutrophils, MDSC and Treg, enhances the antigen presentation ability of dendritic cells, activates the anticancer activity of complements, NK cells and CD8$^+$ T cells, reduces a neutrophil-lymphocyte ratio (NLR), and plays anti-cancer and anti-inflammatory roles. An ADRB3 antibody stimulates human lymphocyte differentiation in vitro, and induces the production of CD8$^+$ T cells with an anticancer activity.

The present invention discloses a new mechanism controlling innate immunity and specific immunity, that is, sympathetic nerve-adrenal medulla first activates constitutively expressed ADRB3 in granulocytes and monocytes-macrophages to activate innate immune cells, and then inhibits lymphocyte activation by promoting induced expression of the ADRB3 by lymphocytes. Anxiety, depression and other high-level mental stress reduce the immune functions of an organism through an ADRB3, and increase the risk of suffering from a cancer, diabetes, atherosclerosis, senile dementia or other diseases. Abnormal activation of the ADRB3 will cause disorders of the innate immune system and a specific immune system, which is reflected as overactivation of myeloid cells represented by neutrophils. However, lymphocytes can't be activated, both the count of neutrophils and its percentage in leukocytes are enhanced, and NLR is increased, thereby resulting in a chronic systemic inflammation in the organism. ADRB3-mediated immune disorder is a common pathological mechanism of an autoimmune disease, an inflammation, a tumor, viral infection, atherosclerosis, Alzheimer disease and aging. The pathological process of a tumor is most typical. The early stage of a carcinoma in situ mainly includes: an ADRB3 activates neutrophils and macrophages in local tissues, and increases inflammatory factor levels, and cancer tissues infiltratively grow in local areas. If the activity of an ADRB3 is continuously hyperactive, granulocytes, spleen, liver and tumor cells can all secrete soluble ADRB3, thereby inducing ADRB3 expression in NK cells and lymphocytes. An ADRB3 in lymphocytes changes epigenetic modification, inhibits differentiation and maturation of NK cells and lymphocytes, and fails to eliminate circulating tumor cells in blood, resulting in distant metastasis of the tumor. At present, tumor immunotherapy is mainly to enhance lymphocyte-mediated specific immune functions without desired target sites for regulating innate immune cells, resulting in poor anti-cancer effects and easily causing an autoimmune disease. An ADRB3 antibody can relieve the inhibitory effects of neutrophils and macrophages on NK cells and lymphocytes, and restore immune recognition of NK cells and lymphocytes to tumors.

The key to tumor immunotherapy is to restore normal death or apoptosis of lymphocytes, and dead lymphocytes can give play to their greatest immune functions. The existing tumor immunotherapies usually promote T cell proliferation, prevent T cell apoptosis, and may be efficacious in the early stage, but frequently relapse and cause severe autoimmunity. The present invention proposes a new tumor immunotherapy, i.e. induce T cell death under the prerequisite of controlling the count of dead T cells. An ADRB3 antibody is applied from a small dose. Once it is observed that a tumor is reduced or the count of neutrophils is less than 1,000/mm$^3$, the dose can be reduced or use of the ADRB3 antibody may be stopped to prevent excessive ADRB3 antibody from damaging normal T cells.

Present in membranes of T cells, B cells, macrophages, NK cells, dendritic cells and tumor cells, an ADRB3 integrates inhibitory signals to regulate the activation of lymphocytes. A large number of conical "ADRB3" fractal structures are present on the surface of and within cancer cells, T cells and dendritic cells to maintain adhesive interfaces of immune cells and tumor cells, so that they are firmly bound. The conical ADRB3 complex begins in the cell membrane, runs through the cytoplasm, and extends to the cytoblast to form a channel. Extracellular substances, such as neurotransmitters and pathogens, enter the cytoblast using the channel to regulate DNA replication and gene expression, and affect cell differentiation and proliferation. An ADRB3 antibody destroys the adhesion between immune cells and tumor cells and blocks the inhibition of T cells by tumor cells. An ADRB3 regulates the formation and signal transduction of immune synapses, collects other immune signaling molecules (e.g., B7/CD28, PD-L1/PD-1) and transmits signals. An ADRB3 signaling pathway transmits inhibitory signals to intracellular areas, and plays a role in negatively regulating the activation of T cells and NK cells. ADRB3 plays an important role in negatively regulating the initial reaction stage and activation stage of initial T cells and the re-reaction stage of memory T cells. Effector T cells with high expression of ADRB3 genes survive because of having anti-apoptosis ability, and develop into memory T cells. An ADRB3 promotes the proliferation of CD4+ T cells, enhances the activity of Treg, and inhibits the activation of CD8$^+$ T cells, so that lymphocytes fail to eliminate cancer cells, cells infectious with pathogens and senescent cells, thereby resulting in a malignant tumor, atherosclerosis, an autoimmune disease, Alzheimer disease and aging.

The inventor has found that an ADRB3 participates in the antigen processing and presentation process, and regulates immune recognition and immune response of an organism. ADRB3 aggregates in a site where APC and lymphocytes contact with each other, which contributes to the stability of intercellular adhesion molecules, and promotes adhesion of dendritic cells, macrophages and granulocytes to lymphocytes. An ADRB3 in APC is involved in antigen processing, so that a processed tumor cannot be identified by lymphocytes because of missing antigen information. An ADRB3 regulates antigen processing by the following mechanisms. (1) The ADRB3 has the functions of acetylase, and regulates the acetylation of antigen information, so that the acetylated tumor antigen can neither retain its antigenicity, nor activate T cells. (2) ADRB3 promotes autophagy of endocytic vesicles containing antigenic information in APC. An ADRB3 promotes lysosome maturation. Antigen-containing endocytic vesicles bind to lysosomes to accelerate autophagic degradation of the endocytic vesicles, eliminate antigen information of a tumor, and inhibit immune recognition and response of a specific immune system to the tumor. (3) In APC, such as dendritic cells, macrophages and B cells, the ADRB3 will be adhered to MHC II class molecules by an outer membrane covering the autophagosome, thereby forming a complex "ADRB3: polypeptide: MHC II class molecule", which is presented to the surface of the APC, and then directly contacts with CD4$^+$ T cells, thereby inhibiting T cell responses.

Expression levels of the ADRB3 in tumor cells, lymphocytes and granulocytes of a cancer patient are significantly increased, thereby inhibiting a second signal system required for T cell activation. T cells become immune incompetent, so that the tumor escapes from immunity.

ADRB3 is located in organelles, such as cell membranes, lysosomes, mitochondria, ribosomes, cytoblast and nucleolus to regulate the functions of the organelles. ADRB3 has the specificity of rapidly transporting cytoplasm, after synthesis, to cytoblast, shuttling back and forth between nucleoplasm, acting as a transport carrier between cytoblast and cytoplasm for signal transmission, and regulating DNA replication and gene expression. ADRB3 in cytoblast promotes cells at G0 phase to enter the proliferation phase, and ADRB3 in cancer cells is usually localized in cytoblast, suggesting that ADRB3 stimulates proliferation of cancer cells. Proliferation of cancer cells can be inhibited by inhibiting the ability of ADRB3 in cell membrane and cytoplasm to enter cytoblast.

ADRB3 gene expression and protein localization are significantly different in tumor cells of different malignancy degrees. In cancer cells of low malignancy degree, ADRB3 is less expressed, is mostly localized in cytoblast, and is less localized in cell membrane. In cancer cells of high malignancy degree, ADRB3 is highly expressed, and is distributed in cytoblast, cytoplasm and cell membrane, which contributes to contact with immune cells to play a role in immunosuppression. In tumor patients, ADRB3 inhibits lymphocytes by the following channels: ①. ADRB3 induces APC to transmit inhibitory signals to lymphocytes; ②. ADRB3 on the tumor cell membrane directly contacts with and inhibits lymphocytes; ③. tumor cells secrete ADRB3 or ADRB3-containing exosomes to regulate lymphocytes as signal molecules. An ADRB3 antibody can antagonize immunosuppressive function of ADRB3, and is cultured together with immune incompetent T cells of cancer patients to relieve the incompetent state of T cells, restore T cell functions, and play a role in treating cancers.

ADRB3 can stimulate cell proliferation and inhibit differentiation, and plays a key role in proliferation of malignant tumor cells, myeloid cells, lymphocytes, NK cells, dendritic cells and hematopoietic stem cells. The present invention discloses that ADRB3 is a "proliferation marker" for evaluating cell proliferation ability, and the more the ADRB3 is, the stronger the cell proliferation ability is. At present, the commonly used proliferation markers include Mcm, Ki-67 and PCNA. The common defects of the 3 proteins are that they cannot be expressed in cells at G0 phase, can only be expressed after the metaphase of G1, and there is a "diagnostic gap". The advantages of the ADRB3 are that the ADRB3 is expressed in the whole proliferation phase including early phase of G1 and G0 phase, and can more comprehensively and accurately reflect the proliferation ability of cells. The ADRB3 is used in an animal model for basic and clinical researches, selecting drugs and evaluating human diseases. The animal model is an effective tool for researching the mechanisms of aging, stem cells, stress, tumor, regeneration, cell cycle and G0 phase, determining patient prognosis, and guiding diagnosis and treatment.

The ADRB3 is a "proliferation marker" for evaluating cell proliferation ability, and the more the ADRB3 is, the stronger the cell proliferation ability is. For cancer cells, the more the ADRB3 is, the lower the differentiation degree is, and the higher the malignancy degree is. ADRB3 is a target protein for researching a drug inducing differentiation.

ADRB3 is present in initial T cells, and is directly regulated by the sympathetic nerve to prevent the initial T cell death. But the result is that some initial T cells which are nonfunctional and have an effect on killing themselves survive, thereby resulting in an autoimmune disease. ADRB3 content in T cells can be detected, and used as an important index of a specific immune system function. The higher the ADRB3 content in T cells is, the poorer the antigen recognition function is, and the more easily the normal histocytes are damaged. ADRB3$^+$ T cells are cells that contribute to autoimmunity.

The present invention discloses a new mechanism of regulating proliferation and differentiation of T cells, i.e., the sympathetic nerve-adrenal medulla system activates ADRB3 of hematopoietic stem cells and T cells in peripheral immune organs to stimulate T cell proliferation and inhibit differentiation. The ADRB3 promotes hematopoietic stem cells at G0 phase and T cells to enter the cell cycle for mitosis. Under normal circumstances, the ADRB3 signaling pathway maintains immune tolerance. Under pathological conditions, overactivated ADRB3 enables mature T cells to lose specific immune functions after differentiation or transdifferentiation, and causes immune escape, autoimmunity, allergic reaction and the like of tumors.

The present invention discloses that the development and differentiation of NK cells, macrophages, neutrophils and lymphocytes specific in spleen and liver depend on the ADRB3 regulation network. The ADRB3 with abnormal activity inhibits the functions of macrophages and lymphocytes in the spleen, and cannot eliminate aged blood cells, pathogens and foreign matters, thereby resulting in human aging. The ADRB3 antibody restores the spleen's ability to eliminate aged and damaged blood cells, and delays senescence.

The ADRB3 regulates the development and differentiation of hematopoietic immune tissues of liver, promotes production of granulocytes, lymphocytes, macrophages, NK cells and lymphocytes in liver, and promotes enrichment of natural immune cells in liver. Hyperactive ADRB3 signaling pathway will increase the hematopoietic functions of liver, increase to produce neutrophils, and cause an inflammation, an autoimmune disease and a cancer. In normal liver cells, most of the ADRB3 are distributed in cytoplasm, and a few are distributed in cytoblast. The content of ADRB3 in hepatocytes of hepatitis patients is increased. ADRB3 increases the functions of hepatocyte ribosomes, promotes the synthesis of c-reactive proteins, complements and coagulation factors in liver, and aggravates systemic inflammatory responses. ADRB3 stimulates inflammatory cell infiltration in liver, and the count of granulocytes, lymphocytes, macrophages and NK cells with high expression of ADRB3 in liver tissues is significantly increased. In a patient with liver cancer or cirrhosis, the content of ADRB3 in hepatocytes is increased, the ADRB3 is mainly distributed in cytoblast, and the count of ADRB3$^+$ granulocytes and ADRB3$^+$ macrophages in liver is increased. In liver, ADRB3$^+$ granulocytes and ADRB3$^+$ macrophages are environmental cells that form metastases, and ADRB3 antibodies inhibit the liver metastasis of breast cancer cells. The ADRB3 antibody can restore liver hematopoiesis and immune functions, inhibit liver inflammations, reduce liver fibrosis, and be used to treat hepatitis and cirrhosis.

The mechanism for the ADRB3 to regulate T cell proliferation and differentiation is as follows: (1) catecholamine activates ADRB3 on cell membranes of T cells at G0 phase, activates P62/mTOR/AKT signaling pathways, increases synthesis of the proteins, such as Ki-67, CDK3 and Cyclin D1, and induces "dedifferentiation" of mature T cells, which then enter the proliferation phase. (2) When an activated ADRB3 on T cell membrane is invaginated in cells, a dimer is formed in cytoplasm to expose the leucine zipper structure domain, is transported into cytoblast along microtubules, and binds to nuclear DNA. The ADRB3 in cytoplasm can form a heterodimer with c-Myc, and regulates the transcriptional activation of genes by an E box structure binding to the promoter region. (3) The ADRB3 has the functions of acetylase, increases the acetylation of nucleosomal H3 histones, changes the epigenetic state of cells, helps to unwind tightly compressed chromatin, and contributes to proliferation-related gene transcription.

After mitosis, the ADRB3 is degraded by ubiquitination, and new T cells are gradually differentiated and mature. If the degradation of ADRB3 is limited, naive ADRB3$^{bright}$ T cells (T cells with strongly positive ADRB3) cannot differentiate or be mature, and the organism will be in specific immunodeficiency. The ADRB3 antibody closes a ligand binding domain of the ADRB3 on naive T cell membranes, competitively inhibits ADRB3 activation by catecholamine, enables the lymphocytes to depart from proliferation phase, and induces lymphocytes to enter G0 phase to develop and become mature.

The present invention discloses that the expression level of the ADRB3 in lymphocytes is an index to measure of specific immune functions and aging degrees. The higher the expression level of the ADRB3 in lymphocytes is, the lower the specific immune functions are, the more serious the aging degree of the organism is, and the higher the mortality risks are.

The present invention discloses to detect the ADRB3 content in lymphocytes of blood to select early cancer patients. Mature lymphocytes of normal people do not express or express a small amount of ADRB3, and the expression level of which is less than that of neutrophils. Tumor cells and granulocytes induce lymphocytes to express ADRB3 and inhibit the activation of lymphocytes. If the expression level of the ADRB3 in lymphocytes is close to or more than that of neutrophils, and it is accumulated in cytoblast and nucleoli, the cells are ADRB3$^{bright}$ lymphocytes, suggesting that the cells are undifferentiated or are differentiated, but lose anticancer function. The ADRB3 antibody is used to detect Ki-67 negative lymphocytes (ADRB3$^{bright}$ Ki-67$^-$) with high expression of ADRB3 in peripheral blood, and can be used as a physical examination index to screen patients with early-stage cancers. ADRB3$^{bright}$ Ki-67$^-$ lymphocytes account for more than 10% of the total lymphocyte count, suggesting high risk tumor groups or patients with early-stage cancers. If ADRB3 is highly expressed together with Ki-67 positive (ADRB3$^{bright}$ Ki-67$^+$) in more than 50% lymphocytes of the peripheral blood, it suggests that naive lymphocytes can be neither differentiated nor mature, and have serious specific immunodeficiency, and shows that the cancer enters a progressive stage.

The present invention discloses that the ADRB3 is a tumor marker, and its expression level in cancer cells is significantly increased, compared with that in normal cells. The ADRB3 expression level is associated with the severity, size and stage of a tumor. Changes of the ADRB3 concentration in body fluid are associated with the therapeutic effect, and the concentration reduction suggests that the treatment is effective. The ADRB3 level is significantly increased in case of relapse, and detection of the ADRB3 concentration could predict relapse. The ADRB3 antibody can detect not only the ADRB3 expression level in tumor tissues, but also the ADRB3 expression level in exfoliated cells of urine, sputum, ascites, hydrothorax, cerebrospinal fluid and bronchioalveolar lavage fluid, and is applicable to cancer screening among ordinary populations and diagnosis of cancer patients.

The present invention discloses detection of ADRB3 fusion genes in tumor tissues and ADRB3 gene mutation, deficiency, insertion, repetition, chromosome translocation and rearrangement, etc., which has an important reference value for guiding treatment of tumor patients.

The ADRB3 is highly expressed in hematopoietic stem cells, lymphoid progenitor cells, lymphocytes (B cells, T cells), myeloid progenitor cells, myeloid cells (erythrocytes, granulocytes, monocytes and megakaryocytes), NK cells, tumor cells, osteoclasts and microglia. Especially, the ADRB3 is highly expressed in myeloblasts, promyelocytes, myelocytes, neutrophils, eosinophils, myeloid-derived suppressor cells, tumor-associated macrophages (TAM), mastocytes, dendritic cells (DC), abnormal lymphocytes, Treg, plasmocytes, primitive lymphocytes and naive lymphocytes. The present invention discloses that the ADRB3 is an antigenic marker of myeloid cells and naive lymphocytes, human ADRB3 is mainly expressed in myeloid cells, and no or a small amount of the ADRB3 is expressed in mature lymphocytes, but the ADRB3 expression level is increased in naive lymphocytes. Overactivated ADRB3 in lymphocytes and neutrophils inhibits immune surveillance and immune defense, and is the basis for a plurality of diseases. The ADRB3 inhibits the differentiation of myeloid progenitor cells and lymphocyte progenitor cells, and weakens the defense mechanism against cancer cells, viruses and other pathogenic microorganisms. Cancer cells, pathogenic microorganisms and aging cells can activate ADRB3 signaling pathways of neutrophils and lymphocytes, stimulate dedifferentiation of mature neutrophils and lymphocytes, which then become poorly differentiated naive cells or primitive cells, and inhibit the effect of monitoring, defensing and regulating the immune system. The ADRB3 antibody blocks immunosuppressive function of the ADRB3, induces differentiation of tumor cells, myeloid progenitor cells and lymphocyte progenitor cells, blocks dedifferentiation of mature neutrophils and lymphocytes, and restores normal functions of lymphocytes, NK cells, monocytes-macrophages, dendritic cells, neutrophils and complement systems.

Cell dysdifferentiation is the root cause of most diseases, such as tumors, cardiovascular diseases, inflammation and aging. A tumor is essentially the cell dysdifferentiation, and the key to treating tumor is to restore the differentiation ability of cancer cells. The inventor has found that the ADRB3 is a key protein for regulating differentiation, and after the ADRB3 is blocked, tumor cells can restore differentiation ability and differentiate to normal or nearly normal cells.

Hypofunction caused by lymphocyte differentiation defects is the basis for malignant tumors and autoimmune diseases. Differentiation disorders of cardiomyocytes, neurons and the like will lead to heart failure and neurodegenerative diseases. The differentiation function defect of important organs is the key factor of aging. The inventor has put forward the "two dysdifferentiation knockout hypothesis" on the aging and disease production mechanism. The occurrence of diseases is the result of the cell differentiation deficiency, which produces nonfunctional cells, and is the first "dysdifferentiation knockout". Under normal circumstances, nonfunctional cells can be eliminated without causing disease attack on the organism. But immune cell dysdifferentiation, if any, will cause immunodeficiency of the organism, and the immune cells can not eliminate tumor cells, aging cells and non-functional cells produced by the first "dysdifferentiation knockout", which will lead to disease attack due to the second "dysdifferentiation knockout". The inventor has found that after myocardial infarction, necrotic myocardium infiltrates inflammatory cells with high expression of ADRB3, and prevents differentiation of cardiac stem cells to mature myocardial cells, thereby resulting in incomplete differentiation. Then, cardiac stem cells become naive myocardial cells and fibroblasts, thereby resulting in myocardial remodeling and heart failure. The left anterior descending coronary artery of ADRB3 knockout mice (ADRB3$^{-/-}$ mice) is ligated to prepare a congestive heart failure model after myocardial infarction. Compared with the ADRB3 wild type mice, the left ventricular ejection fraction (LVEF) of ADRB3$^{-/-}$ mice is significantly increased, but myocardial remodeling is not obvious. Compared with the young adult ADRB3$^{-/-}$ mice (10-30 weeks old), the LVEF of aged mice (70 weeks old) is not significantly reduced, and the LVEF of some ADRB3$^{-/-}$ mice (70 weeks old) is even higher than that of mice of 10 weeks old. The inventor has constructed Apo E/ADRB3 double knockout mice, which are feed with high fat diets, and has found that the number of atherosclerotic plaques in the Apo E/ADRB3 double knockout mice is significantly less than that of Apo E knockout mice. The double knockout mice have stronger learning and memory ability and obviously extended life than the Apo E knockout mice. The inventor has found that a lot of granulocytes, macrophages and lymphocytes with high expression of ADRB3 are infiltrated in human tumor tissues, these inflammatory cells induce cancer cells to express ADRB3 in great quantities by way of directly contacting with cancer cells and releasing ADRB3, aggravate cancer cell dysdifferentiation, and increase the malignancy degree of cancer cells, thereby resulting in distant metastasis and drug resistance. In conclusion, blocking ADRB3 by knocking out an ADRB3 gene or using a neutralizing antibody can restore differentiation function of tissue cells and immune cells, avoid two "dysdifferentiation knockouts", and eliminate pathogenic microorganisms, cancer cells and damaged tissue cells using immune cells of the organism.

The present invention discloses that the ADRB3 induces cell fusion, and ADRB3 agonists and human ADRB3 protein drugs produced using gene recombination technology can be used as inducers to promote cell fusion, and can be used for somatic hybridization, animal and plant distant hybridization, lymphocyte hybridoma and monoclonal antibody preparation. The ADRB3 with a leucine zipper structure domain can draw independent biological membranes closer, and then promotes to integrate the membranes, which contributes to biological membrane fusion between different cell types and promotes formation of tissues and organs. ADRB3 plays an important role in the process of forming cell organelles such as mitochondria, and the process of evolution from prokaryotic cells to eukaryocytes and from unicellular organisms to multicellular organisms. ADRB3 promotes the fusion of different proteins, such as promoting the formation of promyelocytic leukemia-associated PML- RARα fusion proteins. The fusion of ADRB3 gene and other proto-oncogenes will promote tumor progression. ADRB3-mediated cell fusion causes chromosomal instability, and too many centrosomes (3 or more) resulted from cell fusion will lead to three- or four-stage mitosis or prolonged mitosis. The inventor has found that ADRB3 increases the number of centrosomes and promotes polyploid formation. ADRB3-mediated cell fusion contributes to tumor formation. Macrophages, neutrophils or lymphocytes play an important role in the fusion of tumor cells by high ADRB3 fusion ability. ADRB3 induces fusion of granulocytes and cancer cells, increases the heterogeneity and phenotypic instability of cancer cells, produces cells that are more malignant than parents, accelerates tumor metastasis, and enables cancer cells to be resistant to drugs. ADRB3 plays a key role in the process of cell fusion mediated by viruses such as human papillomavirus, hepatitis B virus, hepatitis C virus, HTLV-1 and EBV. ADRB3 antibodies can block virus-mediated cell fusion.

The inventor has found that activated ADRB3 will dedifferentiate cells, change the gene expression profile and epigenetic modification, and change the cell phenotype. ADRB3 has a leucine zipper structure domain, has the ability to bind to DNA and RNA, and can also mediate the dimerization or polymerization of various transcription factors. ADRB3 and other transcription factors form oligomers, which bind to gene promoters to activate or inhibit transcription of target genes. Activated ADRB3 on cell membrane is invaginated into cytoplasm to form homodimers or heterodimers. ADRB3 having the functions of acetyl transferase bind to promoters of more than 3000 genes (about 12% of the genome) to regulate the histone acetylation state of nucleosomes, promote gene transcription associated with cell proliferation, and inhibit differentiation and maturation by stimulating proliferation of tumor cells, lymphocyte progenitor cells and myeloid progenitor cells.

The present invention discloses a lymphocyte which highly expresses ADRB3 molecules in a cell nucleus. The lymphocyte does not express or lowly express marker proteins of myeloid cells—myeloperoxidase (MPO), and has potential of differentiation to myeloid cells. The inventor names the cell as $MPO^{dim/-}$ $ADRB3^+$ lymphocyte, and the lymphocyte is a lymphocyte progenitor cell or a lymphoblast. The multiplication and differentiation of the $MPO^{dim/-}$ $ADRB3^+$ lymphocyte are regulated by ADRB3; when the activity or expression quantity of ADRB3 increases, the lymphocyte will differentiate to the myeloid cell, being manifested as that the expression of MPO is increased, granulocyte-like change occurs to the cell nucleus, and the karyotype is in an irregular reniform and lobulated shape. ADRB3 induces the differentiation of the $MPO^{dim/-}$ $ADRB3^+$ lymphocytes to the myeloid cells so as to reduce the lymphocytes, resulting in the increased neutrophils and macrophages to cause the depletion of T cells.

The $MPO^{dim/-}ADRB3^+$ lymphocytes have an immunosuppression function, and a sympathetic nervous system regulates the cell through ADRB3 to maintain the balance between inherent immunity and adaptive immunity. Few $MPO^{dim/-}ADRB3^+$ lymphocyte lymphocytes are found in a human body normally, but a number of $MPO^{dim/-}ADRB3^+$ lymphocyte lymphocytes are found in peripheral bloods, spleens, livers and bone marrows of patients suffering cancers, Alzheimer disease, viral hepatitis and autoimmune disease and the elderly. The $MPO^{dim/-}ADRB3^+$ lymphocytes stimulate the proliferation of cancer cells, and the activity has good compatibility, and has the proliferation promotion effect for a breast cancer, a pancreatic cancer, a lung cancer, a colon cancer, a glioma, a melanoma, a sarcoma, etc. The $MPO^{dim/-}ADRB3^+$ lymphocytes promote the infection and replication of a hepatitis virus, an aids virus and other viruses. An ADRB3 antibody inhibits the functions of the $MPO^{dim/-}ADRB3^+$ lymphocytes, blocks the differentiation of the $MPO^{dim/-}ADRB3^+$ lymphocytes to the myeloid cells, and promotes the $MPO^{dim/-}ADRB3^+$ lymphocytes to be differentiated to mature lymphocytes.

The present invention discloses that ADRB3 induces the dedifferentiation of CD4 or CD8 single positive T cells in the peripheral bloods and bone marrows to $CD4^+CD8^+$ double positive (DP) T cells. ADRB3 inhibits the apoptosis of the DPT cells and promotes the proliferation of the DPT cells, and increases the contents of the DPT cells in the blood. The $CD4^+CD8^+$ cells are remarkably increased in the peripheral bloods of the elderly and the patients suffering the virus infection, tumor and autoimmune diseases. ADRB3 antibody blocks the proliferation of the DPT cells so as to reduce the cell count, and is suitable for treating diseases and aging caused by the increasing of the DPT.

The present invention discloses that ADRB3 promotes the trans-differentiation of the $CD8^+$ T cells to the MDSC and neutrophils in myeloid cells. On one hand, ADRB3 reduces the in-vivo $CD8^+$ T cell count and causes the depletion of the $CD8^+$ T cells; on the other hand, ADRB3 increases the proportion and count of Treg, MDSC and neutrophils in bloods, bone marrows, spleens and lymphonodi, resulting in systemic inflammation.

The present invention discloses that ADRB3 is a new B cell surface molecule, ADRB3 regulates the proliferation, differentiation, apoptosis and immune response of the B cells, and ADRB3 is expressed in the cytoplasm and cell cytolemma of the B cells and plasma cells.

The invention discloses a method for identifying plasma cells, which uses an ADRB3 antibody for immunofluorescence or immunohistochemistry; if a number of ADRB3s are accumulated in the cytoplasms of the lymphocytes, the cells are plasma cells. ADRB3 affects the activity of the B cells and the plasma cells, increases the synthesis of a relevant surface marker like CD19, and promotes the plasma cells to synthesize autoantibodies. ADRB3 antibody inhibits the B cells to produce immunoglobulins, reduces the synthesis of the autoantibodies, and is used to treat autoimmune diseases.

The present invention discloses that ADRB3 is a pattern recognition receptor (PRR) and has the following functions: (1) opsonization; (2) inhibition of complement activation; (3) phagocytosis and autophagy; and (4) activation of immunocyte activation and inflammatory signal transduction. The mutual recognition and interaction of ADRB3 and pathogen-associated molecular patterns is the key to initiate an inherent immunity response. ADRB3 is capable of recognizing bacterial lipopolysaccharide (LPS), lipoprotein (BLP), peptidoglycan (PGN), yeast mannan, and the like. ADRB3 regulates the activity and signal transduction of other pattern recognition receptors such as Toll receptors, scavenger receptors, mannose receptors and C-type lectins. ADRB3 regulates the innate immune response mediated by NK cells, macrophages, eosinophils, neutrophils, and mastocytes, etc. ADRB3 is an important receptor for pre-inflammatory reactions, which recognizes bacterium, fungi, and viral components by regulating pattern recognition receptors and plays an important role in cell infection by pathogens. ADRB3 enables the pathogens to survive in the cells, and the mechanism is as follows: 1. ADRB3 promotes autophagy, while the autophagy promotes the replication and release of the pathogens such as viruses, bacterium, or parasites in the cells. 2. ADRB3 reduces the production of reactive oxygen, while the reactive oxide species can kill foreign pathogens. 3. The cytolemma ADRB3 mediates the adhesion, fusion and entry of bacterium, fungi, viruses, parasites and other pathogens. ADRB3 is a key fusion protein of the virus-host cell membrane fusion. After the pathogen enters the host cell, a safe barrier-vacuole is established with the help of ADRB3, which can escape the digestion of lysosomes. ADRB3 antibody can remove bacterium, fungi, viruses, parasites and other pathogens inside the cells.

Non-specific immunity (inherent immunity) is the basis of all immunoprotective abilities and can initiate and participate in specific immune (adaptive immunity) responses. The soluble ADRB3 content in the blood can be used as an important indicator of the function of a non-specific immune system. Most of the current immunotherapeutic drugs are directed against specific immunocytes, ignoring a large number of non-specific immunocytes, and resulting in low efficiency of immunotherapy. ADRB3 antibody of the present invention can simultaneously regulate the functions of non-specific immunocytes and specific immunocytes, restore the immune system to a normal state, and is used for treating diseases caused by disorders of the immune system.

The present invention discloses that ADRB3 regulates the proliferation of hematopoietic stem cells, can enhance the regenerative capacity of hematopoietic stem cells in vivo, and stimulate the bone marrow to accelerate hematopoiesis. ADRB3 is expressed on the surfaces of the stem cells and affects the distribution and quantity of adhesion factors. ADRB3 antibody changes the bonding strength of the hematopoietic stem cells and extracellular matrixes in the bone marrows to allow the hematopoietic stem cells to enter the peripheral bloods. ADRB3 antibody can be used to separate and collect the hematopoietic stem cells for transplantation of the stem cells in the peripheral bloods.

The present invention discloses that ADRB3 is a major cytokine regulating bone marrow hematopoiesis, can act on granulocyte hematopoietic progenitor cells, promote the proliferation and differentiation of the cells, and increase the count and functions of terminally differentiated granulocytes, i.e., the neutrophils in the peripheral bloods. ADRB3 stimulates the maturation of granulocytes and monocytes-macrophages, promotes the release of mature cells into the peripheral bloods, and can promote the multiple functions of macrophages and eosnophils. An ADRB3 agonist and a human ADRB3 protein drug produced using a gene recombination technology can be used as a hemameba growth promoter for preventing and treating leukopenia caused by radiotherapy or chemotherapy of tumors, treating bone marrow hematopoietic dysfunction and myelodysplastic syndrome, preventing potential infectious complications of leukopenia, and accelerating the recovery of infection-induced neutropenia. The indications include: (1) promotion of increasing the neutrophils count during bone marrow transplantation; (2) prevention of the neutropenia caused by anti-tumor chemotherapy drugs and shortening of the duration of neutropenia; and acute lymphocytic leukemia; (3) neutropenia in myelodysplastic syndrome; (4) neutropenia in aplastic anemia; (5) congenital and primary neutropenia; (6) neutropenia secondary to immunosuppressive therapy (renal transplantation); and (7) hypohepatia.

ADRB3 regulates the bone marrow hematopoiesis and promotes the growth of red blood cells. ADRB3 agonists and the human ADRB3 protein drug produced using a gene recombination technology can be used as a red blood cell growth promoter for treating anemia. The ADRB3 agonist, ADRB3 antibodies with ADRB3 activation function, and ADRB3 recombinant protein factors improve the oxygen carrying capacity of an athletic body, improve the athletic performances, repair damaged tissue, and can be used for athlete training and recovery after injury.

The present invention discloses that ADRB3 is a novel inflammatory factor that exerts a pro-inflammatory effect in an autocrine and paracrine manner. An ADRB3 signaling pathway regulates the pathological processes of systemic infection and autoimmune diseases. The ADRB3 signaling pathway regulates P62, Elastase, HK2, GAPDH, Cyclin D1, P21, P16, P27, Ras, CDK3, CDK4, Rb, Ki-67, mTOR, c-Myc, Rheb, PI3K, AKT, Tubulin, Actin, VEGF, TRAF6, PD-L1, ZAP70, P53, Interleukin6 (IL-6), IL-10, IL-4, IL-5, IL-2, MPO, IFN-γ, GM-CSF, C-reactive protein, acetyltransferase Tip60, TGF-β and TNFα and other protein molecules in the neutrophils, macrophages, lymphocytes and tumor cells.

The present invention discloses that ADRB3 is a biomarker of myeloid-derived suppressor cells (MDSCs), ADRB3 is highly expressed in MDSCs, and the growing development of the MDSCs is dependent on ADRB3. ADRB3 promotes MDSC proliferation, and the ADRB3 antibody inhibits MDSC functions, and treats patients with resistant and recurrent tumors.

The present invention discloses that Ki-67 and ADRB3 appear in the MDSCs, lymphocytes, monocytes-macrophages and neutrophils of malignant tumor patients in the meanwhile, and the double positive (Ki-67$^+$ ADRB3$^+$) granulocyte count of Ki-67 and ADRB3 is positively related to the poor prognosis of the tumors. The cell is a primordial or immature granulocyte, with the ability of inducing the T cells to be dedifferentiated to immature T cells. ADRB3 and Ki-67 are co-localized in the granulocyte cytoplasm. ADRB3 enhances the granulocyte ribosome function and promotes the synthesis of Ki-67 and other cell growth factors. The granulocytes release the Ki-67 and growth factors, and stimulate the lymphocytes and tumor cells at G0 phase to enter the proliferation phase. Ki-67$^+$ ADRB3$^+$ granulocytes are cells for marking aggravation, and the continuously increased cell count highly prompts transfer or relapse of the patient.

The present invention discloses a new neutrophil, which produces and secretes a number of ADRB3 molecules, and is named as ADRB3$^+$ granulocyte. The cell can inhibit the innate immunity of an organism, and regulates the maturation of the lymphocytes. ADRB3$^+$ granulocyte contents and percentages of tumor patents, virus or bacterium infected persons are obviously increased. The spleens of tumor patients and especially the chronic granulocytic leukemia patients are active organs to produce the ADRB3$^+$ granulocytes, while the ADRB3$^+$ granulocytes from the spleens will promote tumor progression and transfer. The proportion of the ADRB3$^+$ granulocytes in the hemamebas is obviously increased in the spleens, bone marrows and peripheral bloods of the tumor patients after chemotherapy and the ADRB3+ granulocytes promote the tumor cell at G0 phase to enter the proliferation phase to cause cancer relapse. Infusing the ADRB3 antibody in the splenic artery by catheterization is beneficial for the target killing of the ADRB3$^+$ granulocytes, and preventing the tumor from transfer.

The ADRB3$^+$ granulocytes adhere and carry the tumor cells to generate distant metastasis. ADRB3 delays the death of neutrophils and increases the concentration of neutrophils in the tissue. ADRB3 increases ribosome functions, stimulates neutrophil synthesis, releases inflammatory factors and growth factors, induces angiogenesis, and potentiates inflammatory responses. ADRB3 protects mitochondrion functions, reduces the generation of reactive oxygen, and allows parasites, bacterium, or viruses phagocytosed by granulocytes or macrophages to develop and proliferate within cells. This is an immune evasion mechanism for pathogens. The ADRB3+ granulocytes in blood induce the lymphocytes to highly express ADRB3 by ways of adhering the lymphocytes or releasing ADRB3 into the blood, so as to cause the dedifferentiation of the lymphocytes and result in special immunodeficiency.

Normal human neutrophils have less surface protrusion and the ADRB3 content is significantly less than that of cancer patients. The granulocyte foot processes in cancer patients increase, and ADRB3 regulates microtubules and microfilaments to promote the formation of the granulocyte foot processes. ADRB3 promotes the granulocyte foot processes to adhere and capture the lymphocytes, and induces the lymphocytes to lose anti-cancer activity. The tumor patients have a large number of extracellular trapping nets (NETs) of neutrophils in the blood to adhere and capture the lymphocytes and tumor cells. ADRB3 is the main component of NETs. The tumor cells in the NETs use ADRB3 to inhibit the lymphocytes. NETs are the mediating environment between tumors and lymphocytes. The ADRB3 antibody inhibits the formation of NETs.

During the formation of atherosclerotic plaques, ADRB3 promotes the granulocytes to be adhered to vascular endothelial cells and migrates into subendothelium to form NETs which are used to attach the lymphocytes and the macrophages and secrete cytokine IL-6, enlarge the accumulation of the immune cells in atherosclerotic lesions, cause a chronic inflammatory response, and form lipid-rich plaques. ADRB3 promotes the fusion of the foam cells in the granulocytes and plaques, and the foam cells acquire the ability to proliferate and migrate as the plaques extend along the vessel walls. ADRB3 activates elastase (Elastase) in the neutrophils and foam cells, and releases the elastase into vascular wall tissues. The elastase digests elastins and collagens in the middle layer of the blood vessel wall. Vascular elasticity is an important character of maintaining normal physiological functions of a blood vessel. The vascular elasticity is mainly provided by elastin fibers. ADRB3 promotes the degradation of the elastins and reduces the vascular elasticity, making an arterial wall thicker and harder, narrowing a lumen, and resulting in arteriosclerosis, pulmonary hypertension, and hypertension. The elastic tissues such as lungs and hearts are rich in elastin. The main sources of lung and heart elastase are neutrophils and macrophages. ADRB3 promotes the elastase to release from the neutrophils and macrophages, causes the lowering of the elasticity of the lungs and hearts, destroys the tissue structures, causes pulmonary emphysema, bronchiectasis, asthma, pulmonary fibrosis, dilated cardiomyopathy, and ventricular hypertrophy, etc. The present invention discloses that the ADRB3 antibody which acts as an elastase inhibitor, can inhibit the activity and release of the granulocyte elastase, and is used for treating diseases caused by the invasion of elastase, including but not limited to: pancreatitis, pulmonary emphysema, pulmonary hypertension, asthma, myocardosis, ventricular hypertrophy, cirrhosis, cerebral ischemia, cerebral hemorrhage, and cerebral trauma.

ADRB3 causes the activation, aggregation, and infiltration of the neutrophils, and is a key step in the development and progression of inflammatory reactions. ADRB3 promotes the adhesion of the neutrophils to the surfaces of microvascular endothelial cells in an ischemic area tissue during the ischemia/reperfusion injury of various organs such as brain, liver, lung, intestine, kidney, and heart, blocks capillary vessels, forms a no-reflow phenomenon, and reduces the blood supply to the tissue. The neutrophils accumulate in the capillaries and release both inflammatory mediators and proteolytic enzymes. The inflammatory mediators can attract more neutrophils to aggregate, and cause the inflammatory response to form a malignant cycle of self-proliferation. Proteolytic enzymes degrade almost all the extracellular matrix components of leukocytes and attack intact cells, resulting in shedding of endotheliocytes, increasing microvascular permeability, and severe damage to the blood-tissue barrier, resulting in pulmonary edema, cerebral edema, or the like, aggravating tissue damages and causing ischemic necrosis. The ADRB3 antibody attenuates the activity of neutrophils, reduces the extent of necrotic tissues after ischemia-reperfusion, and enhances the recovery of microvascular functions in the ischemic area. The present invention discloses that the ADRB3 antibody is used for treating the ischemia/reperfusion injury of brain, liver, lung, intestine, kidney, and heart.

The neutrophils in the tissue phagocytose senescent cells, and then disintegrate and degranulate to release intracellular ADRB3. ADRB3 becomes a soluble receptor that is endocytosed by the tissue cells at G0 phase, migrates into the nucleolus, increases the nucleoli functions, and promotes the synthesis of large and small ribosomal subunits. ADRB3 increases the synthesis of various RNA (such as U3 snRNA) and proteins (such as cyclin, cyclin kinase, etc.) necessary in G1 phase and activates cells at G0 phase into the G1 phase. The G0 phase is the period of cell differentiation. ADRB3 promotes the cells in G0 phase to enter the proliferative phase, which means that the cells lose the ability to differentiate. The high concentration of ADRB3 in the tissue continues to stimulate the cell proliferation, inhibits the differentiation of new cells, and induces tumorigenesis. Granulocytes gain energy through glycolysis, and ADRB3 is a key protein that maintains the neutrophil glycolysis. Tumor cells highly express ADRB3, and the metabolic pattern of the cells is changed to be mainly based on glycolysis. The present invention discloses that the ADRB3 antibody can inhibit the glycolysis of the tumor cells.

The neutrophil glycolysis immersed in tumor tissues produces large amounts of lactic acid, which activates the monocarboxylic acid (MCT) translocator through ADRB3 to secrete lactic acid, causing the tumor environment to contain large amounts of lactic acid. ADRB3 binds to an SLC16A3 gene promoter to increase the MCT4 expression, and promote the transmembrane transport of lactic acid. The lactic acid with a high concentration is the energy source of tumors, but the lactic acid inhibits the activity of cytotoxic T cells and NK cells, leading to immune escape of the tumor cells. The extracellular acidic environment of the tumor cells promotes the degradation and remodeling of extracellular matrixes, which is beneficial for the invasion and metastasis of cancer cells. The ADRB antibody interferes with the lactic acid efflux, neutralizing the extracellular acidic microenvironment of the tumor cells. In inflammatory conditions such as sepsis, catecholamines increase the lactic acid in blood by stimulating ADRB3 in the neutrophils and lymphocytes, resulting in poor prognosis of the patients. The present invention discloses that the ADRB3 antibody inhibits the efflux of MDSCs, neutrophils, and lymphocytes, and treats hyperlactatemia and lactic acidosis. The ADRB3 antibody inhibits $H^+/K^+$-ATP enzyme, and blocks gastric acid secretion, and is used for treating duodenal ulcer, gastric ulcer, reflux esophagitis, *Helicobacter pylori* infection.

Aging cells, tumor cells, endotoxins, bacteria and viruses increase the ADRB3 gene expression in the granulocytes and lymphocytes, and increase the ADRB3+ granulocyte and ADRB3+ lymphocyte count and the concentration of soluble ADRB3 in blood. ADRB3 is produced in the vascular endothelial cells, neutrophils and lymphocytes of a sepsis patient and released into blood, while ADRB3 in blood can activate the neutrophils, and explosively secretion cytokines, resulting in uncontrollable inflammatory responses, and causing multiple organ dysfunction syndromes. In the tumor patients, the ADRB3+ lymphocytes and soluble ADRB3 promote the distant metastasis of tumors. In the elderly, ADRB3 restricts tissue regeneration, impedes the differentiation of new cells, and the new cells cannot be developed into functional cells. This incomplete regeneration accelerates aging of the organism or induces tumors.

Under physiological conditions, ADRB3 promotes the clearance of neutrophils, macrophages, and lymphocytes from senescent dead cells, while stimulating cells of tissues and organs in the G0 phase to enter the proliferative phase, producing progeny cells through mitosis, and ADRB3 of the new cells is lower in expression, re-enters the G0 phase and differentiates into functional cells to replenish dead cells. This process is called "complete regeneration". The cells have to differentiate and mature in order to maintain normal tissue and organ functions, so that the organism will not become aging. If ADRB3 is hyperactive in the new cells after mitosis to cause that the new cells cannot enter the G0 phase, which inhibits the cell differentiation and make the cells fail to mature, then this process is "incomplete regeneration" and causes aging and tumors. The inventor has found that the content and activity of soluble ADRB3 in the blood and cerebrospinal fluid of the elderly are both higher than those of the youngster, and over-activated ADRB3 causes "incomplete regeneration" and cannot repair the aging tissues and organs. The ADRB3 antibody inhibits incomplete regeneration, restores complete regeneration, and has anti-aging effects.

The concentration of ADRB3 in blood shows fluctuations in the daily, monthly, and annual cycles, regulating the stress, metabolism, proliferation, or differentiation of cells, which is beneficial to the regeneration of the organism. Maintaining the periodic fluctuations of the concentration of ADRB3 in the blood is the key to regeneration regulation. If the concentration fluctuation curve of ADRB3 in the blood disappears, it should be regulated according to the concentration of ADRB3. When the production and release of ADRB3 is excessive (such as tumor or inflammation), the ADRB3 antibody is administered to reduce the activity of ADRB3 and restore it to normal levels. When the concentration of ADRB3 is too low, an ADRB3 agonist is administered to increase the activity of ADRB3. The cell mitosis is promoted by activation or over-expression of ADRB3 to start tissue regeneration; the differentiation of new cells is maintained by blocking ADRB3, so that the new cells are transformed into functional mature cells to restore the functions of tissues and organs. The ADRB3 antibody regulates the regeneration of tissues such as heart, liver, bone marrow, pancreas, brain, peripheral nerve, kidney, lung, and muscle. Reducing the concentration and activity of ADRB3 in the blood, cerebrospinal fluid, and tissues with low ADRB3 function can promote cell proliferation and play an anti-aging role.

The invention discloses that the ADRB3 antibody is used for promoting tissue regeneration and treating the disease caused by regeneration dysfunction, which includes but is not limited to: leukopenia, neutropenia, lymphopenia, aplastic anemia, chronic granulomatous disease, leukocyte adhesion deficiency, B-cell deficiency disease, X-linked agammaglobulinemia, T-cell deficiency disease, severe combined immunodeficiency disease, complement deficiency disease, burn, unhealed wound, sarcopenia, senile muscular dystrophy, osteoporosis, senile macular degeneration, presbycusis, and other senile diseases.

Inflammation is an important part in immunoreaction of an organism, and chronic inflammation leads to cancer, Alzheimer disease and other feeble-mindedness diseases, cardiovascular disease, osteoarthritis, depressive disorder and other diseases, and more than 90% noninfectious aging diseases are related to the chronic inflammation. The initial phase of inflammation is caused by neutrophils, and the ADRB3 signaling pathway plays a key role in the activation process of the neutrophils. The ADRB3 gene knockout mice can resist the endotoxin in large dose to delay the occurrence of pyaemia, so as to reduce the death caused by the pyaemia, which means that the pyaemia is related to the activity of the ADRB3 signaling pathway. The activated ADRB3 is a "gate" for generating various inflammatory mediators, and a cascade reaction of the inflammatory mediator is triggered through a "trigger sample" effect. ADRB3 used as an inflammatory factor can promote the neutrophils, lymphocytes, eosinophils, and monocytes-macrophages to release MPO, Elastase, IL-1, IL-6, VEGF and other inflammatory factors. Moreover, the increase of inflammatory factor further stimulates the activation of ADRB3 in turn, which plays a role of amplifying the inflammation.

ADRB3 promotes eosinophils, basophils and lymphocytes to generate and release histamine, leukotrienes, platelet activating factor, etc. causes the shrinkage of smooth muscle, the expansion of blood capillary, and the strengthening of permeability, and the secreta of gland is increased, which causes the anaphylactic reaction of partial or whole body. The invention discloses that the ADRB3 antibody has the functions of stabilize mast cell membrane, prevents degranulation, inhibits the lymphocyte transformation and the generation of interleukin, reduces the Langerhans cell count on the surface, inhibits the platelet aggregation, strengthens deformation capability of erythrocyte, and inhibits the division and proliferation of the cells. The ADRB3 antibody is used for treating allergic diseases and allergic contact dermatitis.

The invention discloses that the soluble ADRB3 is a tumor marker of serology, for monitoring the concentration of the soluble ADRB3 in blood or other body fluids, which has an important value to the early diagnosis, prognosis estimation, therapeutic reaction and relapse monitoring of malignant tumors. The inventor has found that ADRB3 exists in blood, cerebrospinal fluid, hydrothorax, ascites and other fluids, and includes all structural domains outside the cytomembrane, has the ability of bonding with a ligand, and is named as soluble ADRB3 (sB3). The tumor cells can generate and release ADRB3 into the blood to increase the content of ADRB3 in the blood. The content of sB3 in the blood of a tumor patient is higher than that of a normal person, sB3 in the blood of a tumor relapse patient is higher than that of a treated and relieved patient, and the survival rate of the tumor patient with high level sB3 is lower than the patient with low level sB3. sB3 can be bonded to NK cells, T cells and monocytes to inhibit immunity, and enable the tumor to escape from the immune monitoring. sB3 is beneficial for increasing the activity of circulating tumor cells, and the ADRB3 antibody can eliminate the circulating tumor cells through ADCC effect.

Except for the treatment purpose, the anti-human ADRB3 monoclonal antibody is further used for researching human ADRB3 ELISA detection reagent, soluble ADRB3 enzyme-linked detection reagent, colloidal gold detection reagent, etc. The content of sB3 in blood, saliva, urine, cerebrospinal fluid, hydrothorax, ascites and other body fluids is detected, which can be used in the diagnosis and therapeutic evaluation of pyemia, angiocardiopathy, Alzheimer disease, tumor and autoimmune disease. sB3 in serum can be used as an diagnosis index and illness monitoring marker of pyemia, myocardial infarction, autoimmune disease, malignant tumor and other diseases. Detecting the content of sB3 in blood and other fluids can forecast the life and the death rate in five years, and the higher the concentration of sB3 is, the larger the risk of death is. Reducing the content of sB3 in blood can delay senescence.

ADRB3 downwardly regulates the classic pathway and replacement pathway of complement activation to enable bacteria, viruses and tumors to escape from the immunoreaction of host. ADRB3 reduces the expression of complements C3, C5, C8 and C9, blocks the formation of membrane attack complex (MAC), and enables the tumor cells to escape from complement attack. Through constituent and inductive expression of ADRB3, the tumors and virus-infected cells can limit MAC assembly to protect themselves to avoid harmful damages caused by the complements. The present invention discloses that the ADRB3 antibody can activate a complement system, increase the expression quantity of C3, C5, C8 and C9, promote the MAC assembly, start the cytolysis of tumor cells, eliminate the pathogenic microorganism, and lyse the infected cells, and is used for treating malignant tumors, virus infection, gonococcal infection, etc.

The invention discloses that ADRB3 is an inflammation marker, and the change of the ADRB3 level reflects the inflammation of partial or whole body. The soluble ADRB3 (sB3) is the extracellular component of ADRB3 on the cell surface fell off after protein decomposition, the level of sB3 in circulating is parallel to the change of ADRB3 of the neutrophils, so that sB3 detected in the serum can be used as an index for the function monitoring of the neutrophils. The ADRB3 antibody plays a role of limiting the inflammation, and is used for treating the diseases caused by the infection of different pathogenic microorganisms, such as fungus, bacterium, virus, *mycoplasma, chlamydia,* spirochete, protozoon and parasite. The inflammation is a dangerous factor of tumor, the inflammation caused by ADRB3 can develop the infection or the autoimmune diseases into a tumor, then the tumor cells further substantially secrete ADRB3 and other pro-inflammatory factors, which aggravates the inflammatory reaction, promotes the distant metastasis, and accelerates the death of the patient. The immunocytes in the tumor microenvironment such as neutrophils, Treg and macrophages promote the development of tumor. ADRB3 secreted by the tumor cells increases the content of ADRB3 in the blood and partial tumor tissues, promotes the granulocytes, lymphocytes, macrophages and other inflammatory cells to transfer and infiltrate to the tumor tissues. The inflammation and the tumor cells can both activate ADRB3 and ADRB3 plays a key role of maintaining chronic inflammation, promoting tumor progression and inhibiting the immune surveillance aiming at the tumor. ADRB3 is a key link of having relation between the inflammation and the tumor, so that a positive feedback loop is formed between the inflammation and the tumor, which causes that the inflammation and the tumor are mutually promoted. The ADRB3 antibody interdicts a vicious circle chain of the inflammation and the tumor, inhibits the recruitment of the inflammatory cells to the tumor part, relieves the inflammatory reaction in the tumor microenvironment, and plays the dual roles of anti-inflammation and anticancer.

The tumor releases ADRB3 into the blood to activate the neutrophils, weaken the specific immunoreaction mediated by T cells, and cause cachexia. ADRB3 in the cancer cells induces the proliferation of myeloid derived suppressor cells such as MDSC and Treg, inhibits the antitumor immune response of cytotoxic T lymphocytes (CTL) and natural killer cells (NK), enables the cancer cells to escape from immune killing, and promotes the proliferation and metastasis of tumors. ADRB3 in the tumor recruits normal endothelial progenitor cells to reach to the tumor tissue, and promotes the formation of new vessels. The ADRB3 antibody inhibits the expression and activity of ADRB3 of the myeloid derived suppressor cells and the tumor cells in the tumor microenvironment, which not only can relieve the inflammatory environment of tumor to play a role of increasing the tumor immunity, but also can directly inhibit the proliferation of the tumor cells, and is suitable for treating malignant tumors and cachexia.

According to the light and heavy chain sequencing result of the ADRB3 antibody, the present invention discloses that the T cells after the modification of anti-ADRB3 chimeric antigen receptor not only can eliminate the tumor cells expressing ADRB3, but also can eliminate cancer-promoting inflammatory cells in tumor microenvironment, increase the therapeutic effects of other chimeric antigen receptor T cell immunotherapy (CAR-T), and are used in the tumor patient with failed CAR-T treatment. The cancer cell, granulocytes, T cells and macrophages induce the dedifferentiation of the CAR-T cells, so that the CAR-T cell losses the antitumor activity. The ADRB3 antibody can maintain the differentiation state of the CAR-T cells, and increase the kill capability of the CAR-T to the cancer cells. The chimeric antigen receptor is composed of a single-chain antibody, a CD8 hinge domain and a transmembrane domain of mice anti-human ADRB3, a intracellular signaling domain of CD137 (alternately named 4-1BB), and the intracellular signaling structure of CD3ζ in series. The anti-ADRB3 CAR-T cells can eliminate the cancer-promoting inflammatory cells (neutrophils, Treg and macrophages) in the tumor cells and the internal environment of tumor; even though the tumor cells do not express ADRB3, the anti-ADRB3 CAR-T cell can still play a role of anticancer through inhibiting the cells in the tumor environment, is a general CAR-T cell, and is used for treating malignant tumor, autoimmune diseases, atherosclerosis, inflammation, virus infection, and neurodegenerative diseases such as Alzheimer disease and senile disease.

The present invention discloses the macrophages, dendritic cells, NK cells and granulocytes after the modification of the anti-ADRB3 chimeric antigen receptor, which can eliminate tumor cells and aging cells, is used in adoptive immunity to treat malignant tumors, autoimmune diseases, atherosclerosis, inflammation, virus infection, neurodegenerative disease and senile disease.

The present invention discloses gene therapy based on ADRB3, which uses CRISPR/Cas9, TALEN and ZFN technologies to delete, add, activate or inhibit the ADRB3 genes. The gene therapy is used in anti-aging and the treatment to malignant tumors, autoimmune diseases, atherosclerosis, inflammation, virus infection, Alzheimer disease and senile disease. The indications of the gene therapy based on ADRB3 target spot are the same as that of the ADRB3 antibody.

The present discloses that ADRB3 is a new monocyte surface molecule, the ADRB3 regulates the differentiation and proliferation of monocytes-macrophages, promotes the monocytes to differentiate to M1-type macrophages, and more particularly, regulates the activity of the tumor-related macrophages.

The invention discloses a new macrophage, which substantially generates and secretes a number of ADRB3 molecules, and is named as ADRB3$^+$ macrophage, and the cell inhibits the innate immunity of an organism.

The present discloses that ADRB3 is a new erythrocyte surface molecule.

The present discloses that ADRB3 is a new megakaryocyte and blood platelet surface molecule.

The present discloses that ADRB3 is a new NK cell surface molecule.

The present discloses that ADRB3 is a new dendritic cell surface molecule.

The present invention discloses that the ADRB3 gene is a proto-oncogene related to cell proliferation, and ADRB3 is a key driving factor in most cancers. In pancreatic cancer, breast cancer, lung cancer, colorectal cancer, liver cancer, melanoma, lymphoma, leukemia and other malignant cells, ADRB3 is highly expressed abnormaly. The ADRB3 gene is mainly activated through amplification and chromosome translocation rearrangement. The fusion, overexpression and mutation of the ADRB3 gene can lead to the disorder of ADRB3 proteins, and the abnormal ADRB3 proteins will activate multiple carcinogenic signaling pathways in downstreams, including PI3K/IAKT/mTOR, RAS/MAPK, Jak/Stat, TGF-/Smad, ErbB/HER, Wnt/Hedgehog/Notch, etc.

The present invention discloses that ADRB3 promotes the tumor metastasis, and the ADRB3 antibody retards the tumor metastasis, which can be used for treating the terminal cancer patient with distant metastasis. ADRB3 increases the transfer ability of the tumor cells to enable the tumor cells to enter the blood, and increase the interaction between the tumor cells and the neutrophils to promote the tumor metastasis. The circulating tumor cells substantially express ADRB3, the tumor cells adhere to the granulocytes and macrophages with the help of ADRB3, and are carried by the granulocytes and macrophages to other places, so as to be metastasized. The tumor metastasis not only depends on the invasion ability of the tumor itself, but also is closely related to the formation of pre-metastatic niche before the tumor metastasis. The construction of pre-metastatic niche decides whether the tumor cell invading to a circulatory system can adhere, exist and proliferate at distant metastasis and finally form the metastatic cancer. After the granulocytes and macrophages in the blood enter the tissues, the ADRB3 factors can be released to build a microenvironment suitable for the existence of the tumor cells. The soluble ADRB3 proteins secreted by the circulating tumor cells can induce bone marrow precursor cells to be mobilized and implanted to distant and specific organic tissues to form the pre-metastatic niche, and the circulating tumor cells are recruited to specific site to form the.

The increase of the ADRB3 level in the tumor cells is related to bad clinic results including the increase of metastasis velocity, and the rate of relapse and death. The detection to the content of ADRB3 in tumor tissues can be used in the diagnosis, prognosis and therapeutic evaluation of the malignant tumor. The concentration of soluble ADRB3 in blood is increased, which prompts that the development of tumor is accelerated or relapsed, and the patient has bad prognosis.

The present invention discloses that ADRB3 is a key structural protein in the cell nucleolus, and plays an important role of maintaining the nucleolus functions. ADRB3 accumulates in the nucleolus of the cell at G0 phase, promotes the synthesis of large and subunits of ribosome, and participates in gene silencing, cell senescence and cell cycle control. ADRB3 promotes the expression of Ki-67 gene and the protein synthesis, activates the resting G0 cells to enter the proliferation phase. The ADRB3 antibody inhibits the function and structure of tumor cell nucleolus. ADRB3 is located in the nucleolus of the cells at G0, G1, S and G2 phases, promotes the conversion between the resting phase (G0) and the proliferation phase, and promotes the mitosis. ADRB3 regulates the function and structure of the cell nucleolus at G0 phase and proliferation phase, but the configurations of ADRB3 in the cell nucleolus at G0 phase and proliferation phase are different, and the exposed epitopes are also different. Therefore, different ADRB3 antibodies are needed to detect ADRB3 in the nucleolus of different cell cycles. Different ADRB3 polypeptide fragments are used in the present invention to produce the ADRB3 antibody, the antibody generated by immunity of N-end fragment of ADRB3 protein (1-155th amino acid residues) can detect ADRB3 in the cell nucleolus at proliferation phase. The antibody generated by immunity of intermediate structural domain fragment of ADRB3 protein (100-300th amino acid residues) can detect ADRB3 in the cell nucleolus at resting phase. In the detection of immunohistochemistry, immunofluorescence and flow cytometry, the epitope being the monoclonal antibody of N-end polypeptide of ADRB3 is applied to detection of the cell at proliferation phase, and the epitope being the monoclonal antibody of intermediate domain of ADRB3 is applied to detect the cells at G0 phase.

The present invention discloses that ADRB3 is a marker of the cells at G0 phase, and only the cells at G0 phase expressing ADRB3 can enter the cell cycle again. The chemotherapeutics cannot kill the cancer cells at G0 phase, the cancer cells at G0 phase is the root of relapse of the cancer. Circulating tumor cells and dispersed tumor cells are induced to a resting state because of lacking original microenvironment of growth. The ADRB3 antibody specifically kills the cancer cells at G0 phase, prevents the cancer cells at G0 phase from entering the proliferation phase (such as G1 phase), and is used for treating relapsed and drug-fast malignant tumor patients. The ADRB3 antibody eliminates the circulating tumor cells at G0 phase, and is used for preventing the cancer cells from metastasizing.

The distribution state of ADRB3 in the cell nucleus is closely related to different phases of the cell cycles. The distribution of ADRB3 in the cell nucleus at G0 phase is different from that of ADRB3 in the cell nucleus at proliferation phase, and the large amount of accumulation of ADRB3 in the nucleus is a markeric event of the cells at G0 phase entering G1 phase. ADRB3 is accumulated in the nucleus of Ki-67 negative cell, which indicates that the cell will enter G1 phase from G0 phase. The present invention discloses that the ADRB3 antibody is used in an immunofluorescence experiment, to detect the ADRB3 hot spots in the nucleolus, which can authenticate the cells at G0 phase with the proliferation capability (in FIG. 1, the cells at the upper right are the cells at G0 phase with the proliferation capability), and the authentication standard is as follows: (1) ADRB3 in the cell nucleolus is integrated into a cluster to form 2 to 6 hot spots, DAPI chromosome is negative at the parts where the hot spots locatee, and the periphery of the hot spots of ADRB3 is heterochromatic or highly compressed chromatin (strongly positive DAPI staining); and (2) the cell nucleus has no Ki-67 expression.

When ADRB3 is dispersed in the cell nucleus, it means that the cell has left G0 phase and entered the proliferation phase (G1, S or G2 in the cell cycle); at the moment, ADRB3 is used as a nuclear receptor and transcription factor to regulate the genetic expression. The present invention discloses that ADRB3 has the acetylase activity, regulates the acetylization of histone of the nucleosome, and more particularly, increases the acetylization of $9^{th}$, $14^{th}$, $18^{th}$, $27^{th}$ and $56^{th}$ lysine in H3 histone. The acetylase Tip60 can be recruited to the chromosome by ADRB3, which causes the acetylization of H4K5, H4K12 and other lysine sites of histone. The present invention discloses that the ADRB3 antibody is used as the inhibitor of acetylase, and is used for treating the diseases related to acetylation.

The completion of the structure and function of nucleolus is very important to the activity of the cancel cells, ADRB3 maintains the structure and function of nucleolus of the tumor cells at G0 phase, and increases the stress capability, which is conductive to living through a disadvantageous environment by the tumor cells. In an appropriate environment, ADRB3 stimulates resting cells at G0 phase to enter G1 phase, so as to enable the cells to differentiate and aggravate the malignancy grade of the tumor. The ADRB3 antibody damages the nucleolus function, weakens the energy metabolism of the tumor cells at G0 phase, inhibits the tumor cells at G0 phase to enter a cell cycle, and induces the cells at G0 phase to be aged and apoptotic.

Except for existing in the nucleolus of the cells at G0 phase, ADRB3 also exists in the nucleolus of the cells at G1, S and G2 phases in small amount. When there are cells entering the mitotic phase, the nucleolus raptures, and ADRB3 is located at the position of a centrosome to promote the formation of a spindle body. ADRB3 plays a key regulation role for the mitosis since ADRB3 is located at different cell cycles. The ADRB3 antibody is also suitable for killing the cancel cells at the proliferation phase.

The nucleolus is a place for replicating and transcribing various viruses. The ADRB3 antibody inhibits the nucleolus functions, interdicts virus replication, and is used for treating virus infectious diseases.

ADRB3 is located at two poles or the centrosome of the spindle body of the cell at mitotic phase to regulate microtubule generation, increase kinetochore function and promote sister-chromatid separation. The present invention discloses that ADRB3 is a microtubule associated protein, which promotes the formation of the spindle body in the cell at mitotic phase, and the ADRB3 antibody inhibits the microtubule of the tumor cells to play a role of anticancer. ADRB3 has the function of molecular motor, regulates the transmission of materials in the cells, such as autophagosome, lipofuscin, etc. The ADRB3 antibody retards the material transmission of the tumor cells, which causes that autophagosome and the lipofuscin cannot be eliminated, but accumulated in the cells, which accelerates the senescence of the tumor cells.

ADRB3 is located at the mitochondrial outer membrane of the tumor cell to maintain normal mitochondrial membrane potential and promote mitochondria fusion. The present invention discloses that the ADRB3 antibody weakens the glycolysis and oxidative phosphorylation of the tumor cell, and inhibits the generation of ATP. The ADRB3 antibody damages mitochondria transmembrane potential, promotes the mitochondria to generate active oxygen, increases the lipofuscin and other peroxides, and leads to cell apoptosis. The ADRB3 antibody inhibits the maturity of the lysosome of tumor cell, and hinders the elimination of damaged mitochondria and other metabolic wastes, such as the lipofuscin.

The present invention discloses that ADRB3 promotes the mitochondria autophagy, promotes the autophagosome to be fused with the membrane of lysosome to form autolysosome, and accelerates the elimination of the autophagosome. ADRB3 is located on an autophagy precursor membrane to promote the extension of the autophagosome membrane, so as to form complete autophagosome. ADRB3 promotes the bilayer membrane space of the autophagosome to form a hydrogen ion pool and drive V-ATPase to generate ATP, which is the main energy production manner of G0 phase cell, so that the cell does not need oxygen to maintain a dormant state of low metabolism. The ADRB3 antibody or the ADRB3 inhibitor, such as SR59230A, can interdict the autophagy, and inhibit the elimination of mitochondria autophagosome, so that the autophagosome, the damaged mitochondria, the lipofuscin and other metabolic wastes are accumulated in the cell, which accelerates the senescence or apoptosis of the cell. Except for that the apoptosis is interdicted, the ADRB3 antibody can further increase the expression of senility-related gene p16 INK4/p53/p63, reduce SIRT1 and promote the senescence of the cancer cell.

Normally, the degradation velocity of autophagosome in the cell is relatively fast, and it is difficult to detect the autophagosome. The ADRB3 antibody or the ADRB3 inhibitor can be used as an autophagy inducer to delay the degradation of autophagosome, and is used as a tool drug for autophagy studies.

The present invention discloses that the ADRB3 antibody retards a pentose phosphate pathway, and inhibits the DNA replication of the cancer cell.

The present invention discloses that the ADRB3 antibody retards the synthesis of ribosome in the cell, and decreases the capability of synthesizing protein of the tumor cell.

The present invention discloses that the ADRB3 antibody retards the stress reaction of the cancer cell, prevents the cancer cell from generating tolerance to radiotherapy and chemotherapy. The ADRB3 antibody weakens the oxidative stress capability of the cancer cell, so that the cancer cell cannot eliminate oxidative stress and active oxygen.

ADRB3 promotes the proliferation and metastasise of the cancer cells through the following mechanisms. (1) Promote P53 protein degradation, and inhibit apoptosis. (2) Promote mitochondria autophagy, glycolysis and oxidative phosphorylation, regulate a voltage dependent anion channel (VDAC) on the mitochondrial outer membrane, and activate hexokinase 2 (HK2) and GAPDH. (3) Strengthen the nucleolus functions of G0 phase and promote ribosome biogenesis. (4) Activate $H^+$-ATPase and VDAC on the lysosome outer membrane, and maintain the activity of hydrolase in the lysosome (5) Increase the expression of Cyclin D1/CDK3/CDK4, and increase Rb phosphorylation. (6) Promote spindle formation, and increase phosphorylation CENP-A. (7) Activate the stress pathway mediated by AMPK, SIRT1 and mTOR, and increase the stress capability of the cancer cells. (8) Promote the proliferation of neutrophils and MDSCs, increase the activity of regulatory dendritic cells and tumor-related macrophages, and inhibit the anticancer function of T cells and NK cells. (9) Promote the neutrophils, lymphocytes and tumor cells to synthesize IL-6, VEGF, TGF and other inflammatory factors. (10) Promote the chemotactic endotheliocyte, fibroblast, megakaryocyte, lymphocytes and granulocyte to be infiltrated to the tumor tissues, and promote the formation of new vessels. (11) Promote the circulating tumor cells to adhere to vascular endothelial cells to penetrate the endothelium to enter a tissue space, so as to form metastasis. (12) Increase the activity of P-glycoprotein, so that the cancer cells generate tolerance.

ADRB3 exists in immunocytes (neutrophils, monocytes-macrophages, and lymphocytes) and tumor cells, and has dual functions of promoting inflammation and cancer. ADRB3 increases the cancer promoting effect of the immunocytes, increases the inflammation promoting effect of the cancer cells to realize the mutual promotion between the inflammation and the tumors, so as to form a vicious circle. The ADRB3 antibody targets on a common key signal molecule in the immunocytes and tumor cells, which not only can intervene with the immunoinhibitor cells in a tumor environment, but also can inhibit the tumor cells, and effectively interdicte the development of the inflammation and tumors.

The present invention discloses that the anti-human ADRB3 monoclonal antibody is a broad-spectrum anticancer drug, the ADRB3 monoclonal antibody has the best clinical effects in application to the tumor that the cancer cells, lymphocytes or neutrophils have overexpression of ADRB3 (immunohistochemical ADRB3 is positive) or gene amplification (which is verified by fluorescence in situ hybridization detection). The malignant tumor treated includes but is not limited to: malignant lymphoma (Hodgkin lymphoma and non-Hodgkin lymphoma), acute leukemia, chronic leukemia, marrow-lymph mixed lineage leukemia, malignant histiocytosis, multiple myeloma, head and neck squamous cell carcinoma, thyroid cancer, nasopharynx cancer, oropharyngeal cancer, lung cancer, pancreatic cancer, breast cancer, esophagus cancer, gastric cancer, liver cancer, bile duct cancer, colorectal cancer, skin cancer, eczematoid cancer (Paget disease), basal cell cancer, squamous-cell cancer, melanoma, glioma, astrocytic cancer, glioblastoma, retinoblastoma, neuroblastoma, bladder cancer, kidney cancer, ovarian cancer, endometrial cancer, cervical cancer, prostate cancer, osteosarcoma, leiomyosarcoma, gastrointestinal stromal tumor, fibrosarcoma, malignant fibrous histiocytoma, liposarcoma, rhabdomyosarcoma, hemangiosarcoma, malignant thymoma, paraneoplastic syndrome and cachexia.

The ADRB3 monoclonal antibody treats adverse events related to immunity generated by immune checkpoint inhibitors, which include but are not limited to: immune-mediated pneumonia, immune-mediated colitis, immune-mediated hepatitis, immune-mediated hypophysitis, renal failure, immune-mediated nephritis, immune-mediated hyperthyroidism, and hypothyroidism.

The antibody related in the present invention can be used as a carrier to respectively conduct a guiding treatment with cytotoxic drugs (methotrexate, adriamycin, vincristine, etc.), radioisotope ($I^{131}$, $I^{125}$, $In^{111}$, etc.) or biotoxin (diphtheria toxin, ricin, etc.) in a crosslinked manner. The antibody related in the present invention can also be used as a sensitizer of chemotherapeutics to increase the curative effect of curative effect and treat the patient with drug resistance to the chemotherapeutics. The dosage form and the preparation method of the anti-human ADRB3 monoclonal antibody in the present invention are not specially limited, and the anti-human ADRB3 monoclonal antibody can be prepared into injection, preparations for external application, inhalant, oral ordinary-release preparations, capsule, granula, sustained-releasing drugs, spray, aerosol and other preparations.

ADRB3 activates the blood platelets and neutrophils, which causes hypercoagulability and high inflammation state of the blood. ADRB3 is a marker of activating the blood platelets, mediates the mutual effect among the blood platelets, endothelial cells and leucocytes, and can be used as a carrier of cancer cells to promote metastasis. The present invention discloses that the anti-human ADRB3 monoclonal antibody inhibits the activity of the blood platelets and the neutrophils, confronts platelet aggregation, prevents thrombosis, and is used for preventing and treating thromboembolism diseases, which include but are not limited to: giga-thrombocytopathia, vascular pseudohemophilia, Glanzmann thrombasthenia, thrombocythemia, deep venous thrombosis, peripheral vascular embolism, pulmonary embolism, cerebral embolism, retinal arterial obstruction, acute and subacute peripheral arterial thrombosis, central retina arterial and venous embolism, blood clotting formed in hemodialysis bypass surgery, the thrombogenesis in surgery process, cardiac catheter check, hemolytic and traumatic shock, and the septic shock complicated by disseminated intravascular coagulation (DIC).

The present invention discloses that the ADRB3 monoclonal antibody is used as a haemostatic drug, which is used under various medical conditions needing to reduce or stop the bleeding, such as the bleeding and hemorrhagic diseases of surgical department, internal medicine department, department of gynaecology and obstetrics, ophthalmology department, otolaryngology department, stomatology department and other clinical departments, and is used in hemophilia, thrombocytopenia, purpura, epistaxis, gingiva bleeding and other symptoms.

The atherosclerosis (AS) is closely related to chronic inflammation, and the inflammation caused by overactive macrophages, neutrophils and lymphocytes is a key factor leading to unstable AS plaque. ADRB3 promotes the generation of atherosclerosis and the instability of formed plaque. The chemotactic macrophages, neutrophils, lymphocytes and vascular endothelial cells are promoted by ADRB3 to adhere to and enter the plaque, which causes the rupture of plaque due to the inflammation, and aggravates myocardial ischemia even leads to necrosis, which is clinically shown as unstable stenocardia and acute myocardial infarction. The macrophage, the neutrophils and the lymphocytes rich in ADRB3 are "criminal" cells causing acute coronary syndrome (ACS). ADRB3 promotes APC to submit the antigen to T cell in an arterial wall, which causes local T cell activation and the generation of inflammatory cytokines, and the atherosclerosis is promoted through chronic inflammation and inducing the formation of foam cells. ADRB3 is an independent predictive factor of the atherosclerosis, the peripheral blood soluble ADRB3 level is positively related to the severe degree of the atherosclerosis of coronary artery. ADRB3 causes ACS through the following mechanisms. 1. Promote the inflammatory cell to adhere to vascular endothelium, and damage the endothelium, which is beneficial for depositing low density lipoprotein cholesterin (LDL-C) below the endothelium, so as to form the plaque. 2. Activate the blood platelet, macrophages, T cells and neutrophils, which causes the hypercoagulability of blood and a high inflammary state. 3. Promote the angiogenesis in the plaque. 4. Promote the granulocytes and T cells to infiltrate the plaque, which causes plaque inflammation. 5. Activate MMP, and degrade a plaque fibrous cap. 6. ADRB3 increases LDLR and scavenger receptor of the granulocytes, macrophages and endotheliocytes, stimulates the cells to phagocytoze LDL-C and chylomicron to become foam cells. 7. ADRB3 activates the pentose phosphate pathway of macrophages to generate a lot of pentose and strong reducing agent NAPDH, wherein the former is used for synthesizing nucleotide and promoting the proliferation of macrophages, and the latter can participate in the synthesis of cholesterol and increase the concentration of LDL-C, which isbeneficial for phagocytozing LDL-C by the macrophages. 8. A solute carrier (SLC) superfamily is a key protein of reverse cholesterol transport, ADRB3 increases SLC16A3 expression of macrophages, and promotes the macrophages to take up LDL-C. 9. ADRB3 increases hepatocyte ribosome function, promotes the liver to synthesize C-reactive proteins, blood coagulation factors, and very low density lipoproteins (VLDL), and aggravates vascular inflammary reaction. 10. ADRB3 promotes the monocyte to differentiate to M1-type macrophages, and increases the phagocytosis to the cholesterol so as to form the foam cells.

The present invention discloses that the anti-human ADRB3 monoclonal antibody is used for treating cardiovascular and cerebrovascular diseases, which include but are not limited to: coronary atherosclerotic heart disease, acute coronary syndrome, myocardial infarction, atherosclerosis, intracoronary stent restenosis, aortic dissection, chronic pulmonary heart disease, primary hypertention, hyperlipidemia, heart failure, myocardial fibrosis, myocarditis, viral myocarditis, primary cardiomyopathy, dilated cardiomyopathy, hypertrophic cardiomyopathy, constrictive cardiomyopathy, rheumatic heart disease, rheumatic heart valve disease, infectious endocarditis, congenital heart disease, arrhythmia, auricular fibrillation, ventricular tachycardia, ventricular flutter, ventricular fibrillation, Adame-Strokes syndrome, heart and kidney reperfusion injury, transient ischemic attack (TIA), cerebral apoplexy, epilepsy, dementia, cerebral hemorrhage, subarachnoid hemorrhage, cerebral infarction, cerebral aneurysm and cerebral arteriovenous malformation.

The inventor has found that rapamycin increases the expression quantity of ADRB3 in a vascular endothelial cell and a smooth muscle cell, which causes the restenosis of the rapamycin after drug eluting stenting. The present invention discloses that the ADRB3 antibody treats the restenosis and the in-stent restenosis after coronary artery intervention operation. The ADRB3 antibody is used as a coating drug for producing new drug eluting stent and eluting balloon.

The present invention discloses that the soluble ADRB3 is used as a new index to diagnose acute coronary syndrome and predict the prognosis of angiocardiopathy. The measurement of the soluble ADRB3 can be used as a molecular marker of early diagnosis of coronary heart disease, the increase of the soluble ADRB3 level is a dangerous factor of the coronary heart disease, with the increase of ADRB3 level in the blood, the onset risk of ACS is obviously increased, and the diagnosis of angiocardiopathy becomes bad. The soluble ADRB3 level in peripheral blood of the patient with acute coronary syndrome is higher than that of the patient with stable angina pectoris, the soluble ADRB3 level in the blood is an important indicator to diagnose ACS, and the ADRB3$^+$ granulocyte and ADRB3$^+$ lymphocyte count can both be increased.

The present invention discloses that the anti-human ADRB3 monoclonal antibody is a broad-spectrum anti-inflammatory drug and immunoinhibitants, can relieve the inflammatory reaction of the whole body and the tissue damage, and is used for treating inflammatory disease, anaphylactic disease and autoimmune disease, which include but are not limited to: upper respiratory infection, bronchitis, pneumonia, emphysema, asthma, glucocorticoid-resistant asthma, eosinophilia, idiopathic eosinophilia syndrome, allergic rhinitis, interstitial pneumonia, lung interstitial fibrosis, chronic obstructive pulmonary disease, primary pulmonary hypertension, connective tissue disease-related pulmonary hypertension, pulmonary fibrosis, idiopathic pulmonary fibrosis and cystic fibrosis, pulmonary sarcoidosis, silicosis, lung injury, acute respiratory distress syndrome, respiratory failure, pleurisy, tuberculosis, endotoxemia, septic shock, toxic shock syndrome, sepsis, pyaemia, septic shock, endotoxin shock, anaphylactic shock, multiple organ dysfunction syndrome, disseminated intravascular coagulation, burns, acute severe hepatitis, acute liver failure, chronic hepatitis, viral hepatitis, cirrhosis, hepatic encephalopathy, primary sclerosing cholangitis, autoimmune hepatitis, primary biliary cirrhosis, cholecystitis, pancreatitis, chronic gastritis, peptic ulcer, digestive tract stress ulcer, stress gastrointestinal bleeding, diabetes, eczema, contact dermatitis, neurodermatitis, encephalitis, meningitis, myelitis, Guillain-Barre syndrome, multiple sclerosis, glaucoma, infectious polyneuritis, optic neuritis, optic papilla, diabetes retinopathy, iridocyclitis, uveitis, sympathetic ophthalmia, retinal vein occlusion, neuromyelitis optica, demyelinating disease, conjunctivitis, keratitis, scleritis, dry eye, cataracts, macular degeneration, age-related macular degeneration, tetanus, condyloma *acuminatum*, gonorrhea, genital herpes, syphilis, psoriasis, *pityriasis simplex*, vitiligo, xeroderma pigmentosum, nevus of ota, melasma, herpes zoster, tinea cruris, tinea manus and pedis, eczema, anaphylactic dermatitis, acne, seborrheic dermatitis, alopecia, seborrheic alopecia, mental alopecia, alopecia areata, neuropathic alopecia, presenile poliosis, rheumatoid arthritis, osteoarthritis, osteoporosis, systemic lupus erythematosus, systemic scleroderma, sarcoidosis, ankylosing spondylitis, dysentery, inflammatory bowel disease, Crohn disease, ulcerative colitis, irritable bowel syndrome, sicca syndrome, gout, mixed connective tissue disease, myasthenia gravis, visceral leishmaniasis, Chagas disease, amoebic liver abscess, pediatric mucocutaneous lymph node syndrome, vasculitis, systemic vasculitis, primary small vasculitis, granulomatous vasculitis, thromboangiitis obliterans, paroxysmal nocturnal hemoglobinuria, giant cell arteritis, endocapillary proliferative glomerulonephritis, mesangial capillary glomerulonephritis, lupus nephritis, glomerulonephritis, tubular atrophy and interstitial fibrosis, pyelonephritis, nephritis nephrotic syndrome, renal failure, polycystic kidney, urinary tract infection, pelvic infection, salpingitis, prostatitis, multiple sclerosis, Behcet disease, pemphigus, pemphigoid, dermatomyositis, cellulitis, acute purulent meningitis, malaria, Alzheimer disease, dementia with Lewy bodies, Parkinson disease, amyotrophic lateral sclerosis, multiple cerebrospinal sclerosis, acute idiopathic polyneuritis, Kawasaki disease, thyroiditis, Hashimoto thyroiditis, primary myxoedema, hyperthyroidism, graft-versus-host disease, allograft rejection, myopathy, muscle degeneration, muscular dystrophy, ataxia telangiectasia, chronic granulomatosis, lymphadenitis, aplastic anemia, autoimmune hemolytic anemia, anaphylactoid purpura, thrombocytopenic purpura, myelofibrosis, myelodysplastic syndrome, leukocyte adhesion deficiency, B cell deficient disease, T cell deficient disease, severe combined immunodeficiency disease, complement deficiency disease, lysosomal storage disease, mucopolysaccharide storage disease, mucolipidosis storage disease, *Helicobacter pylori* infection, Brucellosis, syphilis, leptospirosis, Brucellosis, toxoplasmosis, echinococcosis, schistosomiasis, typhoid fever, kala-azar, and filariasis.

The present invention discloses that the ADRB3 antibody has a reverse effect on the drug resistance of gonococcus, and is used for treating resistance gonorrhea.

The present invention discloses that soluble ADRB3 is used as a new index for predicting the prognosis of the inflammatory diseases above, and with the increase of ADRB3 level in blood, the prognosis becomes bad.

The ADRB3 promotes the duplication of human immunodeficiency virus, hepatitis virus, Ebola virus, adenovirus, influenza virus, papilloma virus, herpes simplex virus, EB virus and rabies virus. The ADRB3 antibody inhibits the duplication of the virus, and promotes the elimination of the virus. After infecting the cell, HIV induces ADRB3 originally distributed in endochylema to accumulate on a membrane, promotes CD4$^+$T be chemotactic, and enables T cell to adhere in the area rich in ADRB3. With the help of the synapse formed by ADRB3, HIV removes to a host cell-CD4 T cell.

The present invention discloses that the anti-human ADRB3 monoclonal antibody is a broad-spectrum antiviral agent used for treating virus infectious diseases, which include but are not limited to: severe acute respiratory syndrome, infectious atypical pneumonia, acquired immunodeficiency syndrome, viral hepatitis B and C, influenza, measles, verruca vulgaris, genital verruca (condyloma *acuminata*), human T-cell leukemia virus infection, neonatal herpes caused by herpes simplex virus infection, herpes progenitalis, viral meningitis, slow viral encephalitis and encephalopathy, human prion protein disease, Creuzfeldt-Jacob disease, Kuru disease, subacute sclerosing panencephalitis, viral myocarditis, hand-foot-and-mouth disease, EB virus infection, infectious mononucleosis, viral hemorrhagic fever, epidemic hemorrhagic fever, dengue hemorrhagic fever, Ebola hemorrhagic fever, herpes zoster, idiopathic thrombocytopenic purpura and hydrophobia.

Based on the antiviral effect of the ADRB3 monoclonal antibody, the present invention discloses that the ADRB3 gene is used for preparing preventive antiviral vaccine, and the ADRB3 overall-length protein and polypeptide fragment are used for preparing therapeutic antiviral vaccine, which induce the special cellular immunity and humoral immune response to reach the purpose of eliminating or controlling the virus.

The present invention discloses that the ADRB3 antibody activates an antigen presenting cell, stimulates T-cell immunologic response, and increases the immune effect of a vaccine. Before and after vaccinating, the ADRB3 antibody is given, which can increase the quantity of the antigen presenting cell, so as to effectively capture, process and present the antigen to T-cell. The antibody used as an immunologic adjuvant enhances the substance with weak antigenicity to induce the body to generate specific immunity response, increases the immunogenicity of genetic engineering vaccine, and is used for researching new genetic engineering vaccines of hepatitis B, influenza virus and HIV. The antibody can also be used for producing and researching antitoxic serums, which include but are not limited to the antitoxic serums of snake, epidemic encephalitis B, tetanus and rabies antitoxic serum.

The present invention discloses that the ADRB3 antibody inhibits various rejection reactions occurring to the immune system after organ transplantation, and is used for preventing and treating the rejection reaction after organ transplantation.

According to the proteins in the ADRB3 signaling pathway, the present invention discloses that the ADRB3 antibody is used for treating the diseases related to P62, HK2, GAPDH, VEGF, Cyclin D1, CDK3, CDK4, Rb, Ki-67, mTOR, Rictor, AKT, Tubulin, TRAF6, PD-L1, P53, P63, IL-2, IL-6, IL-10, TGF and TNF signaling pathways.

The present invention discloses that the ADRB3 antibody inhibits the proliferation of primitive granulocytes promyelocytes and myelocytes, promotes the apoptosis of CD4$^+$T cells, Treg and myeloid-derived suppressor cells, reduces the infiltration of granulocytes, macrophages and lymphocytes in tissues, and relieves the damage of tissues caused by inflammatory reaction, and the damage of tissues is the basis of the occurrence of senility, organ failures and malignant tumors.

The present invention discloses that the ADRB3 antibody can increase the tolerance of the body to bacterial endotoxin, and has good effect of bringing down a fever and relieving toxaemia. The ADRB3 antibody is used for treating severe injury, pyaemia, endoxemia, infectious shock, and multiple organ dysfunction syndromes. The ADRB3 antibody treats acute pyogenic infection, such as abscess, pneumonia, appendicitis, erysipelas, bacteremia, organic perforation, scarlatina, etc.

On the basis that ADRB3 participates in regulating the genetic expressions of a solute carrier superfamily and an ATP-binding cassette superfamily, the absorption, distripution, elimination and other processes of the drug and toxic substance are affected. The present invention discloses the ADRB3 antibody treats the poisonings, such as acidosis, hyperlactacidemia, uremia, organophosphorus poisoning, alcoholism, barbital poisoning, heavy metal (lead, mercury, arsenic, thallium, etc.) poisoning, bacterial toxin (tetanus toxin, diphtheria toxin, botulinus toxin, etc.) poisoning, etc. The soluble ADRB3 is used as a new index to predict the prognosis of the poisoning diseases above, the ADRB3 level in the blood is increased, and the prognosis becomes bad.

The present invention discloses that the ADRB3 antibody inhibits an mTOR signal, and more particularly, inhibits the activity of mTORC1 (mammalian target of rapamycin complex 1), which is used for treating the disease related to senility and anti senility. The mTORC1 protein in hypothalamus is a key factor to control the blood pressure, the excessive activation of mTORC1 leads to the increase of blood pressure, and the ADRB3 antibody inhibits mTORC1 to play a role of decreasing the blood pressure.

A synapse is a part where two nerve cells or a nerve cell and an effector cell are contacted with each other and thus deliver messages. Synapse function inhibition and synapse loss are related to the decrease of cognitive ability. On the early stage of Alzheimer disease, ADRB3 inhibits the signal transduction between the synapses, which is shown as recent hypomnesis. The inventor has found that in the cerebrospinal fluid of the patient with Alzheimer disease, the concentration of the soluble ADRB3 is higher than the normal level, which causes neuroinflammation and leads to the memory degradation of the patient. The ADRB3 antibody can reverse the loss of memory seen in Alzheimer disease.

A microglia is an immunocyte in a central nervous system to eliminate damaged nerves, plaque and infectious substance in the central nervous system. ADRB3 is expressed in the microglia, an ADRB3 signaling pathway with normal activity promotes the proliferation of the microglia, maintains the function of the microglia, increased nerve growth factors, and promotes the nervous tissue regeneration. Under a pathologic condition, active ADRB3 signaling pathway can excessively activate the microglia, which causes that the microglia is dedifferentiated to lose the function thereof, so as to lead to neurovirulence, weaken the synaptic plasticity of a nerve cell, and plays an important role in the pathogenesis of neurodegeneration disease. The present invention discloses that the anti-human ADRB3 monoclonal antibody can increase the learning and memory ability, promote the nerve regeneration, and treat the nerve diseases, which include but are not limited to: Alzheimer disease, Parkinson's disease, multiple sclerosis, amyotrophic lateral sclerosis, epilepsy, ataxia telangiectasia, Guillain-Barre syndrome, bovine spongiform encephalopathy, Creutzfeldt-Jakob disease, Huntington's disease, hepatolenticular degeneration, tourette syndrome, fragile X chromosome, Lambert Eaton myasthenic syndrome, acquired neuromyotonia, limbic encephalitis, autoimmune encephalitis, anti-NMDA receptor encephalitis, ophthalmoneuromyelitis, hashimoto encephalopathy, lupus encephalopathy, viral encephalitis, extrapyramidal disease, acute hemorrhagic leukoencephalitis, diffuse sclerosis, demyelinating disease, cerebellar atrophy, primary lateral sclerosis, spinal muscular atrophy, paraplegia, spinal cord injury, syringomyelia, myelitis, etc.

The present invention discloses that the ADRB3 antibody depresses the inflammatory reaction of a nervous system, and relieves the anxiety or depression caused under a pressure state. The ADRB3 antibody is used for treating mental diseases, which include but are not limited to: schizophrenia, schizoaffective disorder, paranoiac psychosis, psychogeny caused by epilepsy, bipolar affective disorder, depression, infantile autism, obsessive-compulsive disorder, anorexia nervosa, bulimia nervosa, panic disorder, borderline personality disorder, infective psychosis, psychosis caused by physical disease, toxic psychosis (carbon monoxide poisoning and pesticide poisoning), Alzheimer disease, alcoholic psychosis, brain traumatic psychosis, neurosis, chronic fatigue syndrome, etc.

The present invention discloses that the ADRB3 antibody is used for treating the habituation caused by ethyl alcohol and narcotic drug (such as heroin, methylamphetamine, morphine, marihuana, cocaine, etc.)

ADRB3 plays a key role in the process of bone remodeling, and ADRB3 expresses and regulates bone resorption in an osteoclast. ADRB3 gene knockout can increase the sclerotin of mice. The present invention discloses that the ADRB3 antibody can inhibit the osteoclast, promotes bone formation, and is used for treating the disease related to bone retrogression, the bone retrogression include osteoporosis, osteoarthritis, degenerative arthritis, delayed union or disunion of fracture, femoral head necrosis, slipped capital femoral epiphysis, collum femoris abnormity, dysplasia epiphysalis multiplex, old fracture, suppurative arthritis, osteomyelitis, gout, chondrocalcinosis, etc.

The anti-human ADRB3 monoclonal antibody generated by different hybridoma cell strains in the present invention has different functions, the antibody generated by some hybridoma cell strains such as 5B8 and 5D1 can retard ADRB3 and reduce the activity of ADRB3. The antibody generated by some hybridoma cell strains such as 4G7 and 4F7 can stimulate ADRB3 and increase the activity of ADRB3. The ADRB3 antibody with the function of stimulating ADRB3 and the agonist such as BRL37344 can maintain the undifferentiation state of the stem cell, are added in a culture medium to cultivate stem cell, embryonic stem cell and hematopoietic stem cell, and can further be used for producing and cultivating induced pluripotent stem cell.

The ADRB3 antibody can be used for coating a cell culture plate, which is used for cultivating the lymphocyte. The antibody can be used for preparing immunomagnetic bead cell sorting reagent, enzyme-linked immunosorbent assay (ELISA) reagent, fluorescence coupling antibody, HRP coupling antibody, or other tag protein coupling antibodies.

Except for a cytomembrane, the ADRB3 protein further exists in the cytoplasm and the cell nucleus. Most ADRB3 in the tumor cell are located in the cell nucleus, ADRB3 in the neutrophils is mainly located in the cytoplasm, the antigenic epitopes exposed by ADRB3 with different locations are different, and the same antibody has different affinity with ADRB3 with different locations. The present invention discloses that the antibody generated by the use of N end of the ADRB3 protein and middle fragment polypeptide immune animal is easy to be combined with ADRB3 of the tumor cell, and the antibody can be used for marking the tumor cell. The antibody generated by polypeptide fragment immunity of C end of the ADRB3 protein is easy to be combined with ADRB3 in the granulocyte cytoplasm, and the antibody can be used for marking the granulocytes.

The present invention discloses that the ADRB3 gene is used for preparing preventive tumor vaccine, ADRB3 overall-length protein and polypeptide fragment are used for preparing therapeutic tumor vaccine, which induces the special cellular immunity and humoral immune response to reach the purpose of eliminating or controlling the tumor. The present invention discloses the capability of the ADRB3 antibody of increasing the plasmocyte to generate the antibody.

The present invention discloses that the recombination fusion protein of the ADRB3 monoclonal antibody and other tumor or virus specific antigens is prepared to induce antineoplastic and antiviral immune response. Other tumor or virus specific antigens include but are not limited to: human prostate-specific antigen (PSA), prostatic acid phosphatase (PAP), alpha fetoprotein, carcino-embryonic antigen, mutational ras gene encoding protein, c-myc gene product, glycoprotein antigen (CA) 50, CA1523, CA7224, CA549, cytokeratin 19, squamous cell-related antigen (SCC), C-reactive protein, PD-1, PD-L1, HIV protein, hepatitis B and C virus protein, etc.

The present invention discloses that the ADRB3 monoclonal antibody is used to reduce overactive ADRB3 in blood, ascites or other body fluids in the combination of plasmapheresis, hematodialysis, peritoneal dialysis and other technologies to treat inflammation, pyaemia, tumor, heart failure and cachexia. Reducing ADRB3 in the blood of the aged can delay the senility. The ADRB3 antibody is used to adsorb the neutrophils, lymphocyte, MDSC, Treg and M2-type mononuclear cell in blood, hydrothorax, ascites and other body fluids of the patient, and the immune adsorption treatment is treated to treat the adaptation disease with the adaptation disease equivalent to the ADRB3 monoclonal antibody.

In the case that ADRB3 with normal activity promotes the regeneration, under the condition that the ADRB3 activity is low, the tissue regeneration is promoted by appropriately increasing ADRB3 content and activity in blood, cerebrospinal fluid, heart, brain, peripheral nerve, spinal cord, liver, pancreas, kidney, muscle and other tissues, which is used for treating the disease related to senility and the damage caused external injury, such as paraplegia. However, under the condition of sthenic ADRB3 activity, the regeneration shall be promoted by reducing the antibody of ADRB3 activity.

The reproductive tract infectious disease is related to infertility, and the seminal plasma ADRB3 detection is a special index of male reproductive tract infectious disease. The inventor has found that the fecundity of aged ADRB3 knockout mice is stronger than that of normal aged mice, and the born number of mother mice given with the ADRB3 antibody is more than that of normal mother mice. The ADRB3 antibody reduces seminal plasma elastase level of father mice, and the ADRB3 antibody is prompted to inhibit the reproductive tract infectious disease. The result of ChIP-chip prompts that ADRB3 regulates a lot of genes related to ovum and sperm activity, such as IZUMO1, TSSK3, TSSK6, TSKS and other expressions. The ADRB3 antibody can strengthen the ovum and sperm activity, and can be used for treating infertility, erectile dysfunction, premature ejaculation and sexual dysfunction.

On the basis that ADRB3 increases the elastase activity, the present invention discloses that the ADRB3 antibody is used for preparing skin care cosmetics with the effects of delaying skin aging, recovering skin elasticity, reducing wrinkle and reducing chromatosis.

Compared with the prior art, the present invention has the following beneficial effects.

The present invention makes clear that ADRB3 is a key receptor in a nerve-internal secretion-immunoregulation system, ADRB3 mediates various signaling pathways, and the mediated signaling pathways regulate the proliferation and differentiation of neutrophils, lymphocytes and tumor cells. Normally, ADRB3 maintains nonspecific immunity and specific immunity capability of the organism, and eliminates exogenous pathogenic microorganism and aged organism tissues to play a role of protecting the organism and preventing senility. Under a pathologic condition, the overactivity of the signaling pathway will lead to systemic chronic inflammation and damage immunity homeostasis. Since the ADRB3 monoclonal antibody can be specifically bonded, and regulate (retard or stimulate) the ADRB3 activity, the ADRB3 monoclonal antibody can be used for treating inflammation, malignant tumor, virus infection, cardiovascular and cerebrovascular diseases (such as atherosclerosis), diabetes, neurodegenerative disease (such as Alzheimer disease), autoimmune disease, senile disease, pyaemia, asthma, endotoxemia, infectious shock, multiple organ dysfunction syndrome, acute suppurative infection, the disease caused by regeneration dysfunction, gonococcal infection, anemia, severe injury, anaphylactic disease, cachectic disease, toxic disease, immunological rejection of organ transplantation, cachectic disease, pulmonary arterial hypertension, acute coronary syndrome, bone retrogression, hypertrophic cardiomyopathy, MDSC-related disease, mental disease, and other diseases, and has significant medical values and application prospects.

BRIEF DESCRIPTION OF THE DRAWINGS

FIG. 32: bone marrow smears of patients with acute monocytic leukemia (M5) after CR by treatment are stained with ADRB3 and MPO.

FIG. 33: bone marrow smears of patients with acute myelocytic leukemia after CR by treatment are stained with ADRB3 and Ki-67; and ADRB3 is highly expressed in granulocytes in proliferation phase (Ki-67 positive).

FIG. 34: A. different ADRB3 polypeptides used to immunize mice; and B. detect the antibody specificity with Western blot.

FIG. 35: nucleic acid and protein sequence of a light chain antibody.

FIG. 36: nucleic acid and protein sequence of a heavy chain antibody.

there are a lot of soluble ADRB3 (soluble B3, sB3) in the hydrothorax of lung cancer patients, suggesting that granulocytes release sB3 into blood and tissue spaces by degranulation; B. there are a lot of ADRB3 in granulocyte cytoplasm; C/D. granulocytes (MPO$^+$) with high expression of ADRB3 in the hydrothorax tend to be adhered to lung cancer cells; and E. The ADRB3 is highly expressed in exfoliated lung cancer cells of the hydrothorax.

Figure 83:
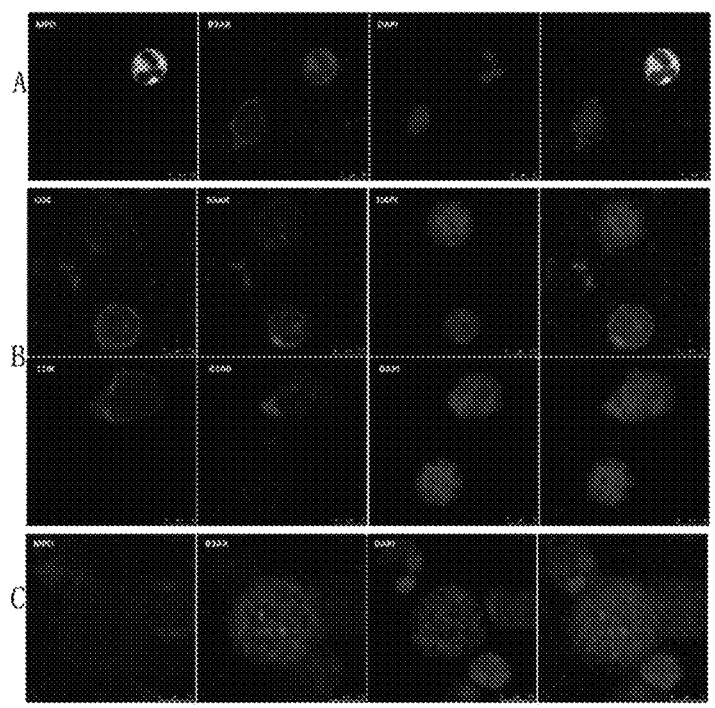

FIG. 83: immunofluorescence detection of the ADRB3 expression in peripheral blood smear cells of normal subjects; A. ADRB3 is expressed in normal neutrophils, and is slightly expressed in lymphocytes; B. ADRB3 is abundantly expressed in naive or primitive T-lymphocytes (cytoplasm containing large amounts of CD4 or CD8 lymphocytes); C. ADRB3 is highly expressed in cells at late G2 phase and early mitosis. In this phase, the karyotheca has been ruptured, and the chromosome replication has been completed, but the spindle has not yet been formed.

Figure 84:
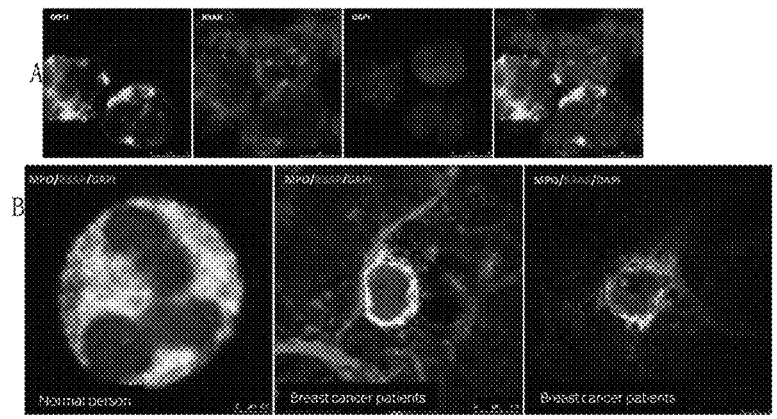

FIG. 84: A. immunofluorescence of ADRB3 in peripheral blood smears of breast cancer patients, there are a lot of ADRB3 in granulocytes and abnormal lymphocytes (upper right), ADRB3 is abundantly expressed, the cytoblast has granulocyte-like changes; and B. there are a large number of foot processes in the granulocytes of breast cancer patients, and ADRB3 is adhered to the foot process.

Figure 85:
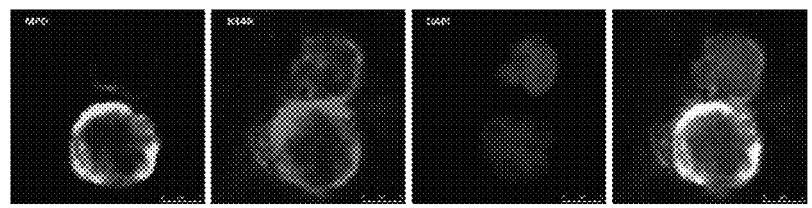

FIG. 85: immunofluorescence of ADRB3 in peripheral blood smears of breast cancer patients; high expression of ADRB3 and microexpression of MPO in the upper lymphocytes; in the lower granulocytes, a lot of ADRB3 are accumulated in the contact position between granulocytes and lymphocytes, which plays a role like adhesion factors, and promotes to form immune synapses. Granulocytes induce lymphocytes to differentiate toward myeloid cells.

Figure 86:
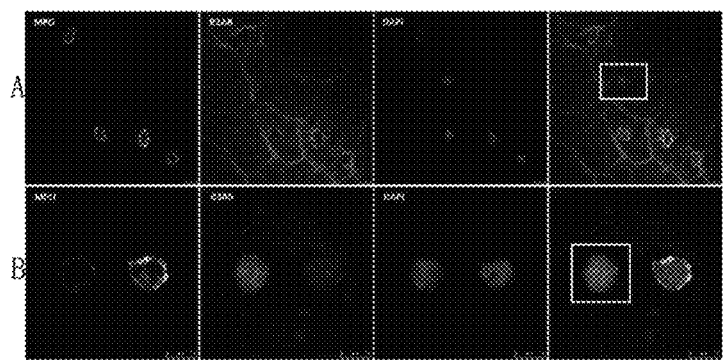

FIG. 86: immunofluorescence of ADRB3 in peripheral blood smears of breast cancer patients; A. a large number of neutrophils extracellular networks (NET) are formed in the blood of breast cancer patients, and the lymphocytes (MPO negative) are adhered to the NETs; B. the lymphocytes in the yellow box are reflected as MPO$^{dim}$ADRB3$^{bright}$, which may be lymphocyte progenitor cells or primitive lymphocytes.

Figure 87:
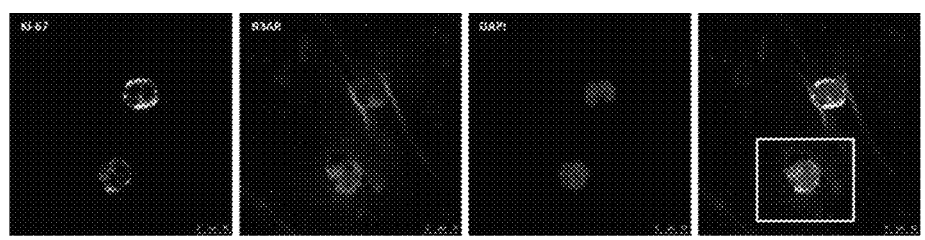

FIG. 87: ADRB3 and Ki-67 are highly expressed in lymphocytes (in yellow box) of the blood of breast cancer patients, are in the proliferation phase, are dedifferentiated, and are naive or primitive lymphocytes, indicating that the patients have lymphocyte hypofunction and specific immunodeficiency.

Figure 88:
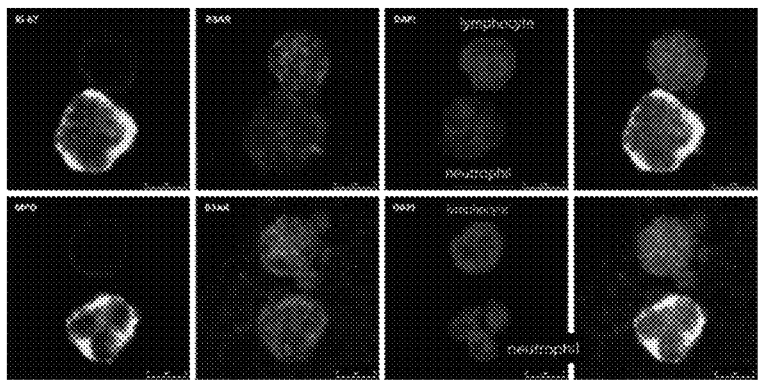

FIG. 88: ADRB3 is highly expressed, and Ki-67 and MPO are less expressed in a part of lymphocytes of breast cancer patients, which are naive or primitive lymphocytes.

Figure 89:
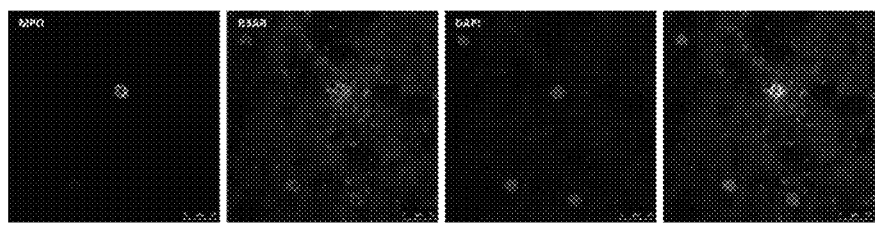

FIG. 89: there are a large number of DNA fragments in the blood of breast cancer patients, and the ADRB3 is adhered to the DNA fragments.

Figure 90:
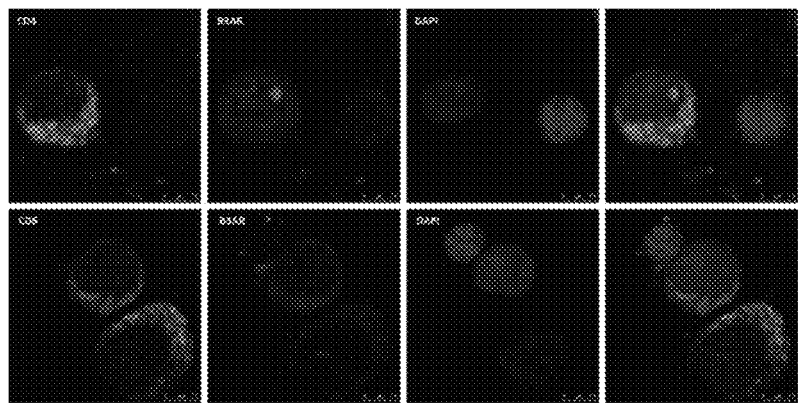

FIG. 90: immunofluorescence detection of ADRB3 in cells of peripheral blood smears of normal subjects—the cytoblast of the primitive plasmocyte is larger than that of the T cell, and there are a lot of ADRB3 in the cytoplast.

Figure 91:
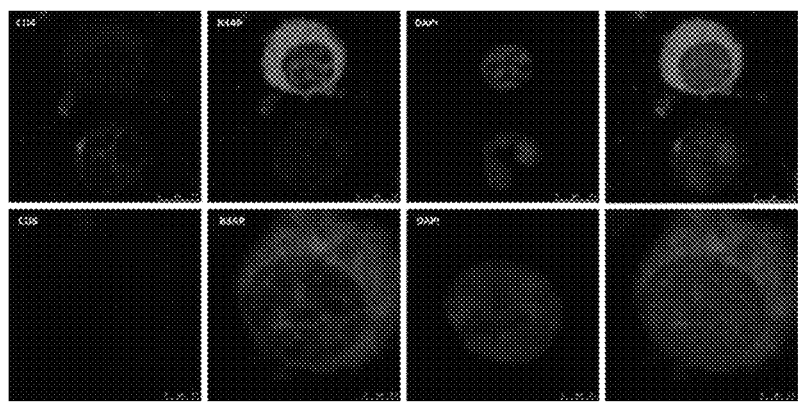

FIG. 91: immunofluorescence detection of ADRB3 in cells of peripheral blood smears of normal subjects-mature plasmocytes have the characteristics that there is no CD4 or CD8, but a lot of ADRB3 in the cytoplasm.

Figure 92:
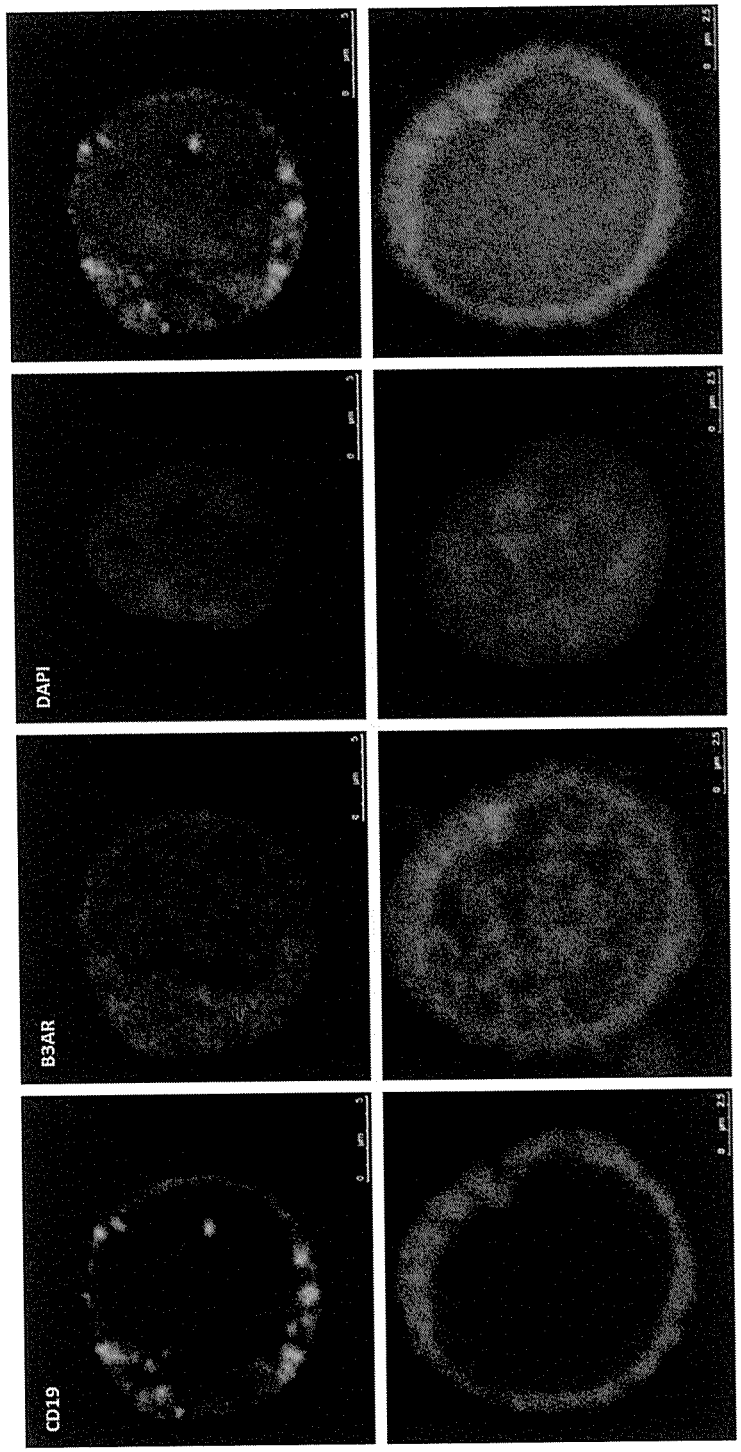

FIG. 92: immunofluorescence detection of ADRB3 in cells of peripheral blood smears of normal subjects—ADRB3 is expressed in the cell membrane of CD19$^+$B.

Figure 93:
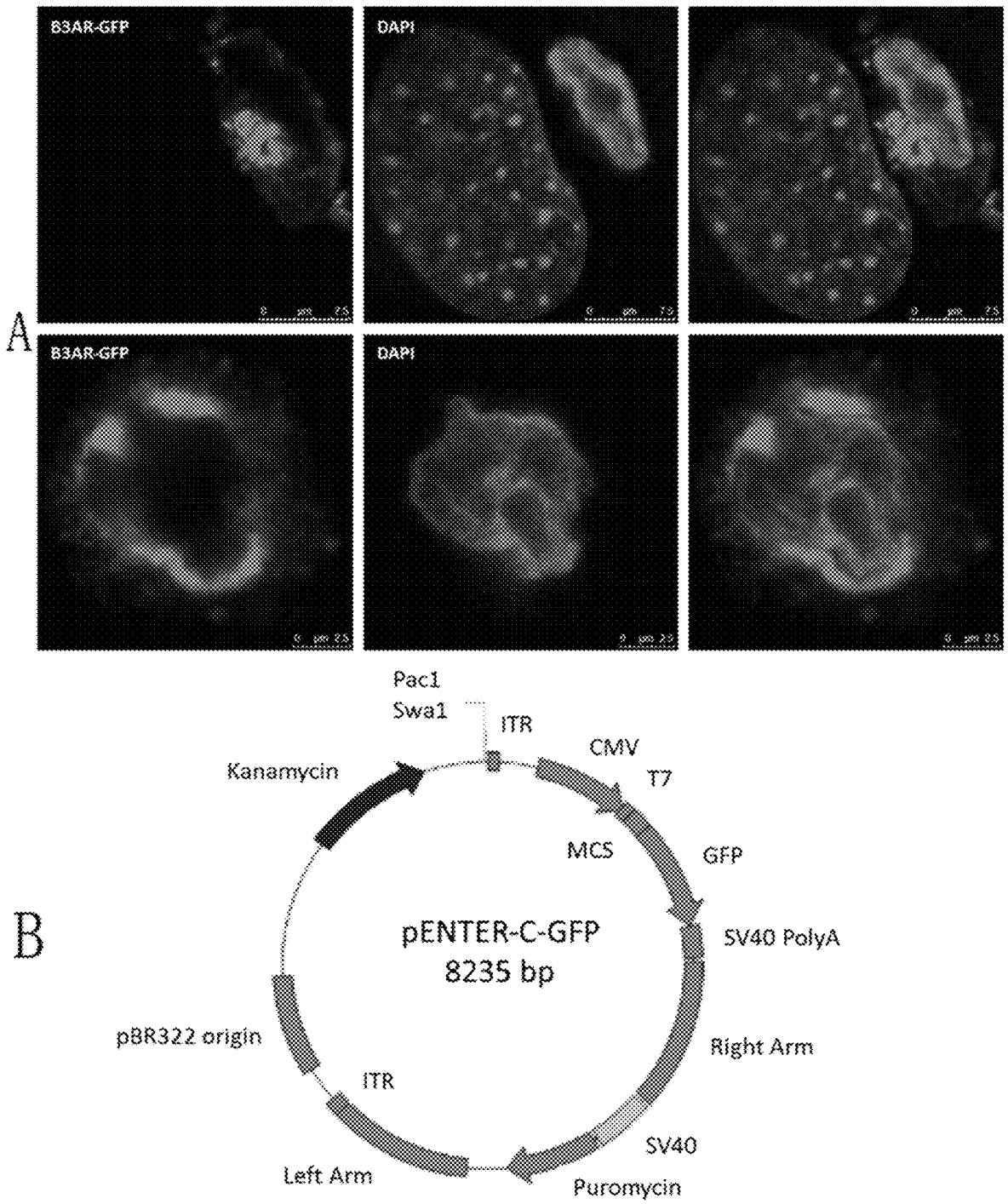

FIG. 93: A. ADRB3 carrying green fluorescent proteins (GFP) can kill pancreatic cancer cell SW1990; B. ADRB3 plasmid diagram.

Figure 94:
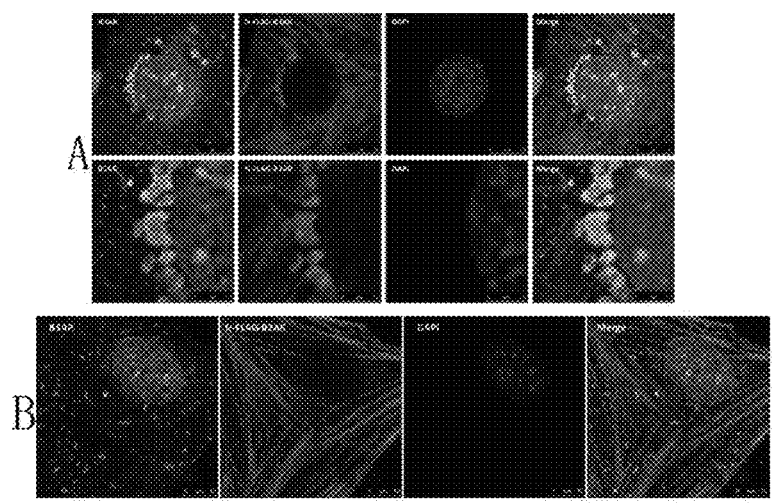

FIG. 94: A. ADRB3 carrying Flag tag proteins cannot enter the cytoblast of MCF7; B. ADRB3 is localized in microtubules, cytoblasts and mitochondria of MCF7 cells.

Figure 95:
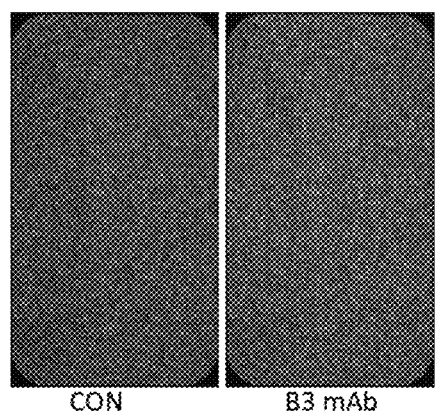

FIG. 95: ChIP-Chip experimental chip scannogram.

Figure 96:
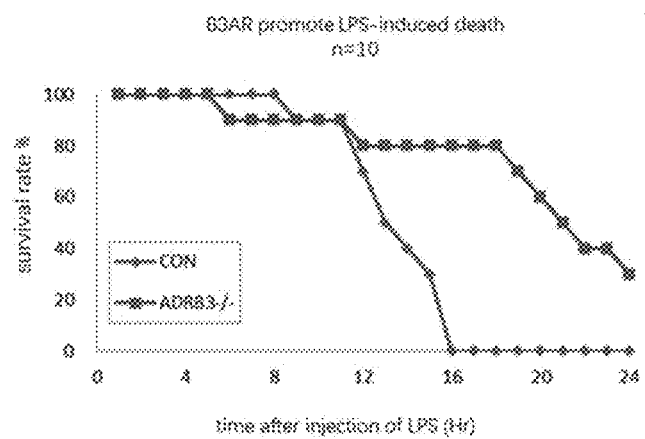

FIG. 96: survival curve of mice in each group after ADRB3 knockout mice and normal mice are intraperitoneally injected with 30 mg/kg LPS; and the pyohemia mortality in ADRB3$^{-/-}$ mice is decreased.

Figure 97:
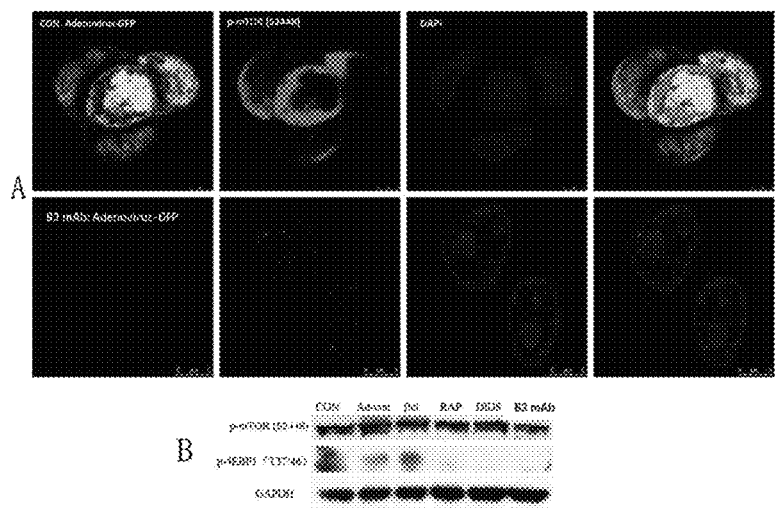

FIG. 97: after ADRB3 is inhibited, adenovirus is unable to infect lung cancer cell A549, and the ADRB3 antibody plays a role in inhibiting adenovirus infection by inhibiting phosphorylation of 2448th serine of mTOR; A. the upper figures show adenovirus infected cells, p-mTOR (Ser2448) is significantly increased and accumulated below cell membrane, and the lower figures show cells pretreated with the ADRB3 antibody without adenovirus infection; B. and the ADRB3 antibody inhibits p-mTOR (Ser2448), and reduces phosphorylation of downstream substrate 4EBP1 of mTOR.

Figure 98:
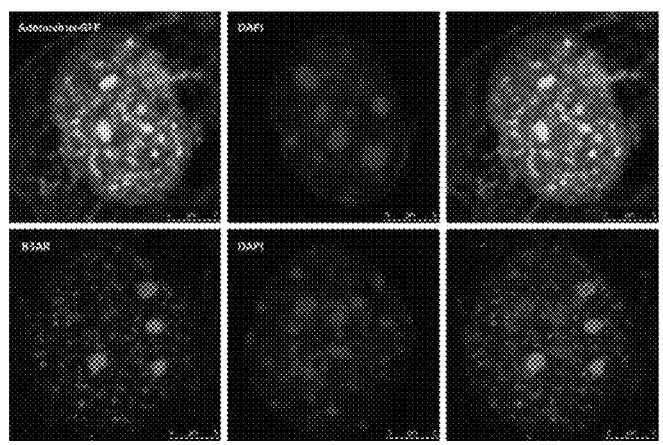

FIG. 98: both the ADRB3 and adenovirus are localized in nucleolus, and the ADRB3 is a key protein required for viral replication.

Figure 99:
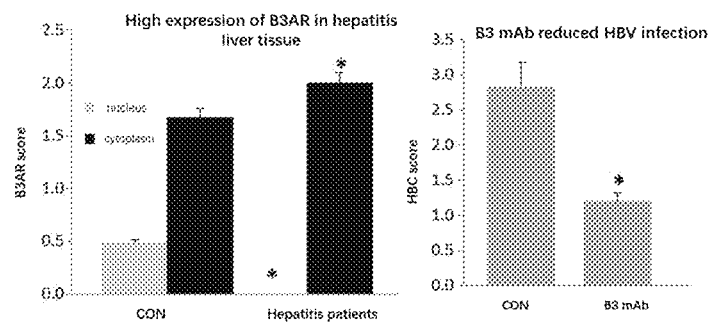

FIG. 99: the ADRB3 is increased in hepatocyte cytoplasm of patients with hepatitis B, and the ADRB3 antibody inhibits HBV infection of HepG2 cells.

Figure 100:
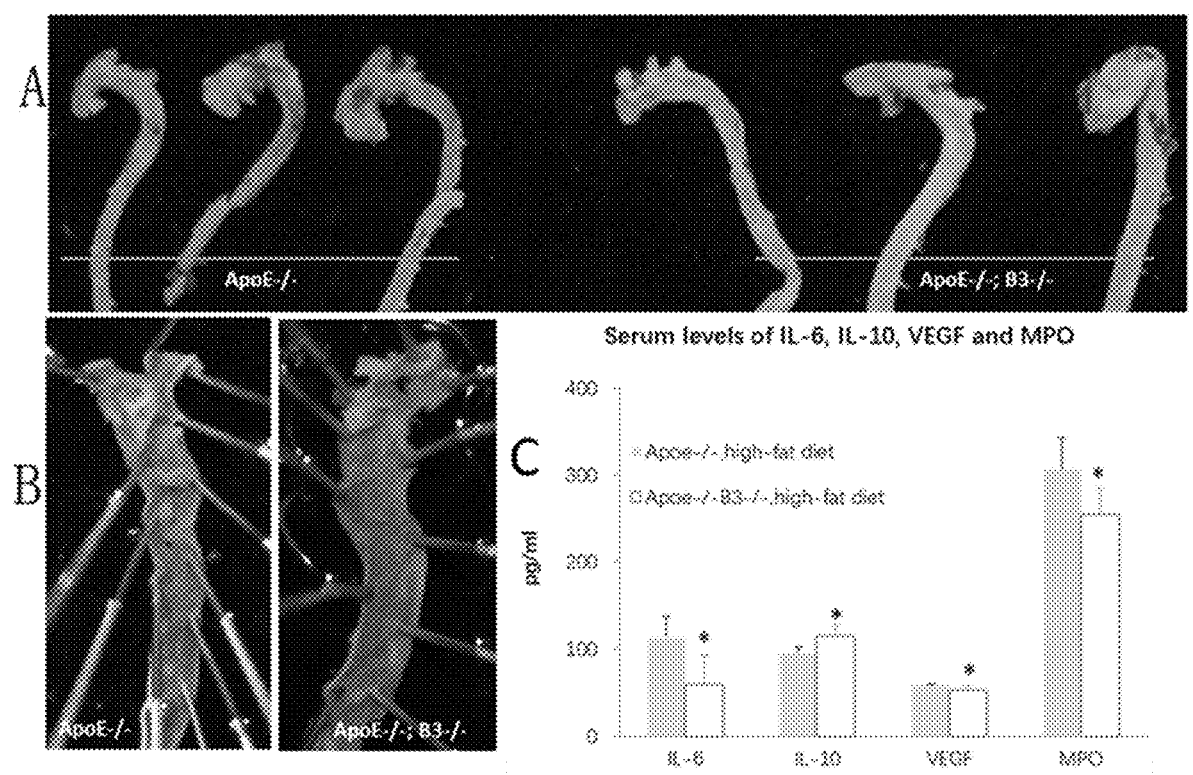

FIG. 100: atherosclerotic plaque detection of ADRB3/ApoE double knockout mice and ApoE knockout mice; A. the aorta of ADRB3/ApoE double knockout mice is significantly thickened than that of ApoE$^{-/-}$ mice; B. the aorta is stained with oil red O; and C. ELISA of inflammatory factor in serum.

Figure 101:
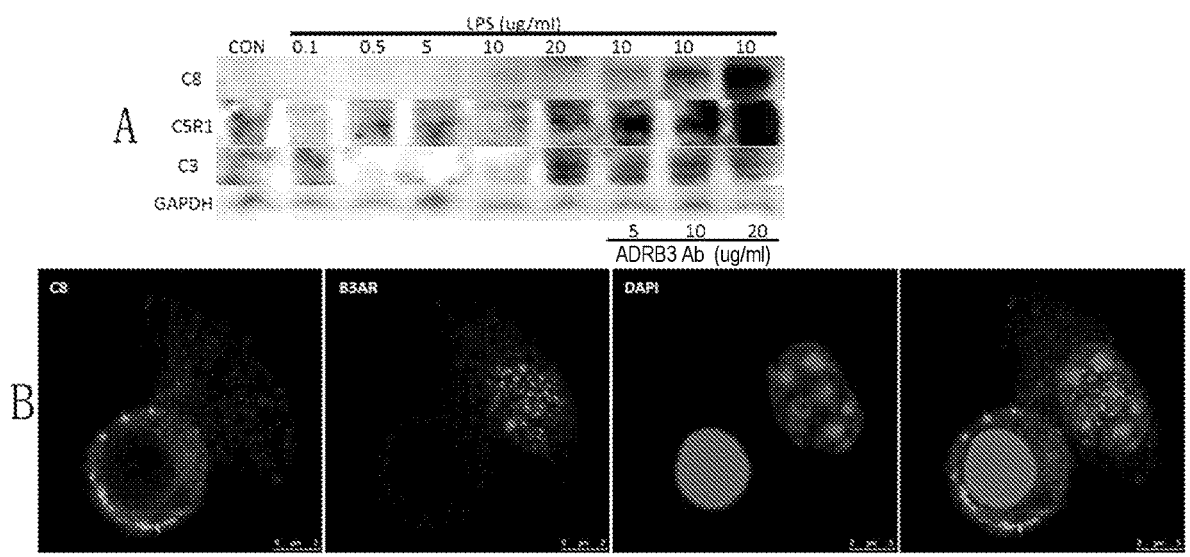

FIG. 101: the ADRB3 antibody promotes complement activation; A. the ADRB3 antibody increases the complements C8 and C5R1; LPS is an endotoxin as a positive control for inducing complements; and B. immunofluorescence detection of C8 and B3AR.

Figure 102:
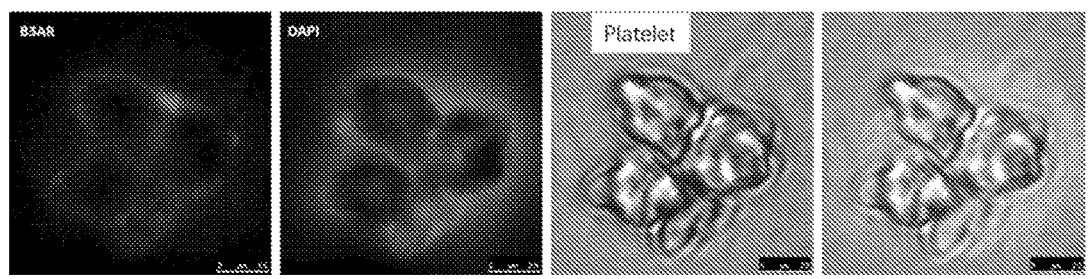

FIG. 102: the ADRB3 is located on the membrane of the platelet.

Figure 103:
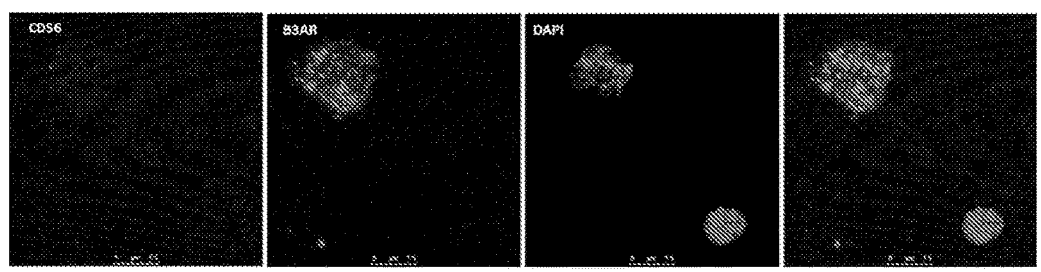

FIG. 103: ADRB3 and CD56 are expressed in NK cells of the umbilical cord blood.

Figure 104:
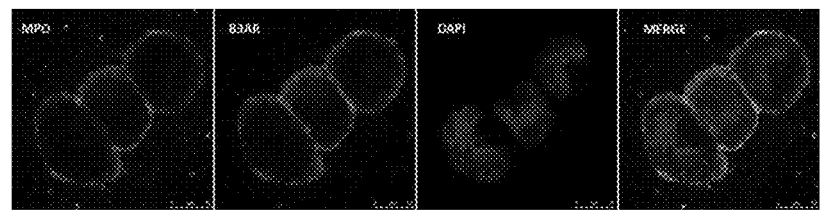

FIG. 104: ADRB3 and MPO are expressed in NK92 cells.

Figure 105:
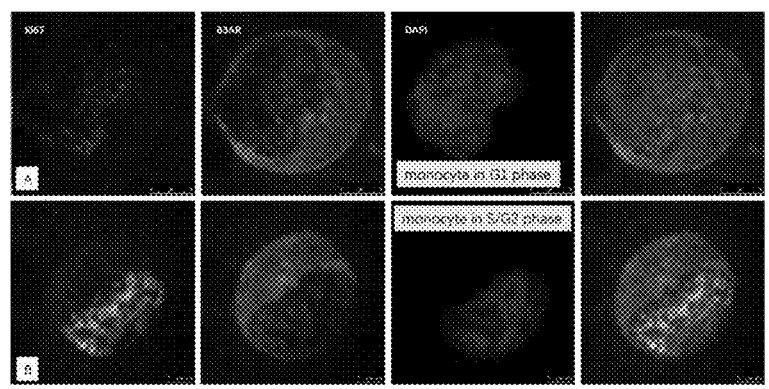

FIG. 105: the ADRB3 and Ki67 are expressed in monocytes of patients with acute myocardial infarction. (A) shows cells in G1 phase with less Ki67. (B) shows G2 or S phase with more Ki67.

Figure 106:
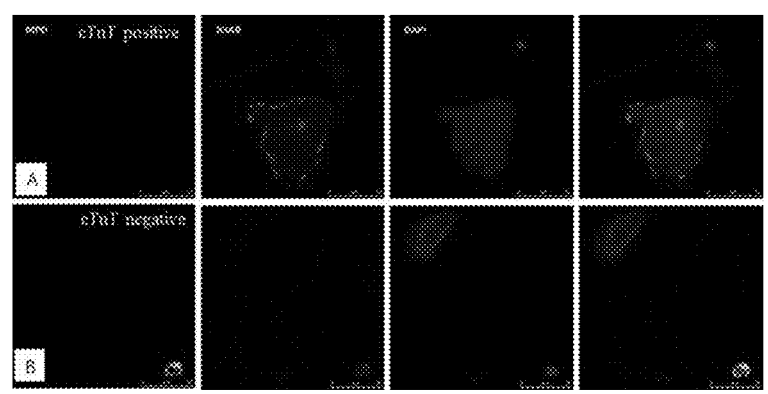

FIG. 106: in patients with acute coronary syndrome, the ADRB3 content in megakaryocytes of patients with positive cardiac troponin T (cTnT) is higher than that in megakaryocytes of patients with negative cTnT. (A) shows positive cTnT, and (B) shows negative cTnT.

DETAILED DESCRIPTION

The invention is further illustrated in detail in conjunction with the accompanying drawings and examples below. These examples are only used to illustrate the invention, rather than to limit in any way the scope of the invention.

Unless otherwise specifically indicated, the test methods used in the following examples are conventional methods; and unless otherwise specifically indicated, the materials, reagents, etc. are commercially available reagents and materials.

Example 1 Immunofluorescence for Localization of ADRB3 in Tumor Cells

1. Test Method

Breast cancer cell MCF7, lung cancer cell A549, melanoma A375, pancreatic cancer cell CFPAC1, hepatic cancer cell HepG2 and glioma cell A172 were inoculated into a 6-well plate with a built-in sterile coverslip at a rate of $10^5$/well, incubated until the cells were adhered to the coverslip, immobilized with 4% paraformaldehyde for 10 minutes, and washed with PBS 3 times. After transparentizing with 0.1% TritonX-100 for 10 min, and closing with 3% BSA for 1 h, antibodies of Ki-67/ADRB3/Nucleolin/Fibrillarin/H3K9AC/Brdu/-tubulin/Flag etc. (1:100) were added dropwise. The mitochondria were stained with Mitotracker, the lysosome was stained with lysotracker, cells were administrated with Brdu before immobilization, and pcDNA3-flag-B3 plasmid was transfected into cells with lipofectin 3000. The coverslips were sealed in a wet box, and incubated in a refrigerator at 4° C. overnight. After rinsing with PBS for 5 min×3, and adding FITC-labelled secondary anti-rabbit (1:800) and PE-labelled secondary anti-mouse (1:800) dropwise, the coverslips were incubated at room temperature for 1 h, stained with 0.5 µg/ml DAPI for 3 min, rinsed with PBS for 5 min×3, sealed with 50% glycerol/PBS, and observed under a laser scanning confocal microscope. 5-7 fields were randomly observed and photographed, and the mean red fluorescence intensity and the mean green fluorescence intensity of cells were measured with software Fluorchem 8900.

2. Test Results

Figure 1:
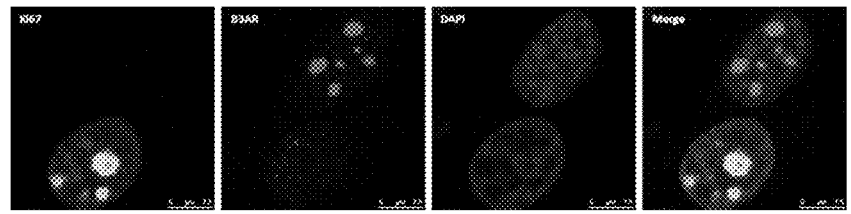
FIG. 1: high expression of an ADRB3 (B3AR) protein in the nucleolus of human breast cancer cell MCF7 at G0 phase (Ki-67 negative); an ADRB3 is also present in cytoblast of the cell (Ki-67 positive) in proliferation phase, but is rarely located in the nucleolus.
Figure 2:
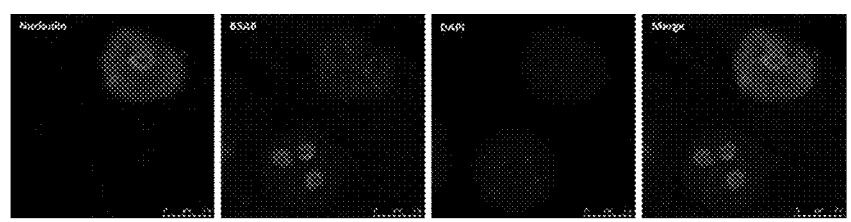
FIG. 2: high expression of an ADRB3 protein in the nucleolus of MCF7 cells at G0 phase (Nucleolin negative).
Figure 3:
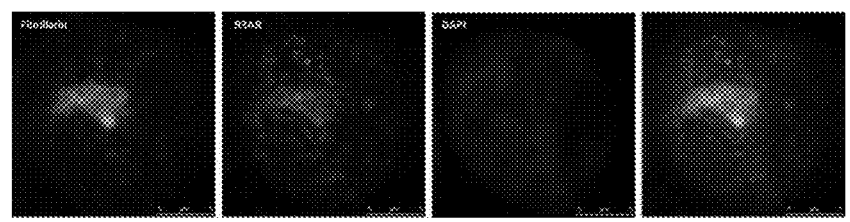
FIG. 3: high expression of an ADRB3 protein in the nucleolus (Fibrillarin positive) of the MCF7 cell.
Figure 4:
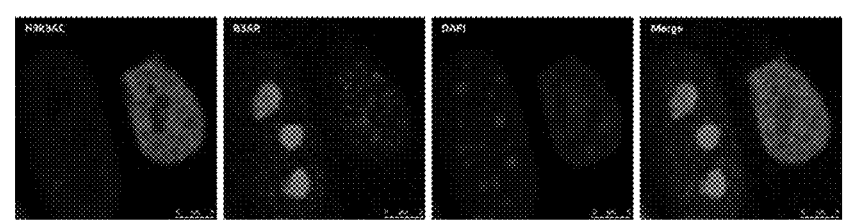
FIG. 4: nucleolus with an ADRB3 protein accumulated in the MCF7 cell (H3K9AC⁻) at G0 phase.
Figure 5:
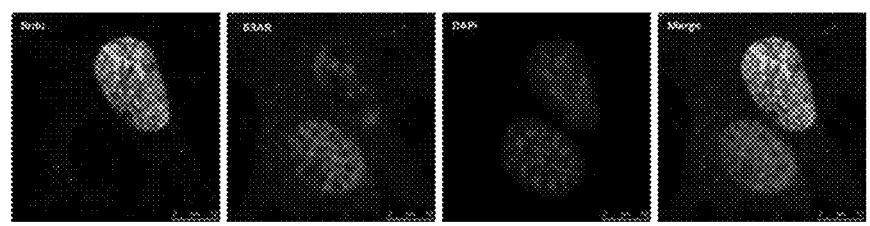
FIG. 5: there are a lot of ADRB3 proteins in the Brdu negative (non-S phase) MCF7 cytoblast.
Figure 6:
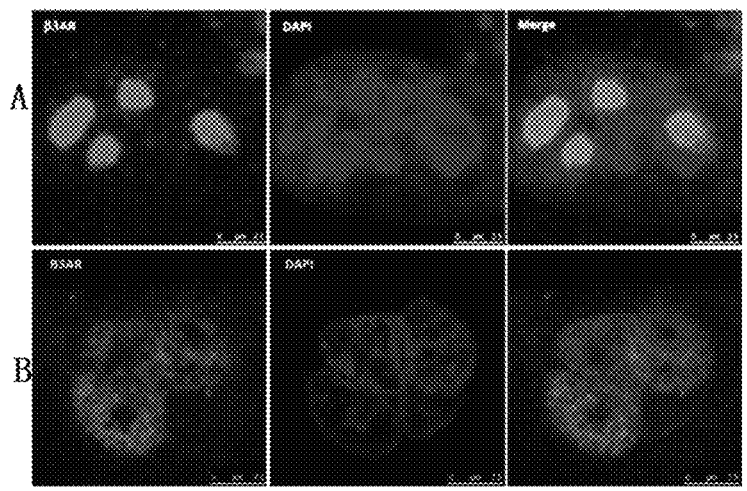
FIG. 6: A. an ADRB3 is accumulated in the MCF7 cytoblast and nucleolus; and B. an ADRB3 is present in a plurality of nucleoli of fusion cells.
Figure 7:
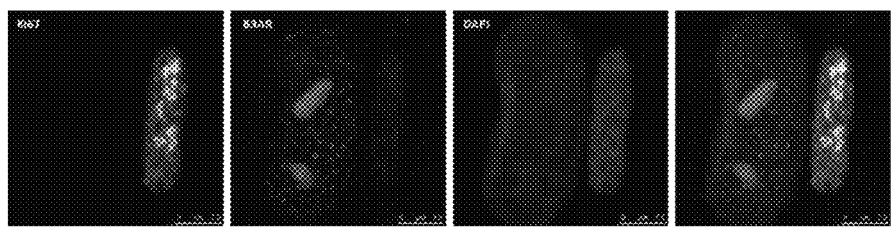
FIG. 7: high expression of an ADRB3 in the nucleolus of the human lung cancer cell A549 at G0 phase (Ki-67 negative); low expression level in cytoblast of the cell (Ki-67 positive) in proliferation phase.
Figure 8:
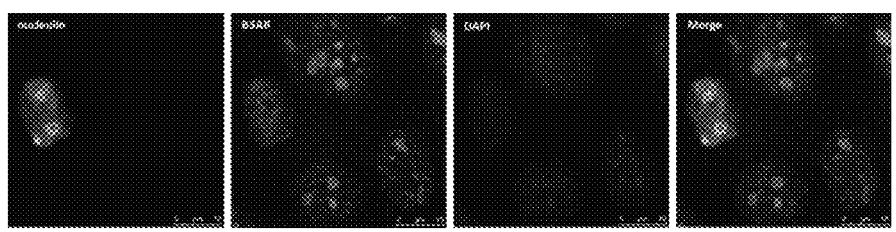
FIG. 8: high expression of an ADRB3 in the nucleolus of the human pancreatic cancer cell CFPAC1 at G0 phase (Nucleolin negative); low expression level in the nucleolus of the cell (Nucleolin positive) in proliferation phase.
Figure 9:
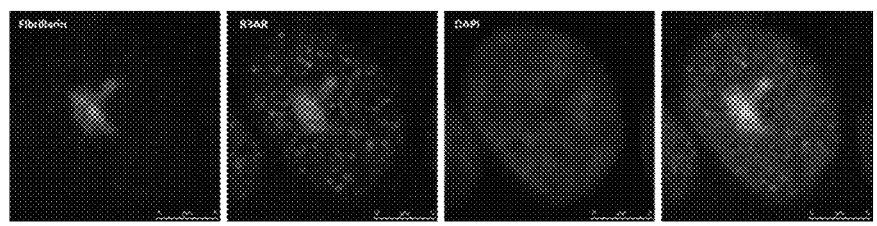
FIG. 9: an ADRB3 is highly expressed in the nucleoli (Fibrillarin positive) of the human melanoma cell A375.
Figure 10:
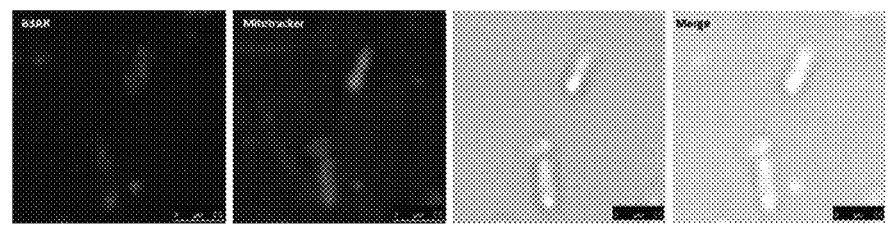
FIG. 10: an ADRB3 is localized in the mitochondrial outer membrane of the human pancreatic cancer cell PANC1.
Figure 11:
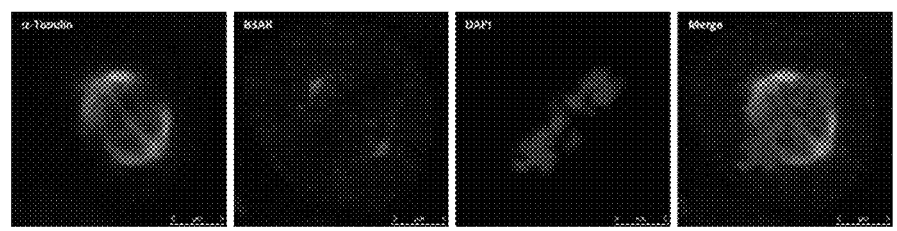
FIG. 11: an ADRB3 is localized in the centrosome at both spindle poles of the MCF7 cell.
Figure 12:
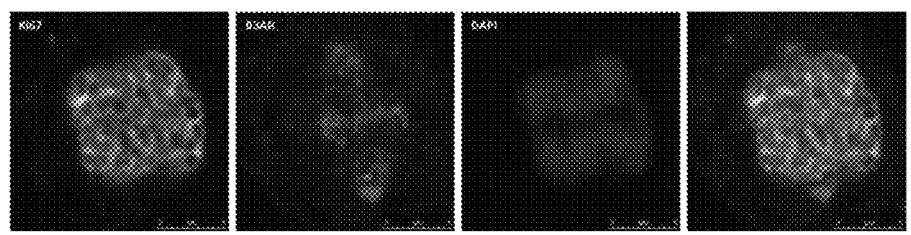
FIG. 12: an ADRB3 is localized at both spindle poles and in the spindle equator of the A549 cell.
Figure 13:
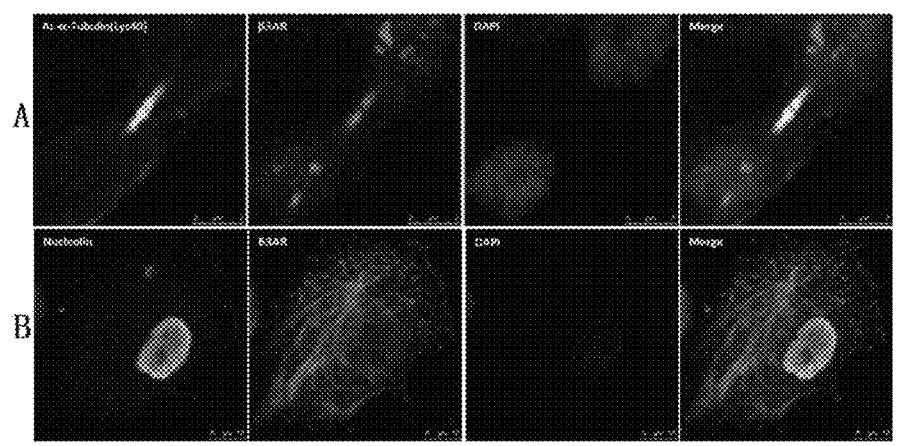
FIG. 13: A. an ADRB3 is localized in the microtubule of the human hepatic cancer cell HepG2; and B. an ADRB3 is localized in the microtubule, cytoblast and mitochondria of the human pancreatic cancer cell PANC1.
Figure 14:
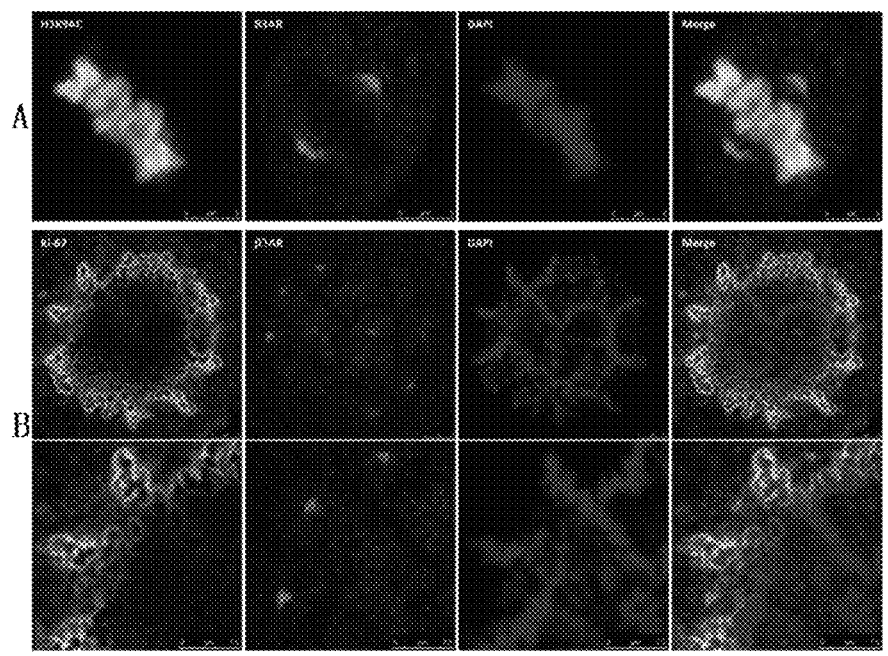
FIG. 14: an ADRB3 is localized at both spindle poles of the human glioma cell A172; and B. an ADRB3 is located in the centrosome position of the polyploid cell MCF7.
Figure 15:
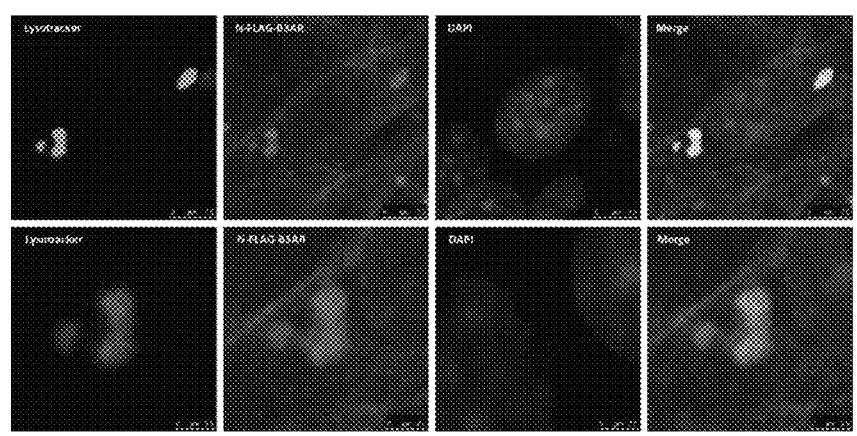
FIG. 15: an ADRB3 is localized on the lysosome of the MCF7 cell.
Figure 16:
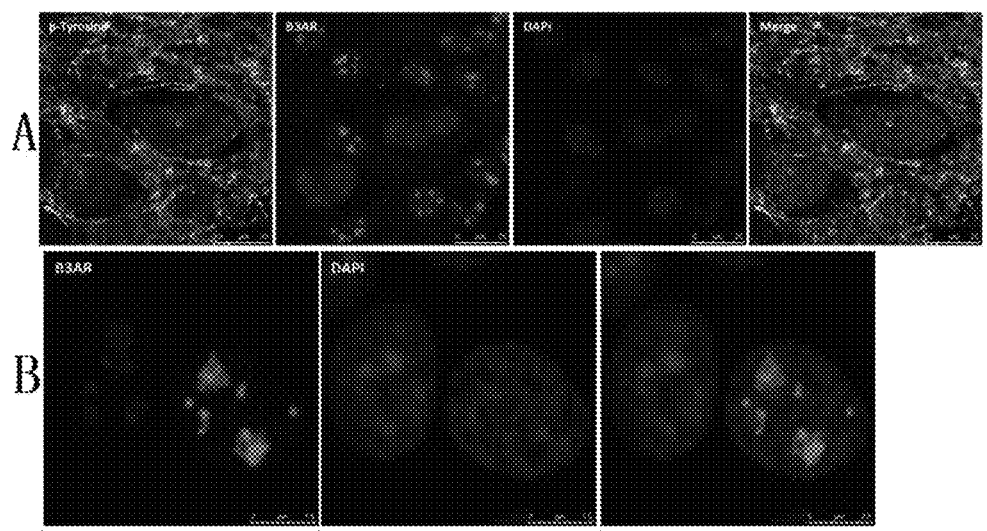
FIG. 16: A. an ADRB3 increases the tyrosine phosphorylation of the protein on the cell membrane at G0 phase, and may promote the tyrosine phosphorylation of membrane proteins, such as HER2/EGFR/drug pump, to activate the membrane proteins; and B. a lot of ADRB3 are accumulated in the MCF7 cytoblast at the end of G2 phase. Under the circumstance, DNA replication is completed, chromosome has been formed, and nucleolus and karyotheca have disappeared.
Figure 17:
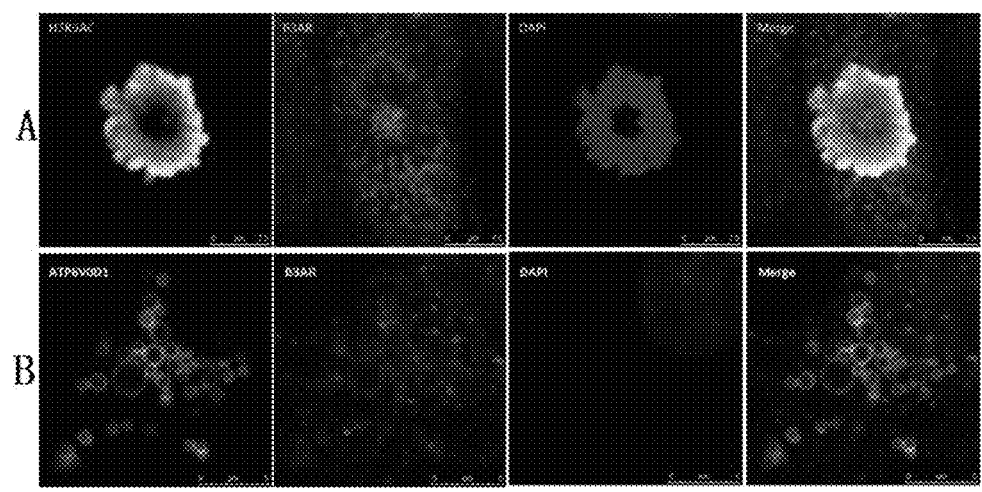
FIG. 17: A. an ADRB3 is located in the centrosome of MCF7 cells at the end of G2 phase to promote formation of the microtubule center; and B. an ADRB3 is located in the vacuolar outer membrane of the MCF7 cell to promote vacuole formation.
Figure 18:
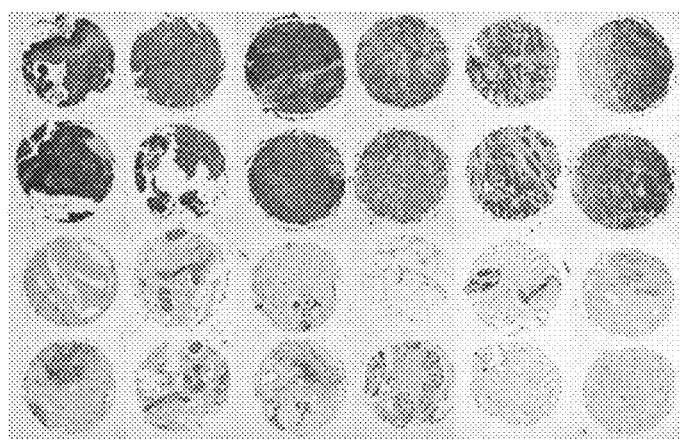
FIG. 18: schematic diagram of ADRB3 expression in breast cancer tissues and paracancerous tissues; high expression of an ADRB3 in breast cancer tissues of pathological grade III; and each column is a sample of a patient, the upper two samples are cancer tissues, and the lower two samples are paracancerous tissues.
Figure 19:
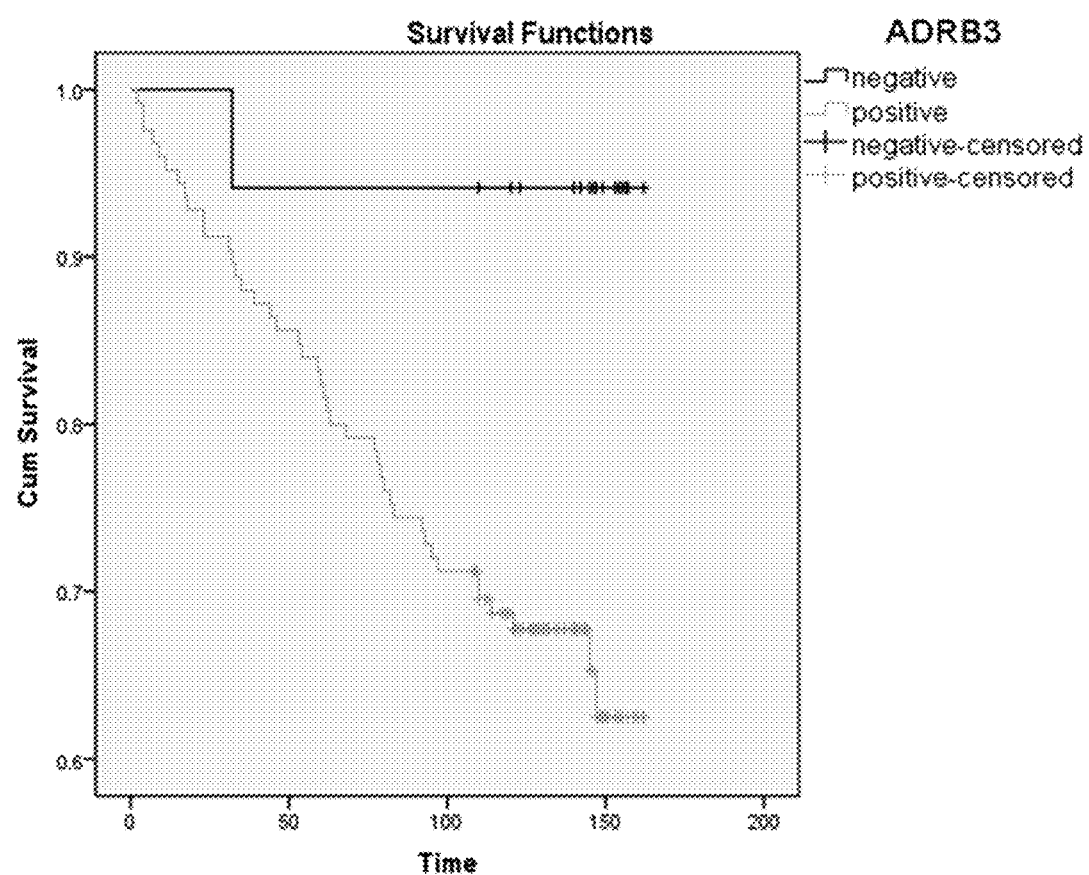
FIG. 19: Kaplan-Meier survival curve of 142 breast cancer patients, where the ordinate is the cumulative survival rate, and the abscissa is the survival time (month); and the survival rate of patients with a negative ADRB3 in cancer tissue is significantly higher than that of patients with a positive ADRB3 in cancer tissue, P=0.025.
Figure 20:
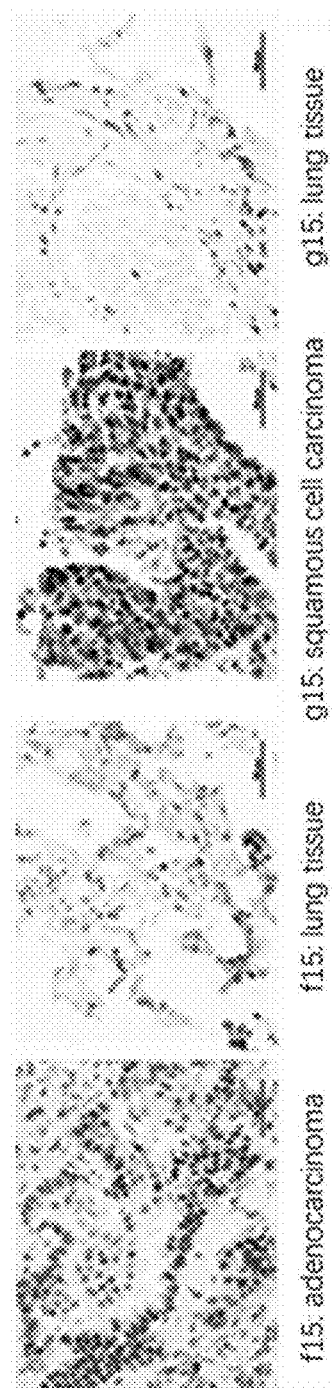
FIG. 20: schematic diagram of ADRB3 expression in lung cancer tissues and paracancerous tissues; the first and second from the right are paracancerous tissues and cancer tissues of a patient with squamous cell lung carcinoma (g15); and the third and fourth from the right are paracancerous tissues and cancer tissues of a patient with lung adenocarcinoma (f15).
Figure 21:
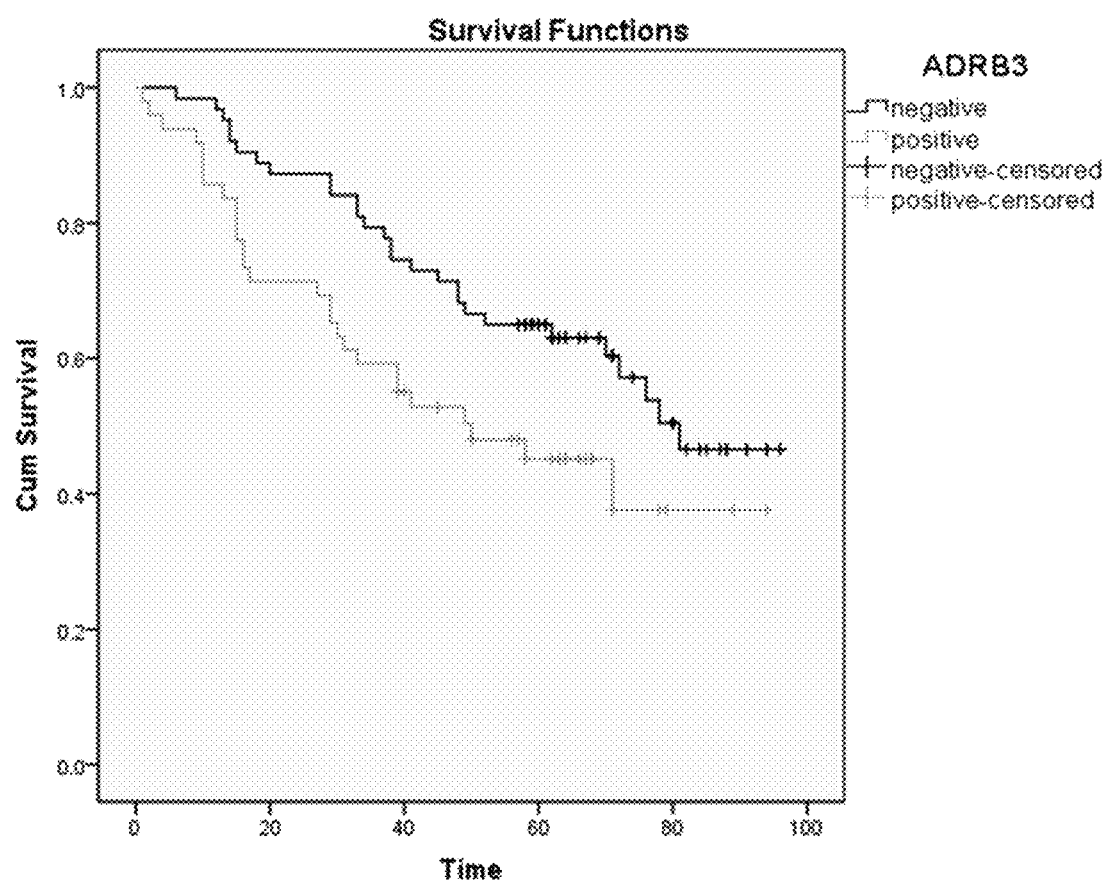
FIG. 21: Kaplan-Meier survival curve of 112 lung cancer patients, where the ordinate is the cumulative survival rate, and the abscissa is the survival time (month); and the survival rate of patients with a weakly positive ADRB3 in cancer tissue is significantly higher than that of patients with a strongly positive ADRB3 in cancer tissue, P=0.038, where 1 means weakly positive, and 2 means strongly positive.
Figure 22:
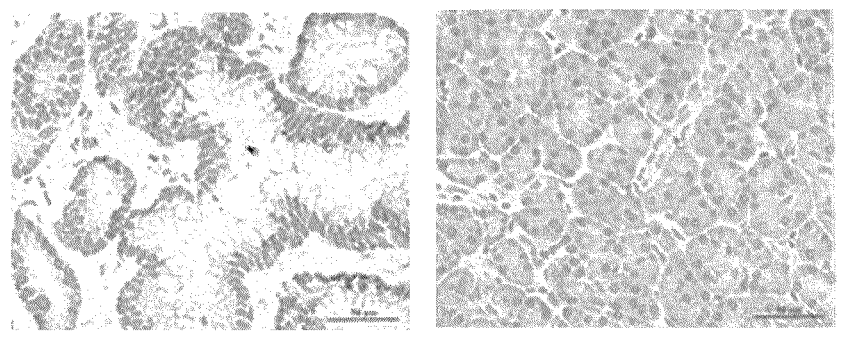
FIG. 22: schematic diagram of ADRB3 expression in pancreatic cancer tissues and paracancerous tissues.
Figure 23:
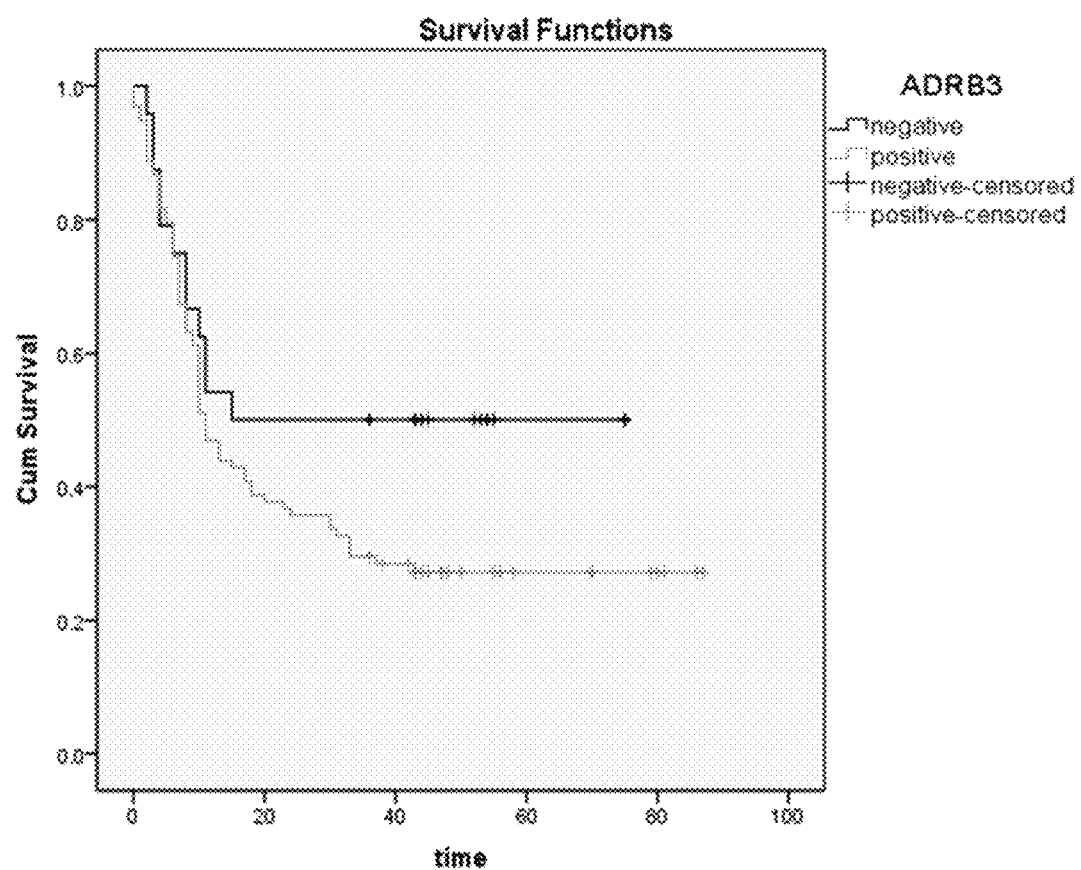
FIG. 23: Kaplan-Meier survival curve of 129 pancreatic cancer patients, where the ordinate is the cumulative survival rate, and the abscissa is the survival time (month); and the survival rate of patients (0) with a negative ADRB3 in cancer tissue is significantly higher than that of patients (1) with a positive ADRB3 in cancer tissue, P=0.019.
Figure 24:
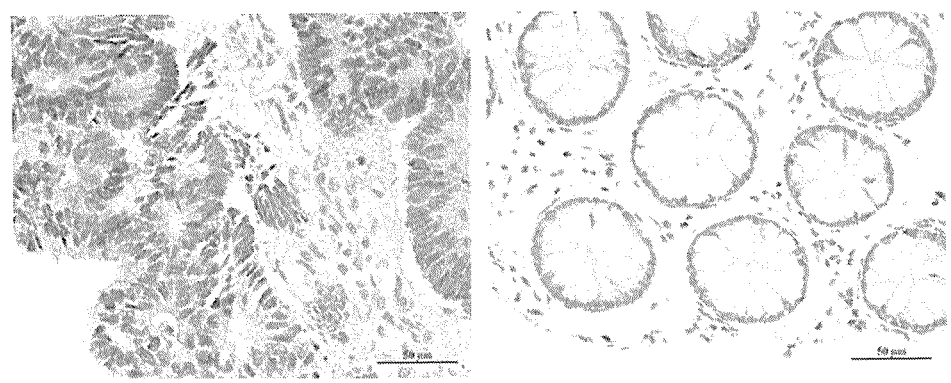
FIG. 24: schematic diagram of ADRB3 expression in 90 colon cancer tissues and paracancerous tissues, where the left figure shows a cancer tissue.
Figure 25:
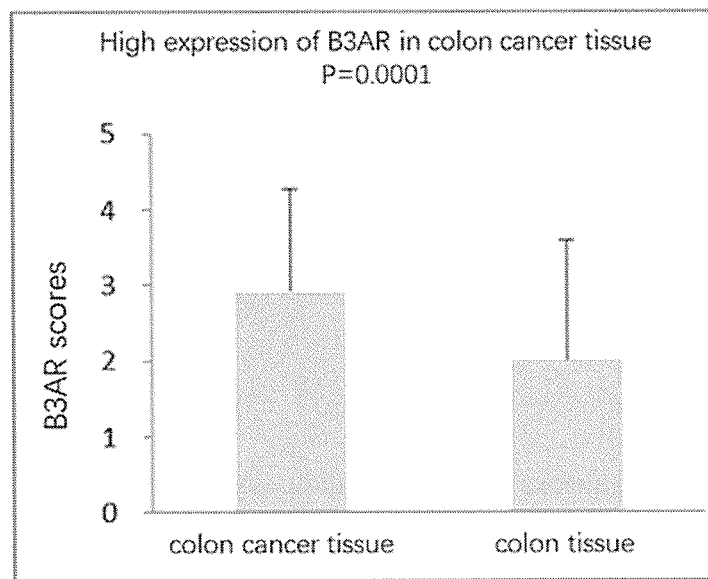
FIG. 25: schematic diagram of ADRB3 expression in 90 colon cancer tissues and paracancerous tissues, where the ADRB3 expression in cancer tissues is significantly higher than that in normal colon tissues (P=0.0001).
Figure 26:
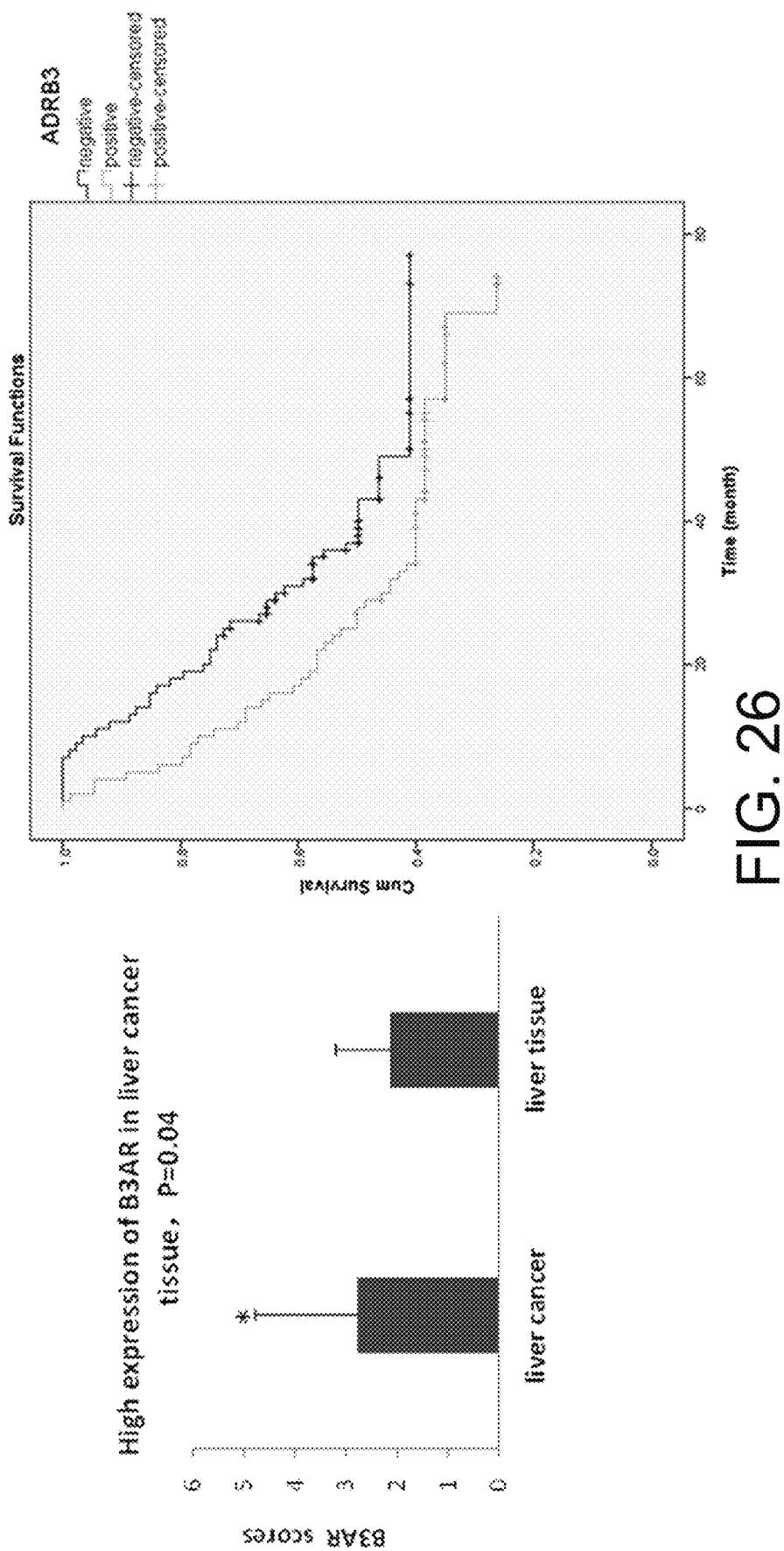
FIG. 26: A. the ADRB3 expression level in cancer tissues of liver cancer patients of more than 50 years old is significantly higher than that in paracancerous tissues, P=0.04; B. Kaplan-Meier survival curve of 162 hepatocellular cancer patients, where the ordinate is the cumulative survival rate, and the abscissa is the survival time (month); and the survival rate of patients (0) with a negative ADRB3 in cancer tissue is significantly higher than that of patients (1) with a positive ADRB3 in cancer tissue, P=0.038.
Figure 27:
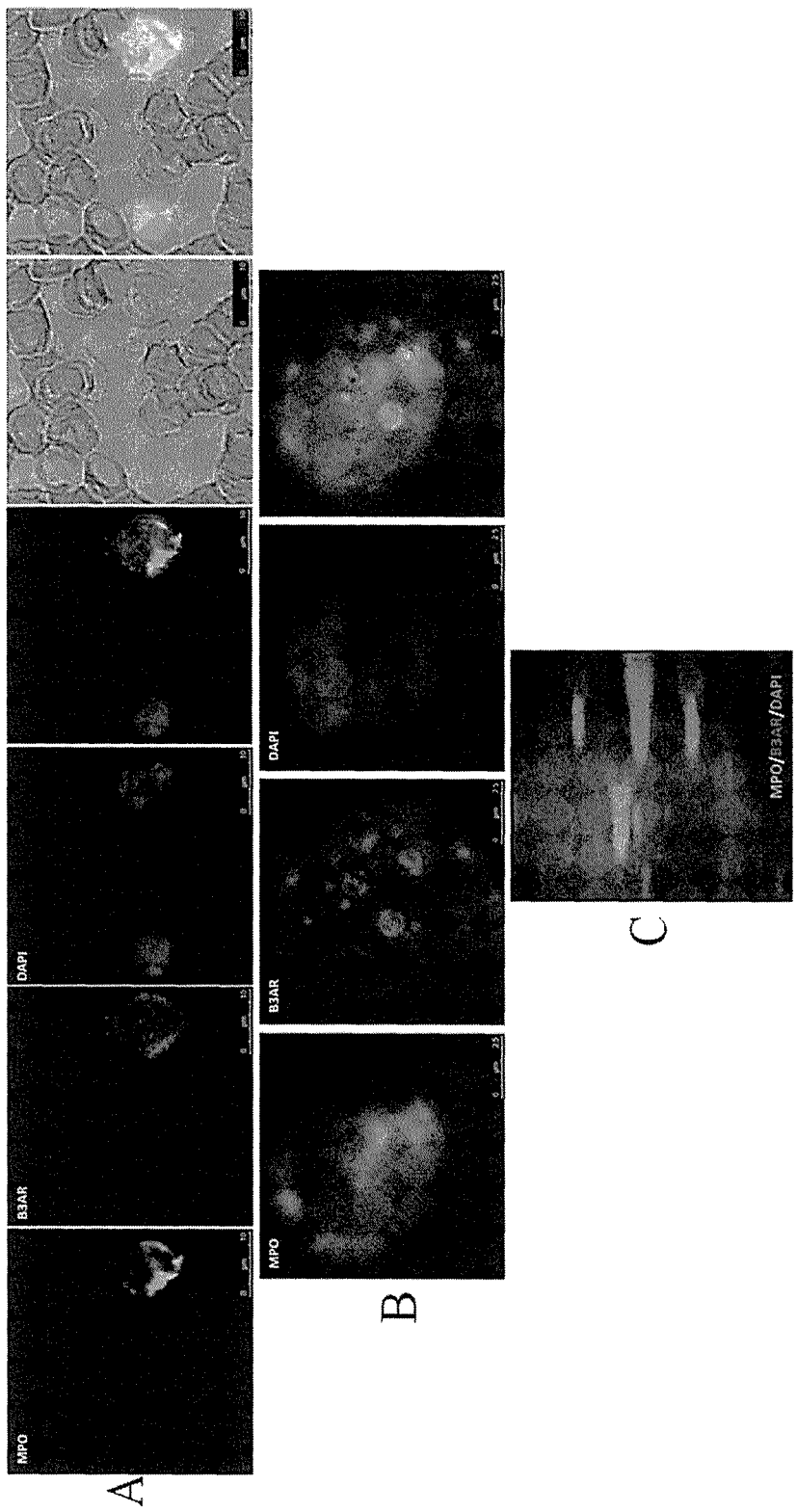
FIG. 27: A. bone marrow smears of normal subjects are stained with ADRB3 and MPO, and an ADRB3 is highly expressed in neutrophils (MPO positive); B. an ADRB3 shows a conical structure and is embedded in cytoblast of neutrophils; and C. the conical ADRB3 complex begins in cell membrane, runs through cytoplasm, and extends to cytoblast to form a channel.
Figure 28:
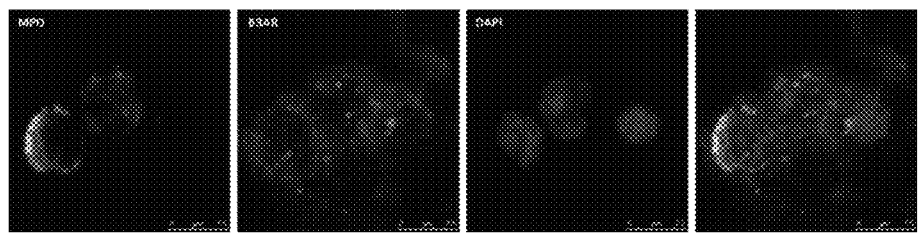
FIG. 28: bone marrow smears of normal subjects injected with granocyte (recombinant human granulocyte colony-stimulating factor) are stained with ADRB3 and MPO; and an ADRB3 is inducibly expressed in lymphocytes.
Figure 29:
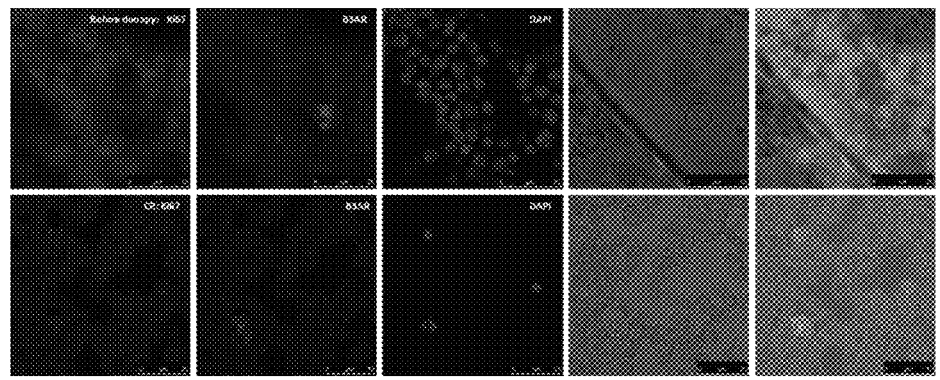
FIG. 29: bone marrow smears of a given patient with acute B lymphocytic leukemia before treatment and after complete response (CR) by treatment are stained with ADRB3 and Ki-67, where the upper figure is before treatment. The expression of ADRB3 in granulocytes and leukaemia cells after complete response (CR) by treatment is reduced, compared with that before treatment.
Figure 30:
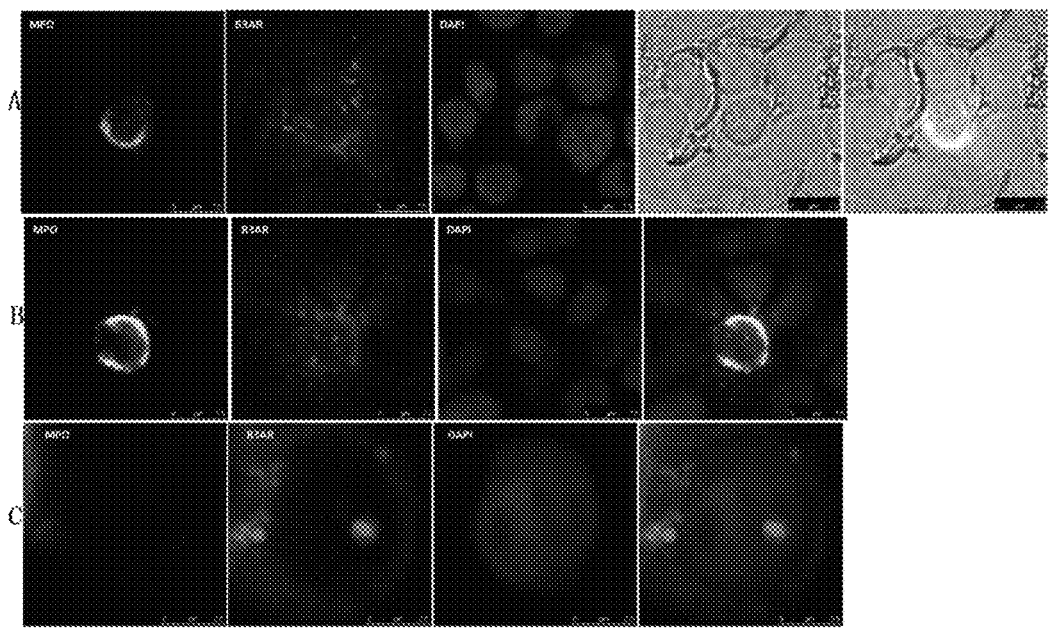
FIG. 30: bone marrow smears of a patient with acute B lymphocytic leukemia suffering a relapse after treatment are stained with ADRB3 and MPO; and an ADRB3 is highly expressed in granulocytes and leukemia cells, suggesting that the ADRB3 induces carcinogenesis of B-lymphocytes; B. the ADRB3 aggregates in a site where granulocytes and lymphocytes contact with each other, which contributes to the stability of intercellular adhesion molecules, and promotes formation of inhibitory immune synapses; and C. the ADRB3 in cytoplasm and cytoblast of lymphocytes forms a conical structure.
Figure 31:
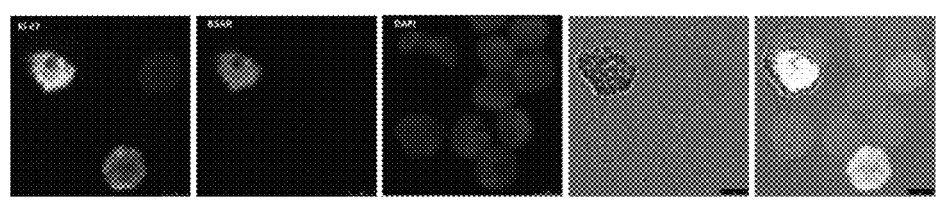
FIG. 31: bone marrow smears of patients with acute B lymphoblastic leukemia suffering a relapse after treatment are stained with ADRB3 and Ki-67. ADRB3 and Ki-67 are highly expressed in granulocytes, which are MDSC, and aggravate the disease progression.
Figure 37:
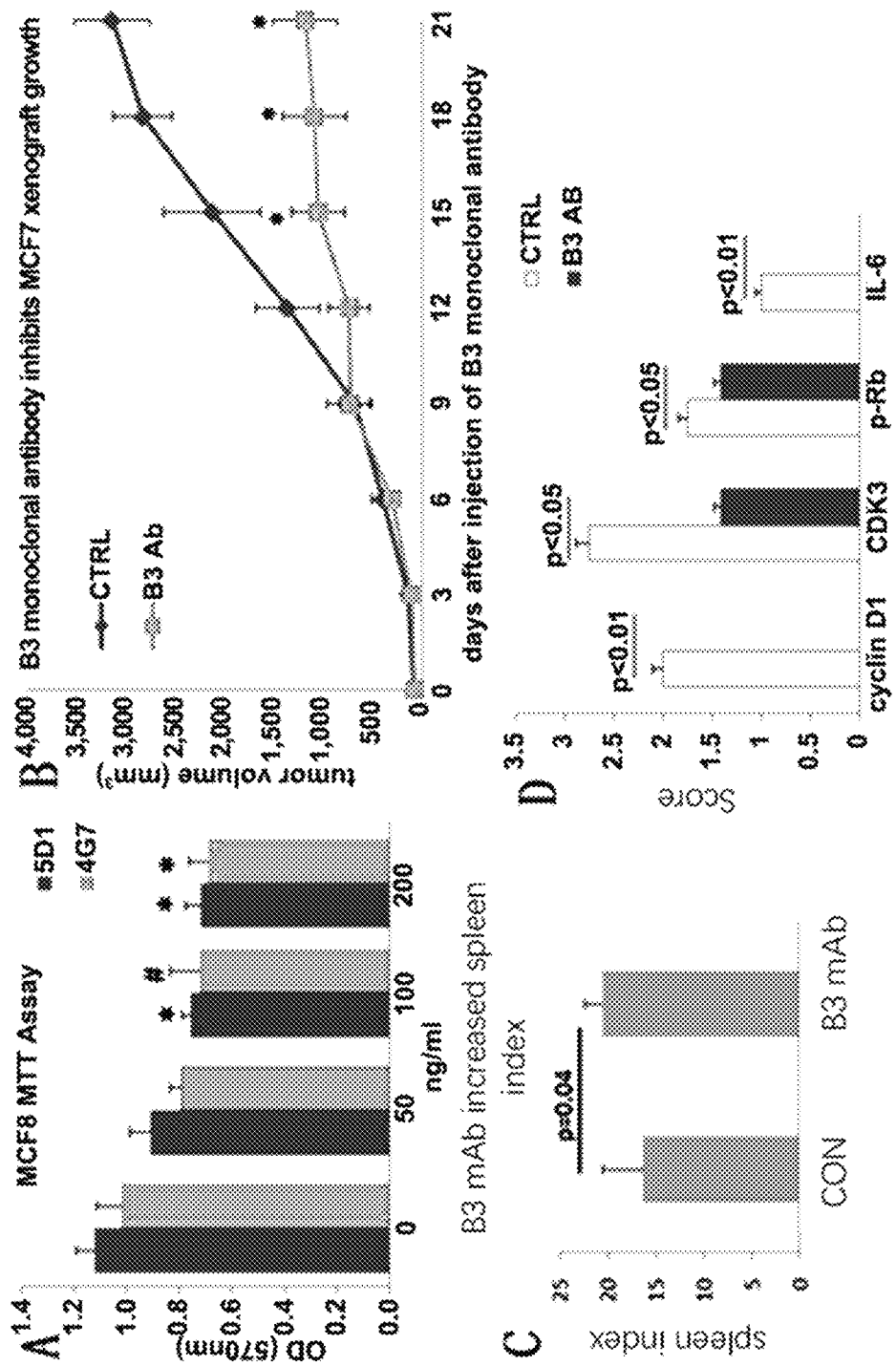
FIG. 37: the ADRB3 antibody can kill MCF7 cells in vitro and in vivo; A. the ADRB3 monoclonal antibody reduces MCF7 breast cancer cell activity; B. the ADRB3 antibody inhibits the proliferation of the breast cancer cell MCF7 transplanted into nude mice, the ordinate is the transplanted tumor volume (mm$^3$), the abscissa is the number of days after inoculating cells, and B3 Ab is the antibody group; C. the ADRB3 antibody increases the spleen index of the nude mice transplanted with the tumor MCF7; and D. the ADRB3 antibody reduces the expressions of cyclin D1, phosphorylated Rb, CDK3 and IL-6 in MCF7 tumor transplanted into nude mice, and reduces the CDK3 activity.
Figure 38:
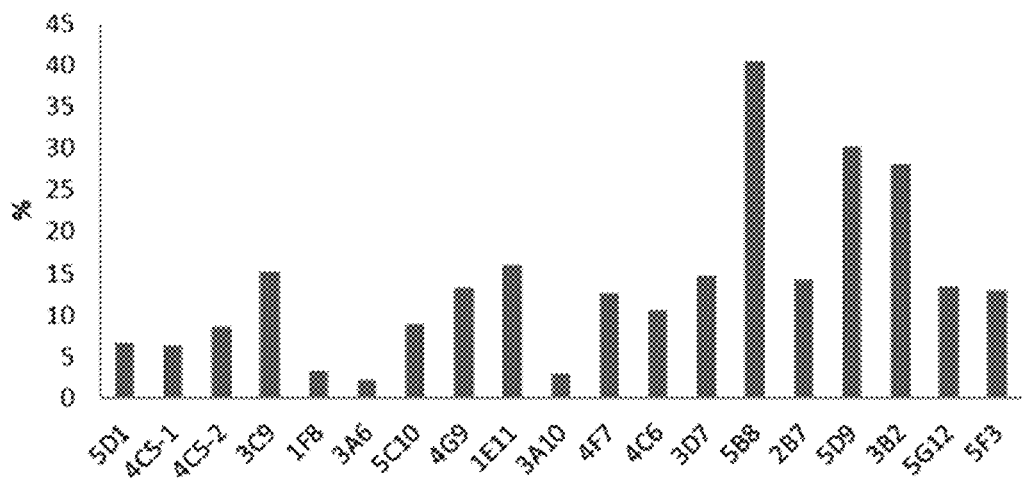
FIG. 38: after the ADRB3 antibodies produced by different cell strains of bone marrow hybridoma are treated, the activity of the pancreatic cancer cell SW1990 is reduced; the antibodies are at a concentration of 250 ng/ml; and the abscissa is the hybridoma cell strain number.
Figure 39:
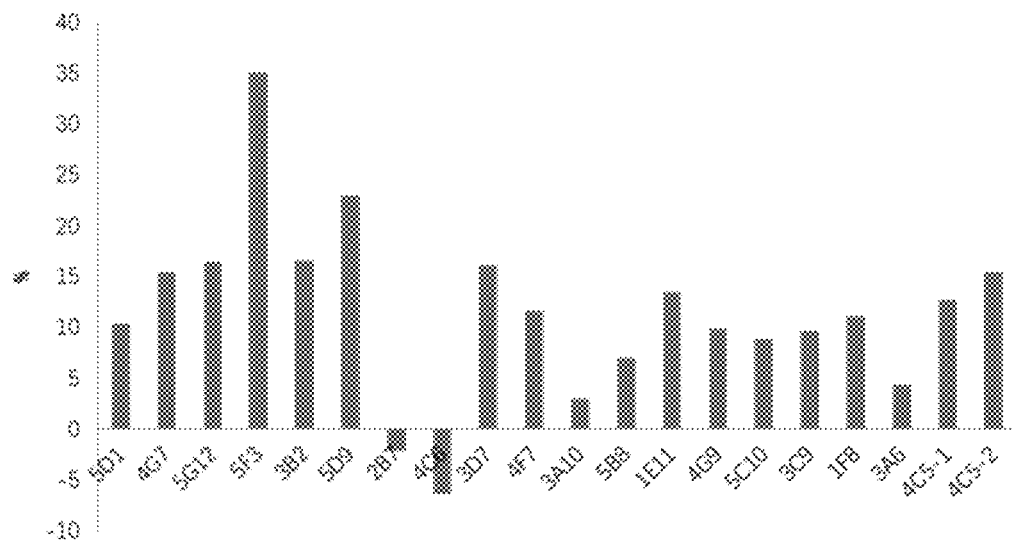
FIG. 39: after the ADRB3 antibodies produced by different cell strains of bone marrow hybridoma are treated, the activity of CFPAC1 cells is reduced; the antibodies are at a concentration of 250 ng/ml; and the abscissa is the hybridoma cell strain number.
Figure 40:
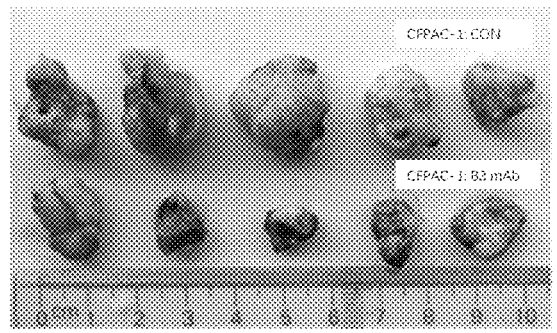
FIG. 40: the ADRB3 antibody reduces the volume of tumor transplanted with CFPAC1 cells in nude mice.
Figure 41:
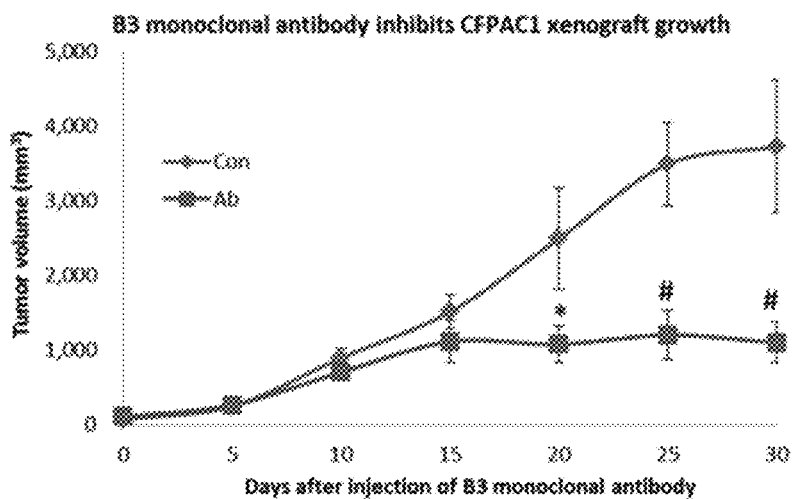
FIG. 41: growth curve of the tumor transplanted with human pancreatic cancer cell CFPAC1 inoculated into nude mice, Ab is the antibody treated group, and the ADRB3 monoclonal antibody inhibits the proliferation of the tumor transplanted with CFPAC1.
Figure 42:
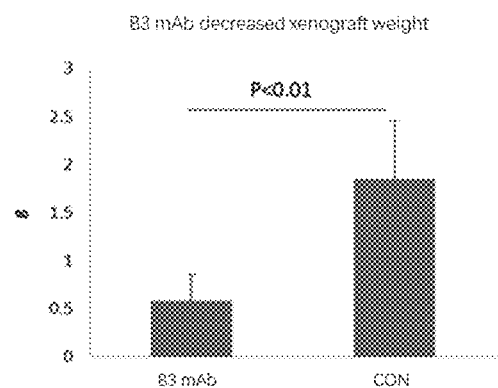
FIG. 42: histogram of the tumor weight in the nude mice transplanted with the pancreatic cancer cell CFPAC1; the ADRB3 monoclonal antibody reduces the weight of the tumor transplanted with CFPAC1.
Figure 43:
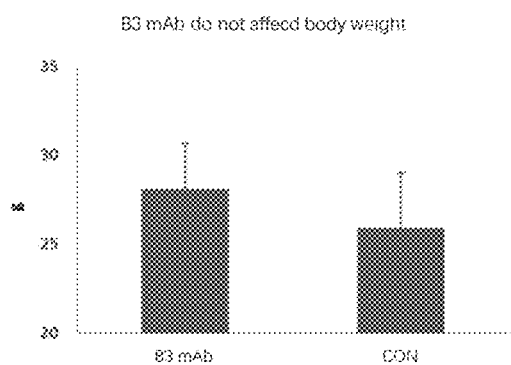
FIG. 43: histogram of the body weight of the nude mice transplanted with CFPAC1; the ADRB3 antibody doesn't affect the body weight of the nude mice transplanted with CFPAC1.
Figure 44:
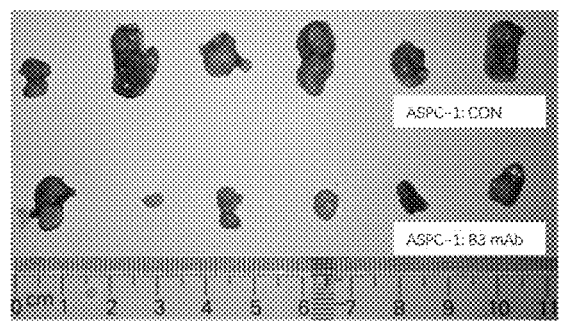
FIG. 44: tumor transplanted with the pancreatic cancer cell ASPC1 in nude mice; the ADRB3 antibody reduces the volume of the tumor transplanted with ASPC1.
Figure 45:
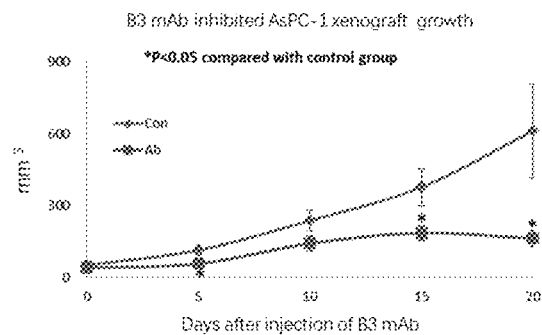
FIG. 45: growth curve of the tumor transplanted with the human pancreatic cancer cell ASPC1 inoculated into nude mice, Ab is the ADRB3 antibody treated group, and the ADRB3 monoclonal antibody inhibits the proliferation of the tumor transplanted with ASPC1.
Figure 46:
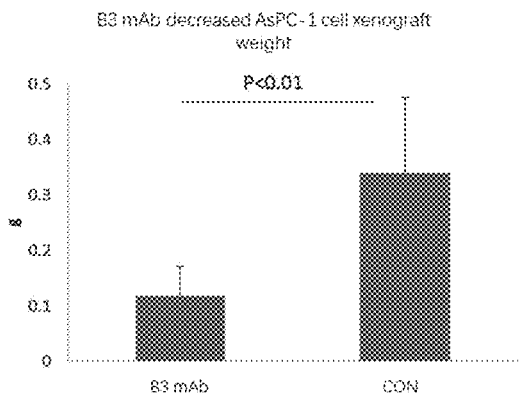
FIG. 46: histogram of the tumor weight in the nude mice transplanted with the pancreatic cancer cell ASPC1; the ADRB3 monoclonal antibody reduces the weight of the tumor transplanted with ASPC1.
Figure 47:
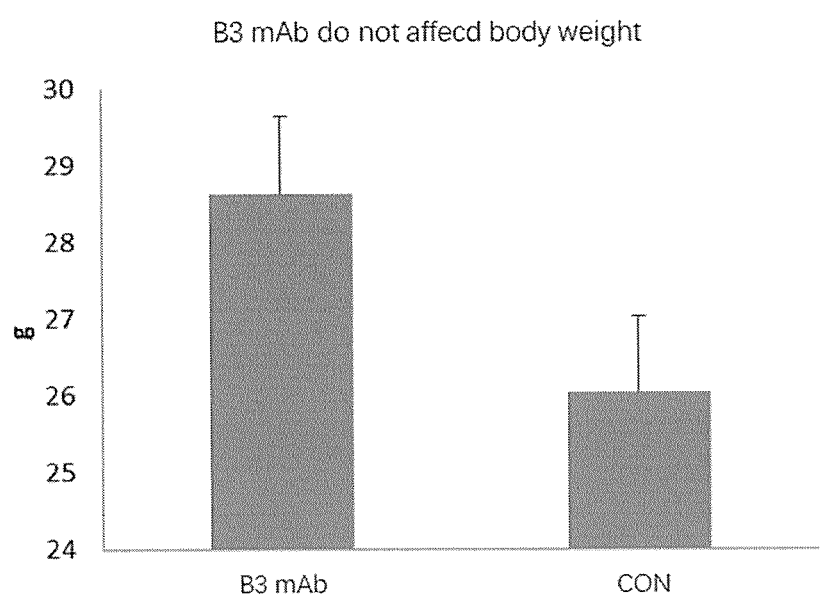
FIG. 47: histogram of the body weight of the nude mice transplanted with ASPC1; the ADRB3 monoclonal antibody doesn't affect the body weight of the nude mice transplanted with ASPC1.
Figure 48:
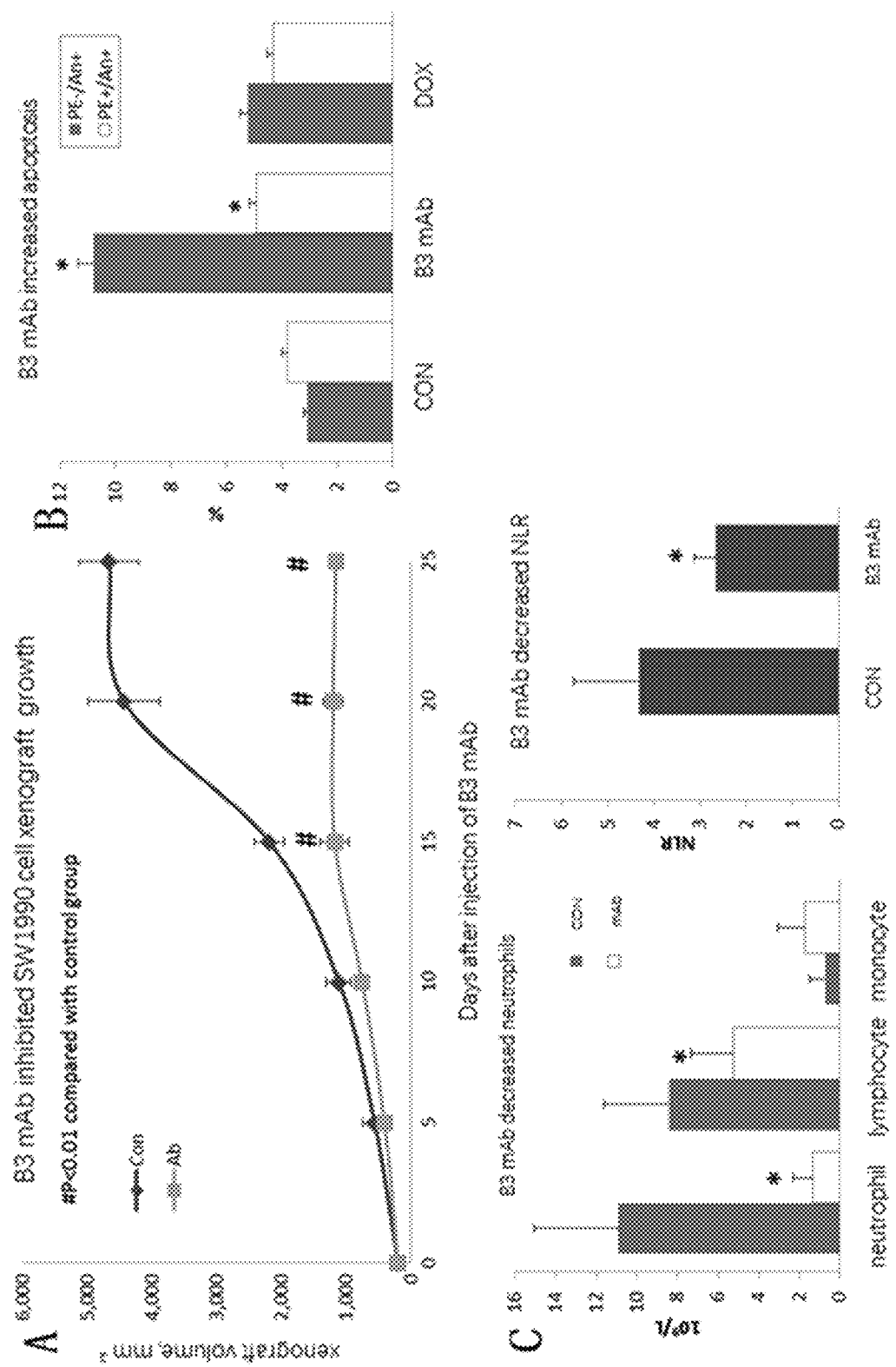
FIG. 48: the ADRB3 monoclonal antibody treats the nude mice transplanted with SW1990; A. growth curve of the tumor transplanted with the human pancreatic cancer cell SW1990 inoculated in nude mice, and the ADRB3 monoclonal antibody inhibits proliferation of the tumor transplanted with SW1990; B. ADRB3 monoclonal antibody increases the apoptosis rate of SW1990; and C. the ADRB3 antibody reduces granulocytes and NLR of the SW1990 tumor-bearing mice, compared with the control group. *P<0.05.
Figure 49:
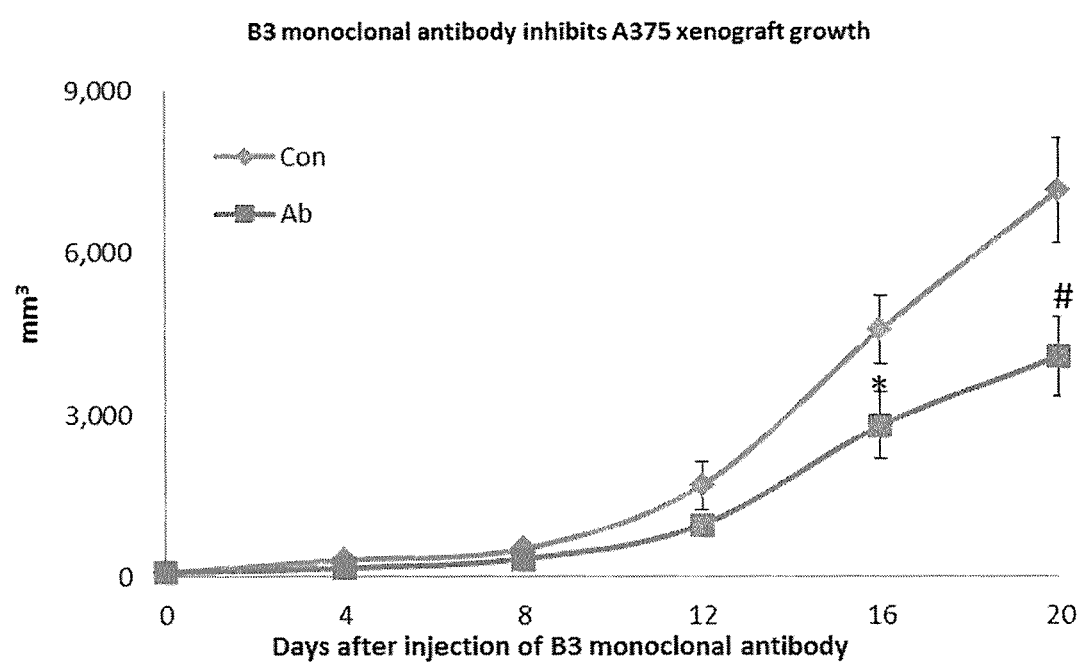
FIG. 49: growth curve of the tumor transplanted with human melanoma cell A375 inoculated into nude mice; the ADRB3 monoclonal antibody inhibits the proliferation of the tumor transplanted with A375; *p=0.032, #p=0.005; and Ab is the ADRB3 antibody treated group.
Figure 50:
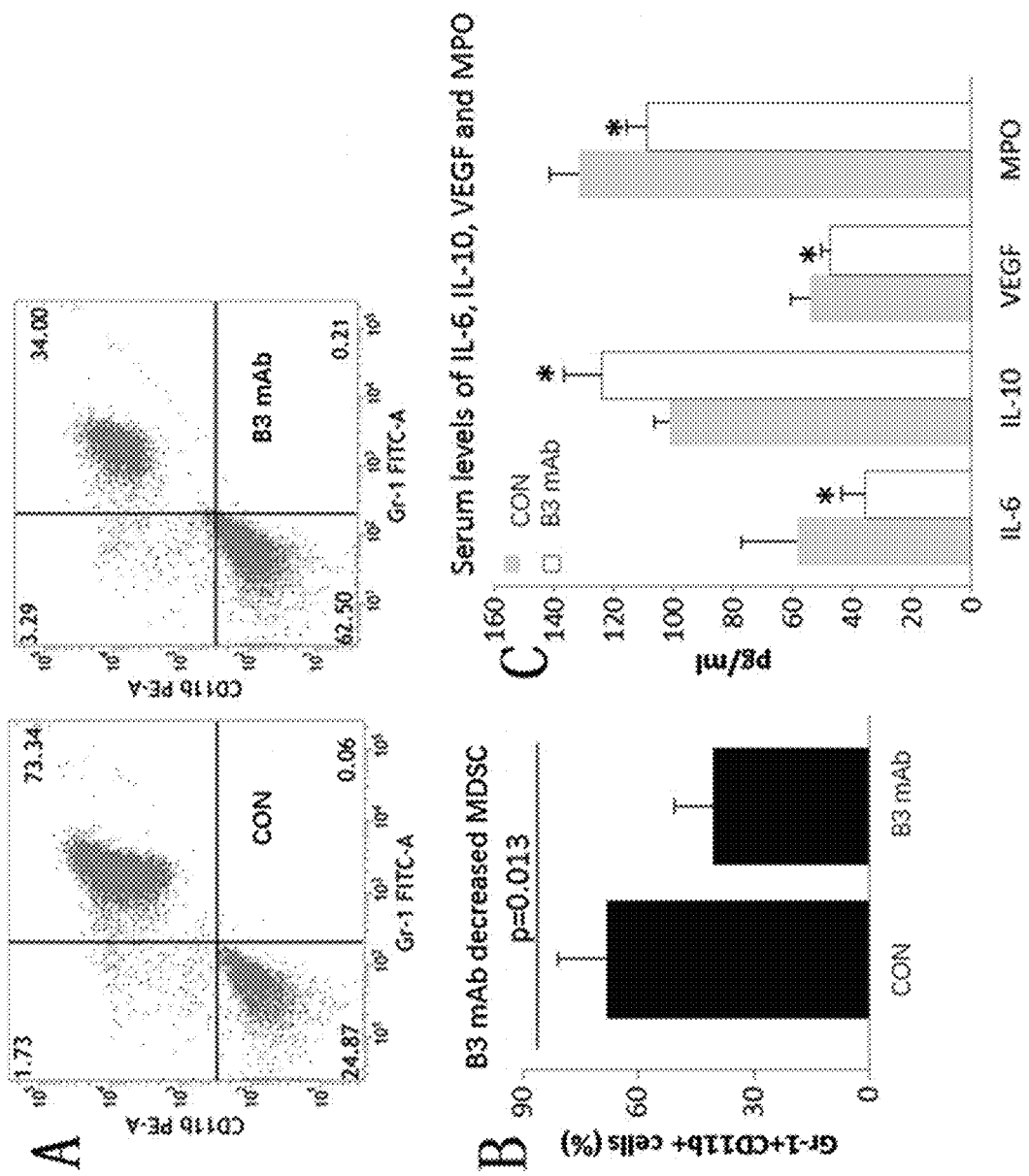
FIG. 50: the ADRB3 monoclonal antibody treats the nude mice transplanted with A375; A. flow cytometry for detection of MSDC in the peripheral blood of the nude mice transplanted with A375; B. the ADRB3 antibody reduces the number of MSDC in the peripheral blood of the nude mice transplanted with A375; C. ELISA of the serum in tumor-bearing mice; and the ADRB3 antibody increases IL-10, reduces IL-6, VEGF and MPO concentrations, and compared with the control group, *p<0.05.
Figure 51:
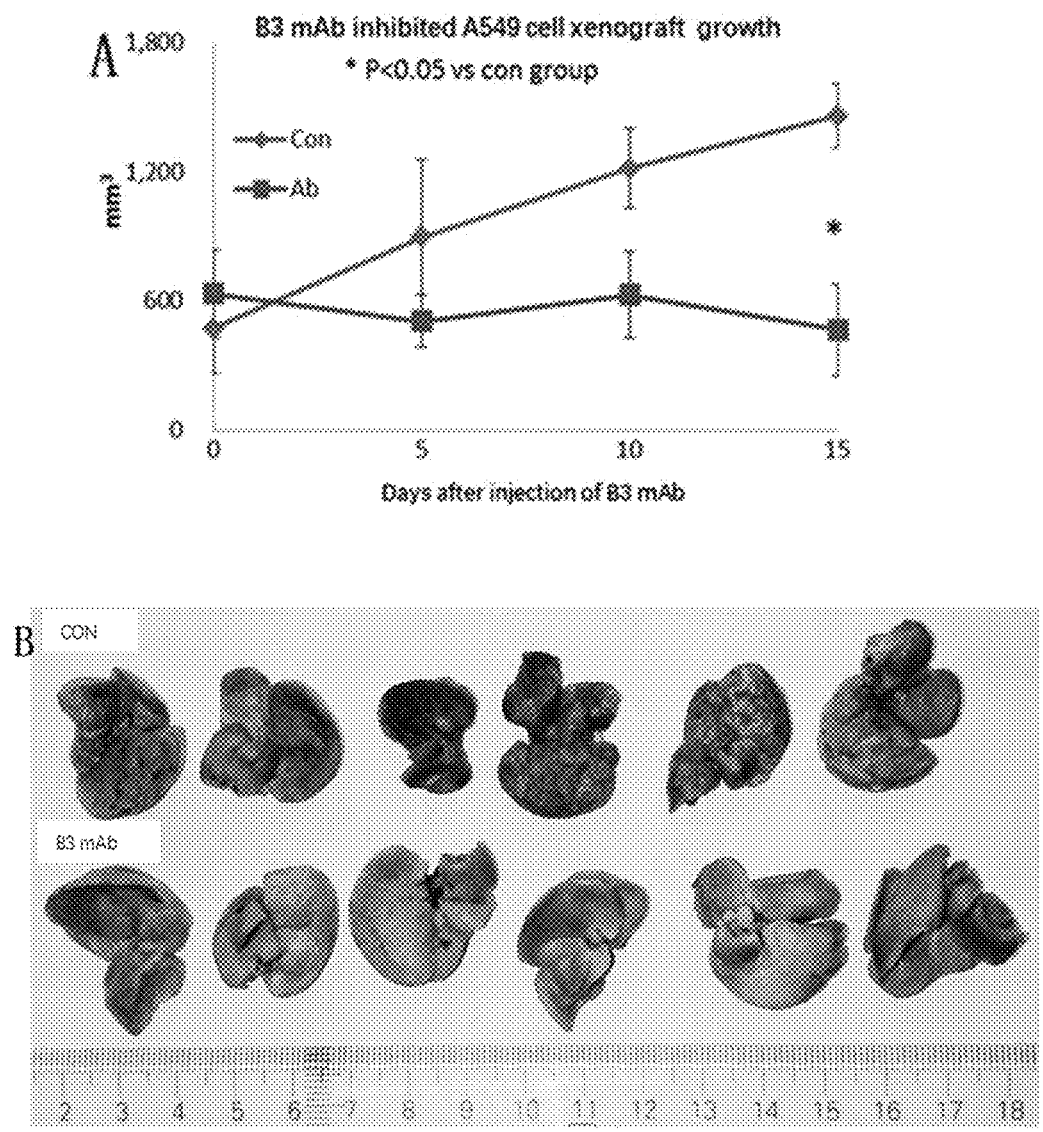
FIG. 51: A. growth curve of the tumor transplanted with the human lung cancer cell A549 inoculated into nude mice; the ADRB3 monoclonal antibody inhibits the proliferation of the tumor transplanted with A549, and compared with the control group, *p<0.05; and B. the ADRB3 antibody inhibits liver metastasis of the 4T1 breast cancer cell in mice.
Figure 52:
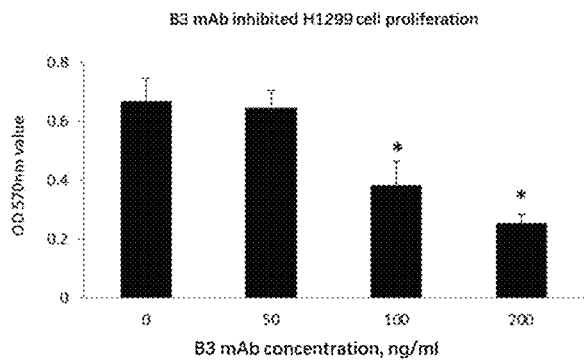
FIG. 52: the ADRB3 monoclonal antibody dose-dependently decreases the activity of the human lung cancer cell H1299.
Figure 53:
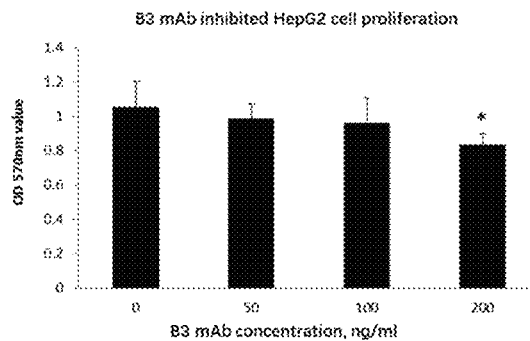
FIG. 53: the ADRB3 monoclonal antibody dose-dependently decreases the activity of the human hepatic cancer cell HepG2.
Figure 54:
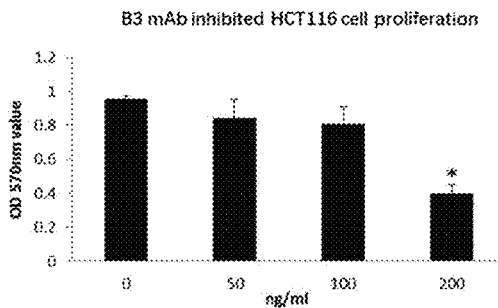
FIG. 54: the ADRB3 monoclonal antibody dose-dependently decreases the activity of the human colon cancer cell HCT116.
Figure 55:
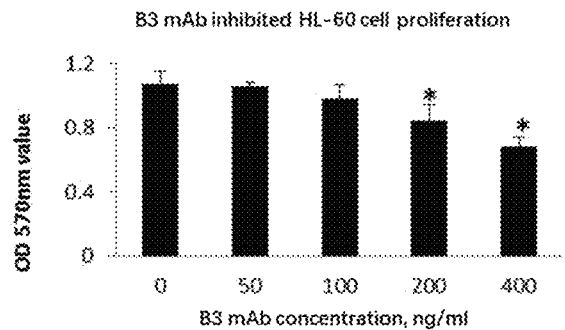
FIG. 55: the ADRB3 monoclonal antibody dose-dependently decreases the activity of the human promyelocytic leukemia cell HL-60.
Figure 56:
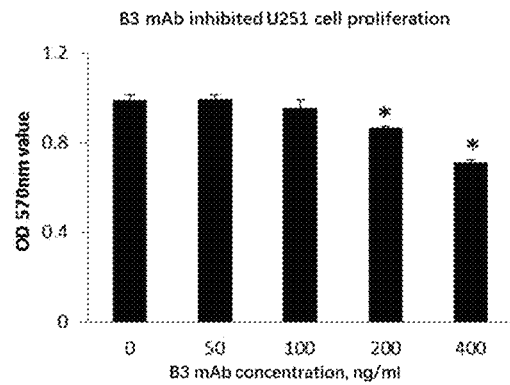
FIG. 56: the ADRB3 monoclonal antibody dose-dependently decreases the activity of the human glioma cell U251.

As shown in FIG. 1 to 17, the following results may be obtained:

(1) by staining with Ki67/nucleolin/Brdu, it is found that a lot of nucleoli are present in cells at G0 phase, but nucleolar constituent protein at G0 phase is different from that in cells in G1 phase. Nucleolar protein markers in G1 phase could not be used to mark nucleoli in cells at G0 phase. An ADRB3 is highly expressed in the nucleoli of the human breast cancer cell MCF7 at G0 phase (Ki-67 and Nucleolin: negative). In FIG. 1, the upper right cell is a cell with proliferation capacity at G0 phase.

(2) The ADRB3 is highly expressed in the nucleoli of the human lung cancer cell A549 at G0 phase (Ki-67 negative).

(3) The ADRB3 is highly expressed in the nucleoli of the human pancreatic cancer cell CFPAC1 at G0 phase.

(4) The ADRB3 is highly expressed in the nucleoli (Fibrillarin positive) of the human melanoma cell A375.

(5) The ADRB3 is localized in the mitochondrial outer membrane of the human pancreatic cancer cell PANC1.

(6) The ADRB3 is localized in the centrosome at both spindle poles and the spindle equator of A549 cells. The ADRB3 is in a plurality of cytoblasts of the fusion cells.

(7) The ADRB3 is localized on the microtubule of the human hepatic cancer cell HepG2.

(8) The ADRB3 is localized in the centrosome at both spindle poles of the human glioma cell A172. The ADRB3 is localized at the centrosomal position of the polyploid cell.

(9) The ADRB3 is localized on the lysosome of the MCF7 cell. The ADRB3 increases the tyrosine phosphorylation of the protein on cell membrane at G0 phase, and promotes the tyrosine phosphorylation of membrane proteins, such as HER2/EGFR/drug pump, to activate the membrane proteins.

(10) The ADRB3 is located in the centrosome of MCF7 cell at the end of G2 phase to promote formation of the microtubule center.

(11) The ADRB3 is in the vacuolar outer membrane of the MCF7 cell to promote the vacuole formation. ATP6V0D1 is a D subunit of a vacuolar ATP enzyme, and is localized in the vacuolar membrane. The ADRB3 and ATP6V0D1 are co-localized, indicating that the ADRB3 is located in the vacuole membrane.

Example 2 Immunohistochemical Analysis on Tissue Microarrays for Detection of ADRB3 Expression in Tumor Tissues 1. 11 different tumor tissue microarrays from a total of 1,479 patients were used in this research: (1) 42 patients with NSCLC; (2) 150 lung adenocarcinoma patients with survival time data; (3) 150 patients with pulmonary squamous cell carcinoma with survival time data; (4) 180 liver cancer patients with survival time data; (5) 170 breast cancer patients with survival time data and 82 breast cancer patients without survival time data; (6) 170 pancreatic cancer patients with survival time data; (7) 62 patients with papillary thyroid carcinoma; (8) 90 colon cancer patients with survival time data; (9) 90 kidney cancer patients with survival time data; (10) 93 esophagus cancer patients with survival time data; (11) 90 gastric cancer patients with survival time data; (12) 90 colorectal cancer patients with survival time data; and (13) 20 leukemia patients.

2. Experimental steps: (1) paraffin section: thickness 4 m; (2) baking slices: 65° C. for 3 h; (3) dewaxing until putting in water: dimethylbenzene 10 min×3 cylinders, 100%-100%-95%-95%-90%-80%-70% alcohol each for 5 min, hydration for 5-10 min; (4) antigen retrieval: high pressure repair in TRIS-EDTA repair solution at PH8.0 for 3 min since the exhaust valve begins exhausting, natural cooling; (5) incubation in 3% hydrogen peroxide for 10 min; (6) rinsing with PBS for 5 min×3 times; (7) closing with 10% goat serum for 10 min; (8) preparation of primary antibody (1:10); (9) discarding the serum, and then adding primary antibody, keeping at 4° C. overnight; (10) on completion of incubation, rinsing with PBS for 5 min×3 times; (11) adding secondary antibody, and then incubating at room temperature for 30 min; (12) rinsing with PBS for 5 min×3 times; (13) developing with DAB (the ratio of solution A to solution B is 1:50). Observed under a microscope, it can be terminated when the expression is appropriate and the background is clear. (14) restraining with hematoxylin for 1 min, and returning to blue with warm water for 15 min; (15) dehydration through gradient alcohols: 70%-80%-90%-95%-95%-100%-100%, each for 3 sec; (16) transparentizing with dimethylbenzene for 5 min×2 cylinders; and (17) sealing the slice with a neutral gum.

3. Determination of Staining Intensity:

Each tissue site was randomly observed in 6 to 8 high power fields, and a case of positive staining was determined if the positive cell count was more than 5%. Weakly positive staining was yellowish (+ or 1), moderately positive staining was brown yellow (++ or 2), and strongly positive staining was brown (+++ or 3).

Determination of positive staining rate: each tissue site was randomly observed in 6 to 8 high power fields, and a case of positive staining was determined if the positive cell count was more than 5%. Weakly positive staining was yellowish (+ or 1), moderately positive staining was brown yellow (++ or 2), and strongly positive staining was brown (+++ or 3). Determination of the positive staining rate: 3 fields of different staining intensities were evaluated under a high-magnification microscope, 100 cells were randomly recorded in each field, and the percentage of positive cells per 100 cells ×1% was recorded. Likewise, the percentage of positive cells in another 2 fields ×2% and ×3% was observed, and finally the positive staining rate of the tissue site was the mean value of ×1%, ×2% and ×3%.

Each site in the tissue microarray was scored based on the sum of the integral of the cell staining strength and the area of stained cells. Firstly, the straining intensity was scored: 0: colorless, 1: pale yellow, 2: brown yellow, and 3: brown. Then the percentage of positive cells was scored: 0: negative, 1: <25%, 2: 25%-50%, and 3: >50%. The two integrals add up to the score of the site.

Kaplan-Meier method was used to analyze the survival of ADRB3 negative and positive patients in cancer tissues and obtain two survival curves. The Log Rank method was used as a statistical test to compare whether the distribution of survival curve of each group is identical.

4. Test Results

The results are shown in FIG. 18 to 26 and Table 1 to 3. Table 1 shows that the ADRB3 expression in breast cancer tissues is significantly higher than that in normal breast tissues (P<0.01). Table 2 shows that the ADRB3 expression in lung cancer tissues is significantly higher than that in normal lung tissues (P<0.01). Table 3 shows that the ADRB3 expression in pancreatic cancer tissues is significantly higher than that in normal pancreatic tissues (P<0.01).

TABLE 1

Expression of ADRB3 in 228 Breast Cancer Tissues and 89 Paracancerous Tissues
Expression of breast cancer tissues and paracancerous tissues

| B3AR | Number of cases | − | + | ++ | +++ |
|---|---|---|---|---|---|
| Cancer | 228 | 18 | 91 | 80 | 39 |
| Proportion of different staining intensities | | 7.9% (18/228) | 39.9% (91/228) | 35.1% (80/228) | 17.1% (39/228) |
| Positive rate | | | | | 92.1% (210/228) |
| paracancerous | 89 | 61 | 27 | 1 | 0 |
| Proportion of different staining intensities | | 68.5% (61/89) | 30.3% (27/89) | 1.1% (1/89) | 0.00% |
| Positive rate | | | | | 31.5% (28/89) |

TABLE 2

Expression of ADRB3 in 150 Lung Cancer Tissues and Paracancerous Tissues

| B3AR | Number of cases | − | + | ++ | +++ |
|---|---|---|---|---|---|
| Cancer | 150 | 8 | 63 | 45 | 34 |
| | | 5.3% | 42.0% | 30.0% | 22.7% |
| Total positive rate | | | | | 94.7% |
| Paracancerous | 150 | 139 | 10 | 1 | 0 |
| | | 92.7% | 6.7% | 0.7% | 0.0% |
| Total positive rate | | | | | 7.3% |

TABLE 3

Expression of ADRB3 in 165 Pancreatic Cancer Tissues and Paracancerous Tissues

| B3AR | Number of cases | − | + | ++ | +++ |
|---|---|---|---|---|---|
| Cancer | 165 | 26 | 84 | 51 | 4 |
| | | 15.8% | 50.9% | 30.9% | 2.4% |
| Total positive rate | | | | | 84.2% |
| Paracancerous | 165 | 115 | 46 | 4 | 0 |
| | | 69.7% | 27.9% | 2.4% | 0.0% |
| Total positive rate | | | | | 30.3% |

As shown in FIG. 18 to 26 and Tables 1 to 3, the following test results may be obtained:

(1) positive expression of the ADRB3 protein is mainly localized in cytoblast, and less localized in cytoplasm and cell membrane. The positive rate of the ADRB3 in breast cancer tissues is 92.1% (210/228), of which 56.7% is moderately and strongly positive. In paracancerous breast cancer tissues, the positive rate of the ADRB3 is 31.5% (28/89), of which moderately positive rate is 3.6% (1/28), and strongly positive rate is 0. The ADRB3 expression in breast cancer tissues is significantly higher than that in normal breast tissues (P<0.01). The ADRB3 expression level is positively correlated with the malignancy degree of breast cancer, and is gradually increased with the increase of the cell malignancy degree. The positive rate is 73.7% (28/38) in breast cancer tissues of pathological grade I, and 97.6% (40/41) in breast cancer tissues of grade III. The ADRB3 is highly expressed in breast cancer tissues of pathological grade III, which is significantly higher than breast cancer tissues of Grade I (P<0.01). The ADRB3 expression level is associated with the breast cancer stage (clinical stage in sixth edition of AJCC), and the later the tumor course is, the stronger the ADRB3 expression is. The positive rate of the ADRB3 in breast cancer tissues of stage I is 65.0% (13/20). The positive rate in breast cancer tissues of stage III is 100% (67/67). The ADRB3 reduces the survival rate of breast cancer patients, and the survival time of breast cancer patients with positive expression of the ADRB3 is significantly less than that of breast cancer patients with negative expression of the ADRB3. The Kaplan-Meier survival curve of 142 breast cancer patients shows that, the survival rate of patients with negative ADRB3 in cancer tissues is significantly higher than that of patients with positive ADRB3 in cancer tissues, P=0.025. The mean survival of the two groups is respectively 154 months and 126 months. As can be seen from the survival curve, the survival rate of patients with positive ADRB3 gradually is decreased over time, and is about 60% approximately by 170th month. However, the survival rate of patients with negative ADRB3 is more slowly decreased than that of patients with positive ADRB3, and is still more than 90% by 170th month. The risk level curve also has a very obvious trend, that is, as time passes, the patients with positive ADRB3 experience increasingly more mortality risks on survival, which are about 5 times that of the original risks (0 month) by 170th month. The mortality risk of patients with negative ADRB3 is less than that of patients with positive ADRB3, and is less than 1 time that of the original mortality risk by 170th month. The correlation coefficient between ADRB3 and Ki67 in cancer tissues is 0.296 (P=0.02), and there is significant linear positive correlation.

(2) The ADRB3 expression in lung cancer tissues is significantly higher than that in normal lung tissues (P<0.01). The more the ADRB3 is expressed, the shorter the survival time is. The Kaplan-Meier survival curve shows that, the survival rate of patients with weakly positive ADRB3 in lung cancer tissues is significantly higher than that of patients with strongly positive ADRB3 in cancer tissues, P=0.038. The median survival time of patients with weakly positive ADRB3 is 81 months, and that of patients with strongly positive ADRB3 is 50 months. The ADRB3 level in cancer tissues is directly related to the rapid deterioration of lung cancer and poor prognosis. The ADRB3 antibody reduces the ADRB3 expression in cancer, and can be used to treat patients with lung cancer metastasis.

(3) The ADRB3 expression level in pancreatic cancer tissues is significantly higher than that in paracancerous tissues (P<0.01); and the survival rate of patients (0) with negative ADRB3 in cancer tissues is significantly higher than that of patients (1) with positive ADRB3 in cancer tissues, P=0.019. The mean survival time is 43.6 months for negative patients and 29.4 months for positive patients.

(4) The ADRB3 expression in colon cancer tissues is significantly higher than that in normal colon tissues (P=0.0001).

(5) The ADRB3 expression in hepatocellular carcinoma tissues is positively correlated with age and pathological grading. The older the age is and the higher the malignancy degree is, the more the ADRB3 proteins are. The expression level of ADRB3 in cancer tissues of liver cancer patients of more than 50 years old is significantly higher than that in paracancerous tissues, P=0.04. The Kaplan-Meier survival curve of 162 hepatocellular carcinoma patients shows that, the survival rate of patients with negative ADRB3 in cancer tissues is significantly higher than that of patients with positive ADRB3 in cancer tissues, P=0.038. The median survival time of patients with negative ADRB3 is 37 months, and that of patients with positive ADRB3 is 25 months.

(6) In patients suffering a relapse of acute lymphocytic leukemia, cytoplasm of bone marrow granulocytes contains a lot of dense rough-surfaced endoplasmic reticulums, ADRB3 and Ki-67 are adhered to the endoplasmic reticulums; ADRB3 and Ki-67 contents are increased significantly, and are significantly higher than the contents after complete response.

(7) The ADRB3 expression in cancer tissues of kidney cancer, thyroid cancer, colon cancer, esophagus cancer and gastric cancer is higher than that in paracancerous tissues.

Example 3 Immunofluorescence Detection of ADRB3 Expression in Cells in Bone Marrow Smears of Different Leukemia Patients 1. The test method is the same as that in Example 1.
2. The results are shown in FIG. 27 to 33:

(1) Myeloperoxidase (MPO) is a marker protein of neutrophils, and ADRB3 is expressed in neutrophils of normal subjects, but is not expressed in lymphocytes. The intracytoplasm ADRB3 of neutrophils forms a conical structure directly reaching the cytoblast, the channel formed by ADRB3 helps extracellular material (e.g., virus) to enter the cytoblast, blocks ADRB3, and will inhibit viruses' entry into the cytoblast. In patients with B lymphocytic leukemia, ADRB3 is expressed in both leukemia cells and neutrophils, suggesting that ADRB3 induces carcinogenesis of B-lymphocytes. The ADRB3 in leukemia cells also forms a channel directly reaching the cytoblast.

(2) Bone marrow smears of normal subjects injected with granocyte (recombinant human granulocyte colony-stimulating factor) are stained with ADRB3 and MPO. Granulocyte colony-stimulating factor stimulates granulocyte proliferation, most granulocytes are in proliferation phase, and the ADRB3 is highly expressed in immature granulocytes of proliferation phase, suggesting that the ADRB3 stimulates granulocyte proliferation to inhibit its differentiation and maturation. Due to the granulocyte colony-stimulating factor, the ADRB3 is expressed in lymphocytes (MPO negative), suggesting that the ADRB3 expression is inductive, and ADRB3 has the effect of regulating lymphocyte proliferation and differentiation.

(3) Bone marrow smears of patients with acute B-lymphoblastic leukemia suffering a relapse after treatment are stained with ADRB3 and MPO. In granulocytes and leukemia cells of patients suffering a relapse of leukemia after treatment, the ADRB3 is highly expressed, granulocytes containing a lot of ADRB3 are the key factors resulting in the relapse of the B-lymphocytic leukemia, and the ADRB3$^+$ granulocytes will promote leukemia cells at G0 phase to enter proliferation phase, thereby resulting in relapse. The ADRB3 expression in granulocytes and leukaemia cells of patients with acute B-lymphoblastic leukemia after treatment is reduced, compared with that before treatment. The ADRB3 aggregates in a site where granulocytes (antigen presentation cells) and lymphocytes contact with each other, which contributes to the stability of intercellular adhesion molecules, and promotes to form inhibitory immune synapses. The ADRB3 induces fusion of granulocytes with leukemia cells, alters the phenotype of cancer cells, increases the malignancy degree of cancer cells, and makes cancer cells be resistant to drugs. The ADRB3 in lymphocytes shows a conical structure directly reaching the cytoblast, affects the epigenetic modification and gene expression profile of lymphocytes, and promotes proliferation.

(4) Bone marrow smears of patients with acute B-lymphoblastic leukemia suffering a relapse after treatment are stained with ADRB3 and Ki-67. The ADRB3 and Ki-67 are highly expressed in granulocytes, and are co-localized in cytoplasm, suggesting that the granulocytes have vigorous ribosomal functions, and synthesize a lot of cell growth factors. By releasing the growth factor, the lymphocytes and tumor cells at G0 phase are stimulated to enter the proliferation phase. MDSC is a granulocyte of positive ADRB3 and positive Ki-67, and can inhibit T cells, NK cells and other immune cells to eliminate leukemia cells and other tumor cells. In the bone marrow and peripheral blood of patients suffering a relapse of leukemia after treatment, ADRB3$^+$ and Ki-67$^+$ granulocytes are significantly increased, suggesting that the granulocytes are the key to the relapse of leukemia.

(5) The ADRB3 is expressed in both granulocytes and leukemia cells of bone marrow smears of patients with acute monocytic leukemia (M5) after CR by treatment.

(6) The ADRB3 is highly expressed in granulocytes in proliferation phase (Ki-67 positive) of patients with acute myelocytic leukemia.

Example 4 Preparation of Hybridoma Cell Strains, Purification of ADRB3 Antibody, Antibody Sequencing and Humanization 1. Mice were immunized with human ADRB3 protein fragments (including full length), and some adopted epitopes are shown in FIG. 34A, including but not limited to the following antigenic epitopes: human ADRB3 full-length protein (1st-408th amino acid residues), N-terminal fragments (1st-155th amino acid residues) in ADRB3 protein, C-terminal fragments (156th-408th amino acid residues) in ADRB3 protein, leucine zipper fragment (296th-317th AA) in ADRB3 protein, nuclear localization sequence (NLS) (351st-369th AA), E1 (1st-36th amino acid residues in ADRB3), E2 (101st-111th amino acid residues in ADRB3), 12 (134th-155th amino acid residues in ADRB3), E4 (315th-326th amino acid residues in ADRB3), 14 (348th-408th amino acid residues in ADRB3), etc. The BALB/c mice were injected subcutaneously with Freund's complete adjuvant, and were intensively immunized via caudal vein 21 days after the first immunization. 4 days later, spleen cell suspension was prepared for cell fusion with myeloma cell SP2/0, hybridoma cell was screened using HAT, hybridoma was cloned, finally a few hybridoma cell trains of each ADRB3 protein fragment were obtained, and more than 30 hybridoma cell strains that can produce ADRB3 antibodies were screened. The specificity and affinity of antibodies were detected using enzyme-linked immunosorbent assay (ELISA), protein immunoblotting (FIG. 34B) and immunofluorescence test. After lysing hybridoma cells by Trizol, RNA was extracted for light and weight chain sequencing of antibodies. Light chain plasmids (nucleic acid and protein sequences as shown in FIG. 35, but not limited to FIG. 35) and heavy chain plasmids (nucleic acid and protein sequences as shown in FIG. 36, but not limited to FIG. 36) of humanized antibodies were constructed. HEK293 was transfected using BPfectin Transfection Reagent at H:L=1:1 at a ratio of transfected reagents to plasmids of 3:1, and cultured in a bioreactor to produce a lot of antibodies.

Collecting antibody from ascites of mice: Balb/c mice of 10-11 weeks old were intraperitoneally injected with a complete immune adjuvant with 0.1 ml/mouse, and were intraperitoneally injected with hybridoma cells $5*10^6$ 6 days later. The ascites was taken out once every other day since 8th day after cell inoculation. After centrifugation at 3000 rmp for 10 min, the supernatant of ascites was stored at $-80°$ C. After concentration with ammonium sulfate, it was purified by Protein G affinity chromatography columns, and purified and eluted according to a standard antibody purification method to identify the purity by SDS-PAGE. Its quantity was measured by UV.

Example 5 MTT Assay for Detection of Anti-Cancer Effect of ADRB3 Monoclonal Antibody 1. Test Steps:
(1) After trypsinization, adherent tumor cells in logarithmic growth phase were prepared into 5000/ml cell suspension using RPMI 1640 medium containing 10% calf serum, inoculated into a 96-well culture plate with 200 l/well, and cultured at 37° C. under 5% $CO_2$ for 24 h. (2) A new medium containing different concentrations of the ADRB3 monoclonal antibody was replaced for the experimental group, a medium containing equivalent volume of solvent was replaced for the control group, and 3-5 parallel wells were established for each group. They were cultured at 37° C. under 5% $CO_2$ for 4-5 days. (3) After the supernatant was abandoned, 200 µl of a fresh serum free medium containing 0.5 mg/ml MTT was added to each well, and then culture was continued at 37° C. for 4 h. After the supernatant was carefully discarded, 200 µl of DMSO was added, and fully mixed with a minitype ultrasonator to measure the optical density value with an ELIASA at a wavelength of 570 nm and a reference wavelength of 450 nm.

2. The Test Results are Shown in FIGS. 37A-39 and 52-56:
The ADRB3 monoclonal antibody dose-dependently decreases the activity of human breast cancer cells MCF7, pancreatic cancer cells SW1990 and CFPAC1, lung cancer cells A549, lung cancer cells H1299, hepatic cancer cells HepG2, colon cancer cells HCT116, promyelocytic leukemia cells HL-60 and glioma cells U251. Compared with the control group, *P<0.05, #P<0.01.

Example 6 ADRB3 Monoclonal Antibody Inhibits Proliferation of Tumor Transplanted into Nude Mice 1. Test Method
Female nude mice of 5 weeks old were subcutaneously injected with human tumor cells or mice 4T1 breast cancer cells near their breasts, each of which was injected with $5*10^6$ cells. Human tumor cells include MCF7, CFPAC1, ASPC1, SW1990, A375, A549, etc. 8-10 days later, the transplanted tumors were about 100 $mm^3$, and were randomly divided into antibody group and control group with 8 mice in each group. The antibody group was intraperitoneally injected with the ADRB3 antibody in a dose range of 1-10 mg/kg once every other 3 days, and the length and width of the tumor were measured. The control group was intraperitoneally injected with mouse IgG. When the tumor volume of the control group reached the maximum volume permitted by the Animal Ethics Committee, blood was taken out the orbit, the cervical vertebrae were removed to kill nude mice, and the transplanted tumor and spleen were stripped to get the tumor weight, spleen weight and body weight. The spleen index was calculated as follows: spleen index=spleen weight (mg)/mouse weight (g).

2. The Test Results are Shown in FIGS. 37 and 40-51:
(1) The ADRB3 monoclonal antibody inhibits proliferation of the tumor transplanted with the breast cancer cell MCF7 in nude mice. Compared with control group, *P<0.05, #P<0.01. The spleen of mice in the ADRB3 antibody group is significantly larger than that of mice in the control group. The ADRB3 antibody increases the spleen index, and has the function of contributing to development and maturation of immune organs. HE staining of transplanted tumor shows that the ADRB3 antibody decreases neutrophil infiltration in transplanted tumor. After HE staining of the spleen tissue, the spleen in the control group does not have a clear dividing line, there is not a clear dividing line between white pulp and red pulp, and a large number of neutrophils can be seen. The ADRB3 antibody increases the splenic corpuscle and the germinal center, and reduces the count of neutrophils in the spleen. Immunohistochemical analysis shows that the ADRB3 antibody reduces the expressions of ADRB3, P62, Cyclin D1, MPO, Neutrophil Elastase, p-Rb (S780), CDK3 and IL-6 in transplanted tumor cells and infiltrating neutrophils, and reduces the activity of CDK3.

(2) The ADRB3 antibody reduces the growth of tumor transplanted with the pancreatic cancer cell CFPAC1 in nude mice. Compared with the control group, *P<0.05. The ADRB3 antibody reduces the weight of tumor transplanted with CFPAC1 cells, doesn't affect the body weight of the nude mice transplanted with CFPAC1, and increases the spleen index. HE staining shows that the ADRB3 antibody decreases neutrophil infiltration in transplanted tumor. Immunohistochemical analysis shows that the ADRB3 antibody reduces the expressions of ADRB3, Cyclin D1, Neutrophil Elastase, p-Rb (S780), p-mTOR (S2481), Rictor, HK2, CDK3 and IL-6 in transplanted tumor cells and infiltrating neutrophils.

(3) The ADRB3 antibody reduces the growth of tumor transplanted with the pancreatic cancer cell ASPC1 in nude mice. Compared with the control group, *P<0.05. The ADRB3 antibody reduces the weight of tumor transplanted with ASPC1 cells, and doesn't affect the body weight of the nude mice transplanted with ASPC1.

(4) The ADRB3 antibody inhibits the proliferation of tumor transplanted with the pancreatic cancer cell SW1990, increases the apoptosis rate of SW1990. Compared with the control group, *P<0.05. The ADRB3 antibody decreases the count of neutrophils in the tumor bearing mice and the neutrophil-lymphocyte ratio (NLR). Compared with the control group, *P<0.05. The ADRB3 antibody increases the spleen index.

(5) The ADRB3 antibody inhibits proliferation of the tumor transplanted with the melanoma cell A375. Compared with the control group, *P=0.032, #P=0.005. The ADRB3 antibody reduces the number of MSDC in the peripheral blood of nude mice transplanted with A375. HE staining and immunohistochemical analysis show that there are a lot of neutrophil infiltrations in A375-transplanted tumor of the control group, PD-L1 is highly expressed in neutrophils, and the ADRB3 antibody decreases neutrophil infiltrations in A375-transplanted tumor. Immunohistochemical analysis shows that the ADRB3 antibody inhibits the expressions of ADRB3, IL-6, MPO, Neutrophil Elastase, PD-L1, p-Rb (Ser 780), p-mTOR (2481), Rictor, HK2 and CDK4 in A375-transplanted tumor cells and infiltrating neutrophils. After treatment with the antibody, no PD-L1 is expressed in the neutrophils infiltrated in the transplanted tumor. ELISA of inflammatory factors in the serum shows that, the ADRB3 antibody increases the concentration of IL-10, but reduces the concentrations of IL-6, VEGF and MPO in the serum of mice. The ADRB3 antibody specifically inhibits the expression and activity of ADRB3, thereby inhibiting neutrophil-mediated inflammatory response, altering the microenvironment of tumor and playing an anti-cancer role.

(6) The ADRB3 antibody increases the spleen index, and inhibits proliferation of the tumor transplanted with the human lung cancer cell A549. Compared with the control group, *P<0.05. HE staining shows that the ADRB3 antibody decreases neutrophil infiltration in transplanted tumor. Immunohistochemical analysis shows that the ADRB3 antibody reduces the expressions of ADRB3, Cyclin D1, Neutrophil Elastase, p-Rb (Ser 780), p-mTOR (Ser 2481), Rictor, HK2, CDK3 and IL-6 in transplanted tumor cells and infiltrating neutrophils.

(7) The ADRB3 antibody reduces proliferation of the tumor transplanted with the breast cancer cell 4T1 in mice, and inhibits liver metastasis of 4T1 cells. 8 mice in the control group all had serious liver metastases, and the liver metastasis in the antibody group was obviously less than that in the control group. The ADRB3 promotes liver metastasis of 4T1 cells, and can be blocked to inhibit liver metastasis. The ADRB3 antibody increases the spleen index, reduces the count of blood neutrophils, increases the ratio of lymphocytes in WBC, and reduces NLR. NLR is an index of systemic inflammatory response, and an increase of NLR is an independent risk factor of poor prognosis in tumor patients. The ADRB3 antibody reduces NLR, indicating that this antibody can inhibit inflammation and improves prognosis of patients.

Example 7 T-Lymphocytes Modified by ADRB3 Specific Chimeric Antigen Receptor can Kill Cell SW1990 (A1) and Cell H1299 (C3)

1. Test Method

The ADRB3 chimeric antigen receptor consists of a single chain antibody of an anti-human ADRB3, a CD8 hinge area and transmembrane zone, an intracellular signal area of CD137 (also known as 4-1BB) and an intracellular signal structure of CD3ζ in series. According to the sequencing results of the ADRB3 monoclonal antibody, a lentivirus expression vector of chimeric antigen receptors was constructed, including lentiviruses. The primitive generation T cells were isolated, and recombinant CAR-T cells were constructed using the above lentivirus. Target cells SW1990 (A1) and H1299 (C3) were inoculated into a 96-well plate with 50,000 cells/well for overnight cultivation. Then, the CAR-T cells were added at the effect/target ratio (E/T) as shown in the figure, and were co-cultured for 6 hours. After centrifugation, the supernatant was detected with the LDH kit. Target cells in wells without adding CAR-T were pyrolyzed and then used as the maximal lysis, and target cells in wells that were not pyrolyzed were used as the minimal lysis.

2. Test Results

Figure 57:
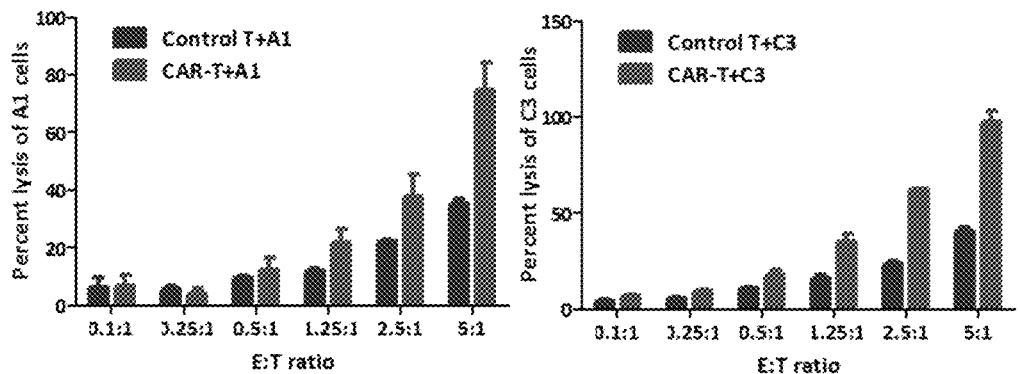
FIG. 57: T-lymphocytes modified by ADRB3 specific chimeric antigen receptor can kill cell SW1990 (A1 in the left figure is SW1990) and cell H1299 (C3 in the right figure).
Figure 58:
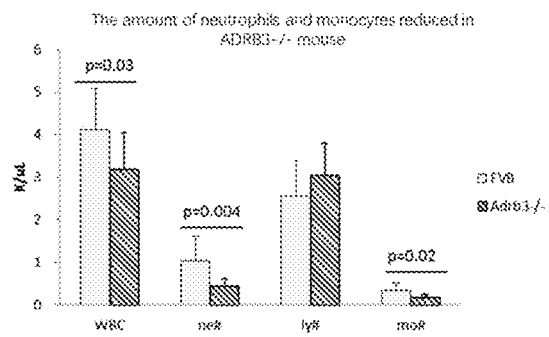
FIG. 58: the total counts of leukocytes, neutrophils and monocytes in the peripheral blood of the ADRB3 knockout mice are reduced; WBC: leukocytes, ne #: neutrophils, ly #: lymphocytes, and mo #: monocytes.
Figure 59:
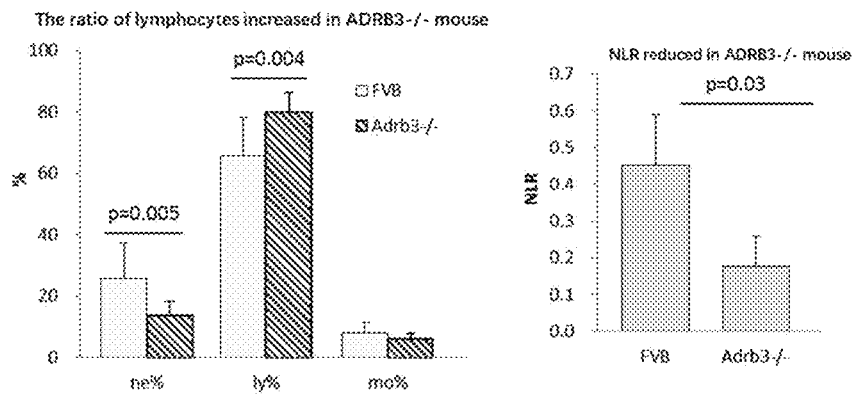
FIG. 59: in the ADRB3 knockout mice, the percentage of lymphocytes is increased, that of neutrophils is decreased, and NLR is decreased; ly %: percentage of lymphocytes; ne %: percentage of neutrophils, and mo %: percentage of monocytes.
Figure 60:
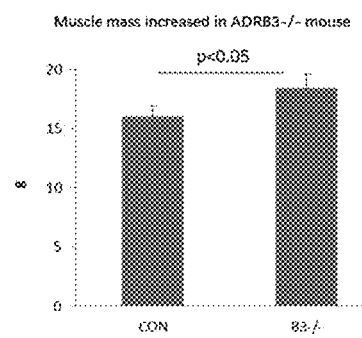
FIG. 60: the muscle amount of the ADRB3 knockout mice is increased.
Figure 61:
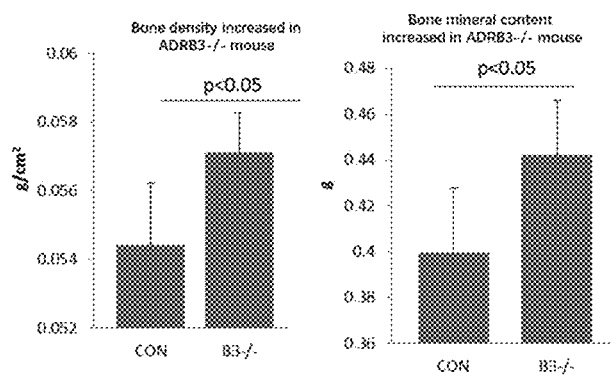
FIG. 61: both the bone density and bone mineral content of the ADRB3 knockout mice are increased.
Figure 62:
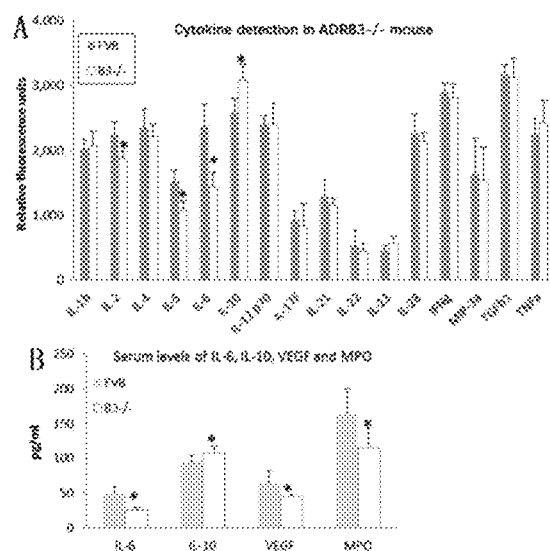
FIG. 62: A. detection of serum cytokine in the ADRB3 knockout mice, Relative Fluorescence Units; compared with the control group, *P<0.05; B. ELISA of serum in ADRB3$^{-/-}$ mice; IL-10 in serum of ADRB3$^{-/-}$ mice is increased, but IL-6, VEGF and MPO are decreased.
Figure 63:
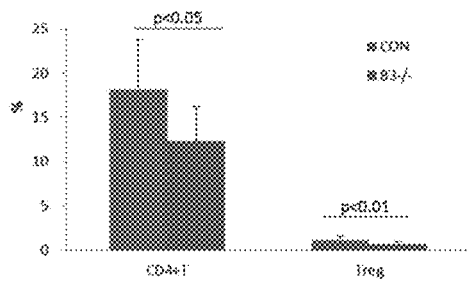
FIG. 63: flow cytometry for detection of CD4$^+$T cells and Treg cells in the spleen of the ADRB3 knockout mice.
Figure 64:
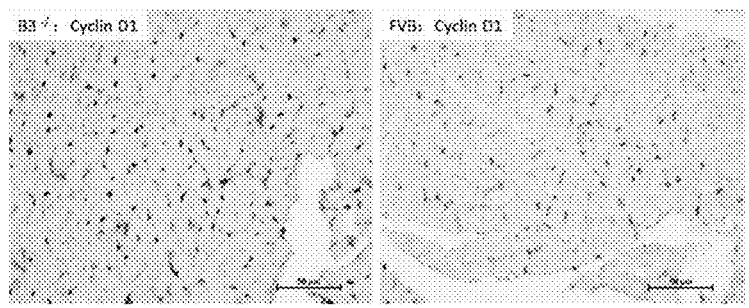
FIG. 64: immunohistochemical analysis on the myocardium Cyclin D1 of the ADRB3 knockout mice. FVB mice are normal control.
Figure 65:
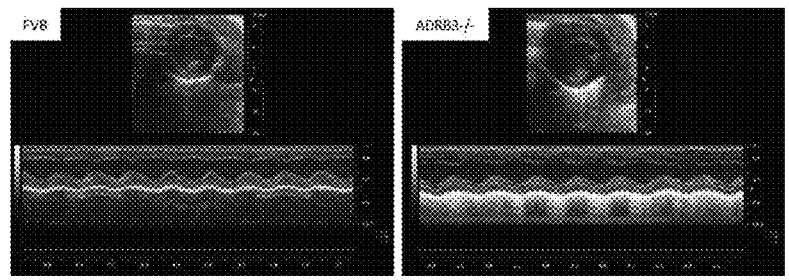
FIG. 65: cardiac B ultrasound examination of the ADRB3 knockout mice; and after knocking out the ADRB3, the heart function is good. FVB mice are normal control.
Figure 66:
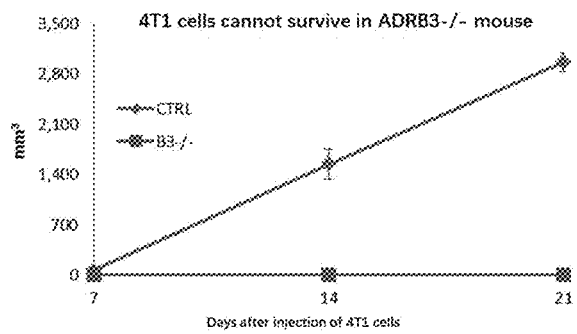
FIG. 66: the mouse breast cancer cell 4T1 cannot grow subcutaneously in the ADRB3 knockout mice. FVB mice are normal control.
Figure 67:
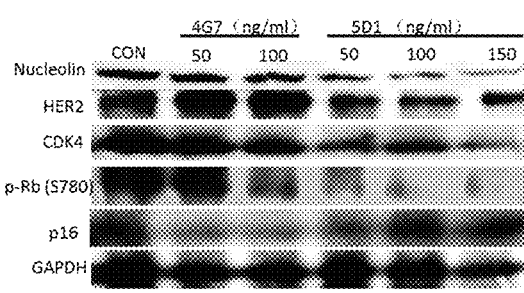
FIG. 67: the ADRB3 antibody decreases the expressions of CDK4, nucleolin, HER2 and p-Rb (Ser780), but increases the expression of p16.
Figure 68:
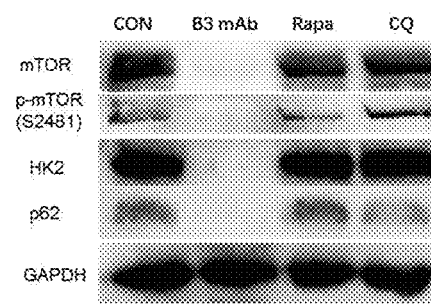
FIG. 68: the ADRB3 antibody decreases the expressions of mTOR, p-mTOR (Ser2481), HK2 and P62; and *Rapa* is rapamycin, and CQ is chloroquine.
Figure 69:
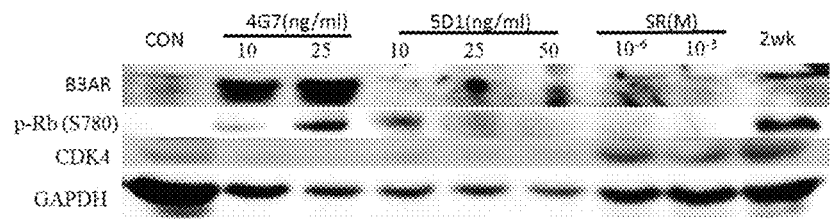
FIG. 69: the 5D1 antibody decreases the expressions of ADRB3, p-Rb (Ser780) and GAPDH; 4G7 increases the expressions of ADRB3 and p-Rb (Ser780); either of the two antibodies can decrease the expressions of GAPDH and CDK4; and SR (SR59230A) is an ADRB3 inhibitor.
Figure 70:
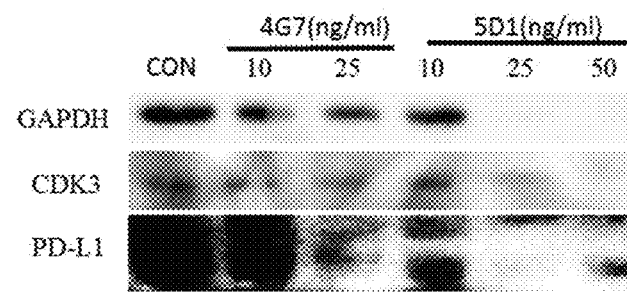
FIG. 70: the 5D1 antibody decreases the expressions of PD-L1, CDK3 and GAPDH.
Figure 71:
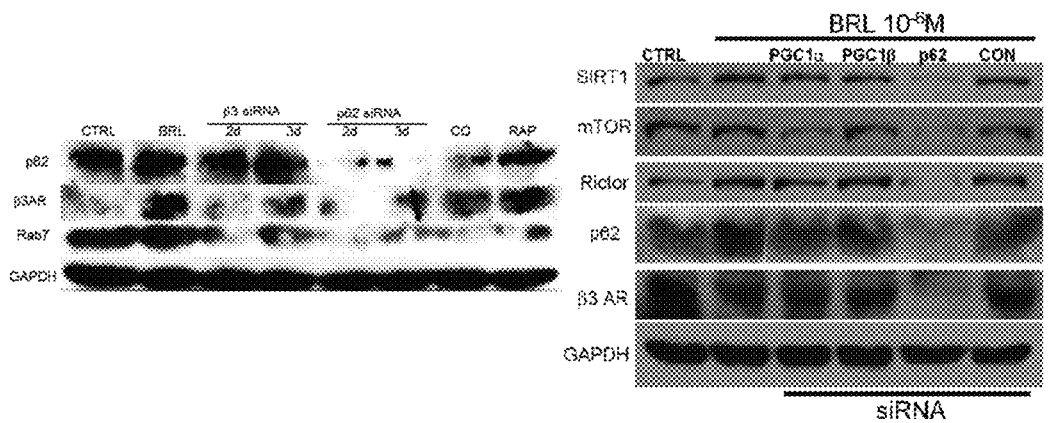
FIG. 71: after inhibiting p62, siRNA decreases the expressions of ADRB3 and Rab7; rapamycin increases the expression of ADRB3; after silencing p62, ADRB3 cannot increase the expressions of mTOR, Rictor, SIRT1 and ADRB3.
Figure 72:
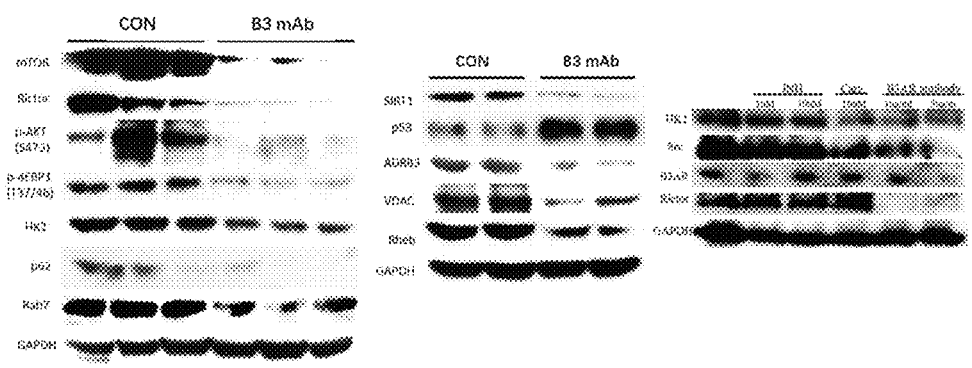
FIG. 72: the ADRB3 antibody decreases the expressions of mTOR, Rictor, p-AKT (Ser 473), p-4EBP1 (T37/46), HK2, P62, Rab7, SIRT1, ADRB3, VDAC and Rheb, but increases the expression of p53 in MCF7 tumor transplanted into nude mice.
Figure 73:
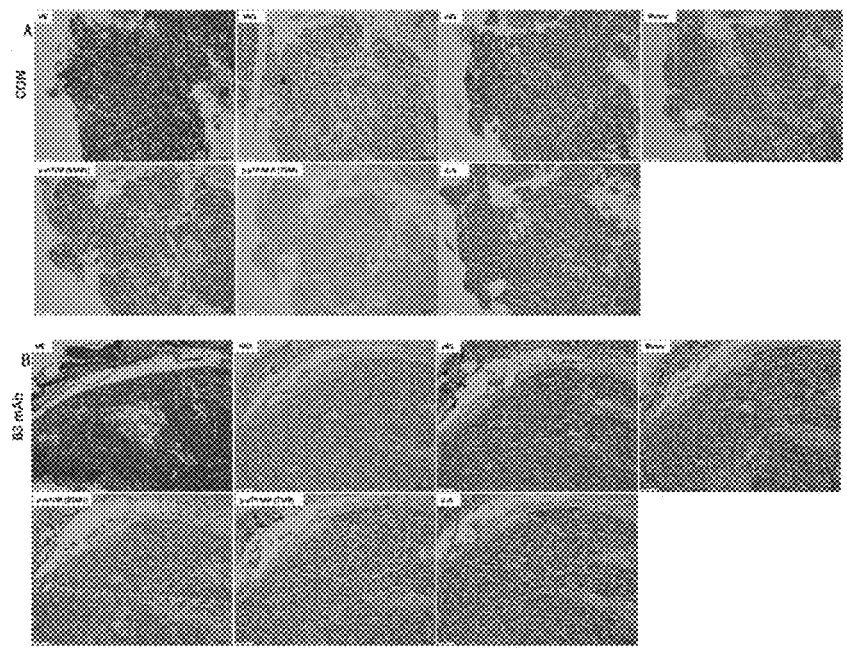
FIG. 73: the ADRB3 antibody decreases the expressions of HK2, P62, p-mTOR (S2481), Rictor and IL-6 in MCF7 tumor transplanted into nude mice; A. control group, B. antibody group.
Figure 74:
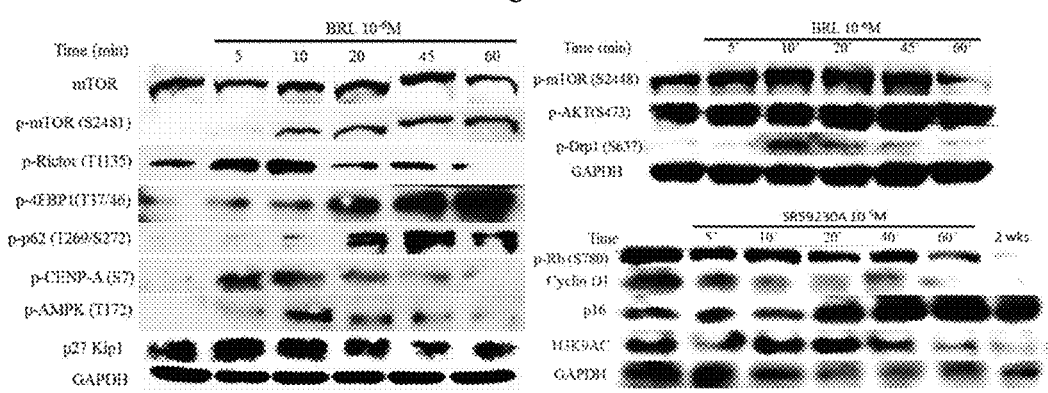
FIG. 74: after agitation, the ADRB3 increases phosphorylation of the proteins, such as mTOR, Rictor, 4EBP1, CENPA, P62, Drp1, AKT and AMPK in downstream signal paths.
Figure 75:
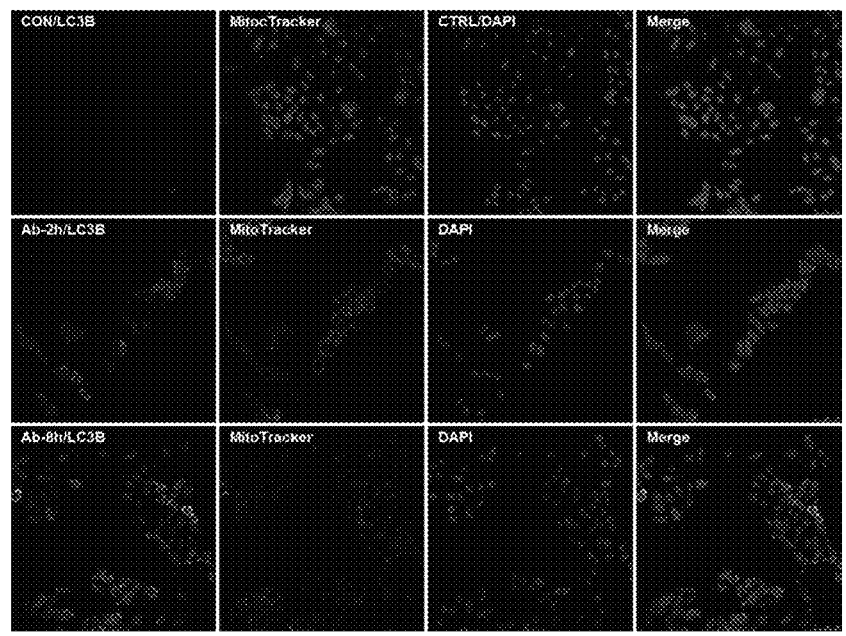
FIG. 75: The ADRB3 antibody inhibits elimination of the autophagosome of the MCF7 mitochondria.
Figure 76:
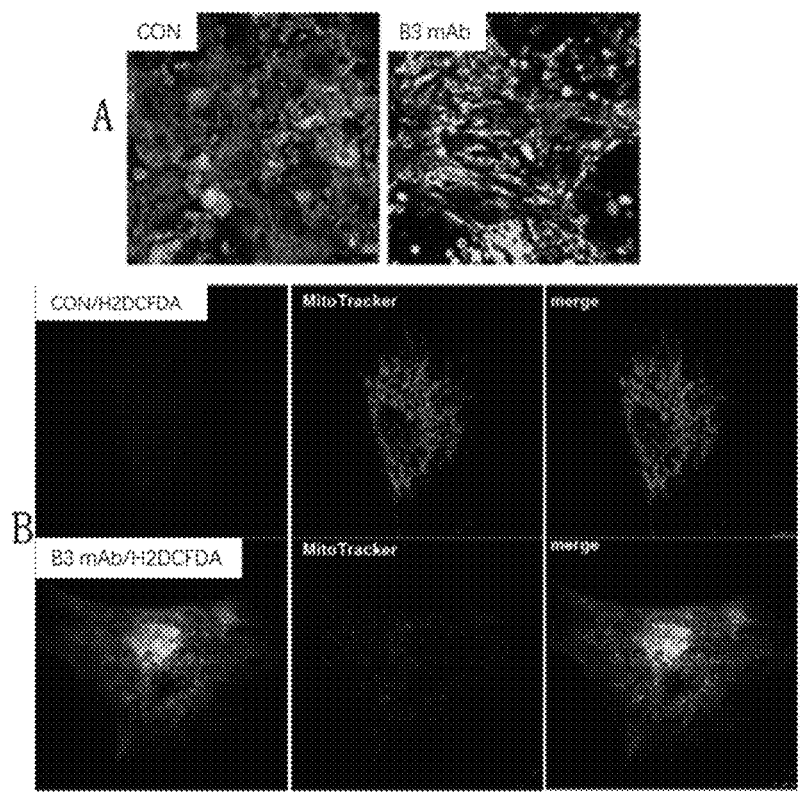
FIG. 76: A. the ADRB3 antibody reduces the mitochondrial membrane potential, which is reflected as green after JC1 staining, and B. the ADRB3 antibody increases the reactive oxygen in MCF7.
Figure 77:
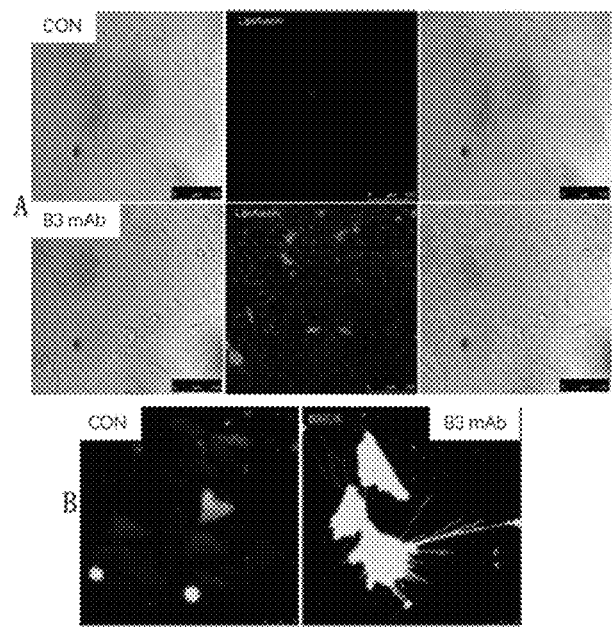
FIG. 77: A. the ADRB3 antibody increases the intracellular content of lipofuscin; and B. the ADRB3 antibody increases the intracellular content of 5-CFDA in MCF7 cells.
Figure 78:
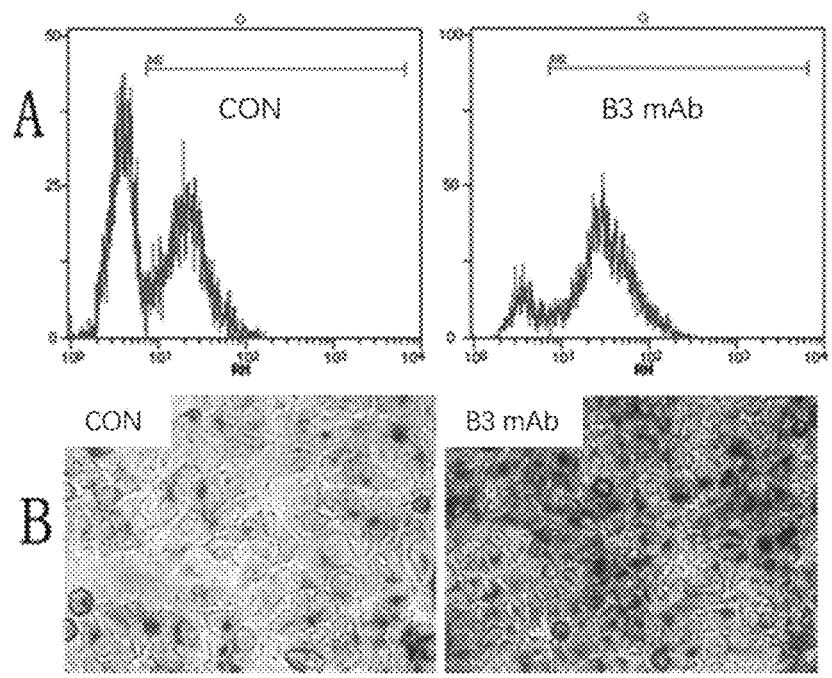
FIG. 78: A. the ADRB3 antibody increases the intracellular content of rhodamine 123 in MCF7 cells; B. the ADRB3 antibody increases the intracellular content of SA-β-Gal (senescence-associated β-galactosidase).

Half of the effective E/T of H1299 is 2:1, and half of the effective E/T of SW1990 is 2.5:1 (FIG. 57). An ADRB3 chimeric antigen receptor-modified T-lymphocyte can kill ADRB3 positive tumors, and is used for treating a lung cancer and a pancreatic cancer. The anti-ADRB3 CAR-T cell is specific to tumor cells and inflammatory cells (neutrophils, Treg and macrophages) in the internal environment of a tumor. Even if ADRB3 is not expressed in tumor cells, the CAR-T cell can still inhibit cells in a tumor environment to play an anti-cancer role, is a universal CAR-T cell, and is applicable to treatment of all malignant tumors and inflammatory diseases.

Example 8 Experiment of ADRB3 Knockout Mice

1. Test Method

Peripheral blood was taken from 15 male ADRB3 knockout mice of 16 weeks old and 15 male normal FVB mice of 16 weeks old for blood routine and blood biochemistry. The serum cytokines were detected using a cytokine antibody chip (QAM-TH17-1, Quantibody® Array Glass Chip) of mice cell TH17, and signals were scanned using a laser scanner Axon GenePix. Bone density, fat and muscle content were measured. Cardiac functions of ADRB3 knockout mice of 10, 30 and 70 weeks old (8 mice of each age) were detected by cardiac B3 ultrasound examination. The number and proportion of different subtypes of T cells and macrophages were detected by flow cytometry of peripheral blood cells and spleen cells. Immunohistochemical analysis was used to detect cardiac CDK3, cyclinD1, p-mTOR (Ser2448), p-mTOR (Ser2481) and p-4EBP1 (T37/46). The water maze test was used to research the learning and memory ability of mice.

10 female ADRB3 knockout mice of 12 weeks old and 10 female normal FVB mice of 12 weeks old were subcutaneously inoculated with $10^6$ mouse breast cancer cell 4T1 to form a transplanted tumor. Length, width and height of the tumor were measured once every other 3 days. After knocking out ADRB3 gene from MMTV-PyVT mice carrying a mouse breast cancer virus, the incidence of breast tumor in female mice was observed.

2. The test results are shown in FIG. 58-66: the ADRB3 gene of the mice was knocked out to detect the tumor formation of exogenous tumor cells. It was found that the immune system of the mice body was improved, and can destroy cancer cells. The breast cancer cell 4T1 formed tumors in normal FVB mice, but failed to form tumors in ADRB3$^{-/-}$ mice. The incidence of spontaneous tumors in old ADRB3$^{-/-}$ mice was significantly decreased. After knocking out ADRB3 gene from MMTV-PyVT mice, the incidence of breast tumor in female mice was significantly decreased. ADRB3 knockout mice have an extended life, and will not have an autoimmune disease or cancer.

(1) In the peripheral blood of ADRB3$^{-/-}$ mice, neutrophils were significantly reduced, the percentage of lymphocytes was decreased, NLR was decreased, and the mean volume of red blood cells was low. ADRB3 increases the counts of neutrophils and monocytes, but does not affect the counts of lymphocytes, decreases NLR by increasing the count of neutrophils, and increases the total counts of leukocytes.

ADRB3 increases the percentages of neutrophils and monocytes, but reduces the percentage of lymphocytes.

(2) The muscle amount of the ADRB3$^{-/-}$ mice is increased. Both the bone density and bone mineral content of the ADRB3 knockout mice are increased.

(3) In serum of the ADRB3$^{-/-}$ mice, inflammatory cells, such as IL-2, IL-4, IL-5, IL-6, IL-17F, IL-21, IL-22, TGF- and MIP-3, are decreased, but IL-10 is increased. ELISA of inflammatory factors in the serum shows that, the concentration of IL-10 in serum of the ADRB3$^{-/-}$ mice is increased, but the concentrations of IL-6, VEGF and MPO are reduced.

(4) CD4$^+$T cells and Treg cells in the spleen of the ADRB3$^{-/-}$ mice are significantly decreased.

(5) Cardiac B ultrasound examination of ADRB3$^{-/-}$ mice. The cardiac function of old ADRB3$^{-/-}$ mice is stronger than that of ADRB3 wild type old mice. The cardiac function of ADRB3$^{-/-}$ mice is not significantly decreased with the increase of age. Compared with the control group, the expressions of CDK3 and cyclinD1 in the myocardium of ADRB3$^{-/-}$ mice are increased, the mTORC2/4EBP1 pathway is activated and the ribosome of the myocardial cell is increased.

(6) Tumor cells and granulocytes produce and release ADRB3 into the blood to inhibit T-lymphocytes, destroy specific immunity of the organism and promote cancer cell growth. The anticancer effect caused by knockout of ADRB3 is due to enhancement of the anti-cancer activity of the immune system. Both neutrophils and Treg cells in ADRB3$^{-/-}$ mice are decreased, but CD8$^+$T cells are increased, thereby enhancing the immune surveillance and defense function of the organism.

(7) The learning and memory ability of ADRB3$^{-/-}$ mice is better than that of ADRB3 wild type mice.

Example 9 Treatment of Cells MCF-7/A549/SW1990 with Different Concentrations of ADRB3 Antibody 1. Test Method Cells MCF-7/A549/SW1990 were treated with different concentrations of ADRB3 antibody, and the control group was treated with mouse IgG. 24 h later, the cells were lysed and the total protein was extracted. BCA method was used to determine the protein concentration: 10 ug of protein was separated with 10% SDS PAGE, transferred to a PVDF membrane, and closed with 4% skim milk for 1 h to incubate primary antibody at 4° C. overnight. Then the secondary antibody was incubated for 1 h, and developed with ECL. The experiment was repeated 3 times. The gray values of the protein bands were analyzed with software Fluorchem 8900 to calculate the ratio of target band to internal reference band (GAPDH or actin). The transplanted tumor tissues in nude mice were examined by immunohistochemical analysis to detect the expressions of associated proteins mTOR, Rictor, p-AKT (S473), p-4EBP1 (T37/46), HK2, P62, Rab7, SIRT1, ADRB3, VDAC and Rheb in the ADRB3 signal transduction pathway.

2. The Test Results are Shown in FIG. 67-74:

(1) The ADRB3 antibody reduces the expressions of CDK4, nucleolin, HER2 and pRb, but increases the expression of P16 in cells MCF-7/A549/SW1990.

(2) The ADRB3 antibody dose-dependently reduces Rheb, mTOR, p-mTOR (S2481), HK2 and P62 in cells MCF-7/A549/SW1990.

(3) The ADRB3 antibody (5D1) reduces ADRB3, p-Rb (S780) and GAPDH in cells MCF-7/A549/SW1990. 4G7 increases ADRB3 and increases p-Rb (S780). Either of the two antibodies can reduce GAPDH and CDK4.

(4) The ADRB3 antibody reduces the expressions of PD-L1 and CDK3 in cells MCF-7/A549/SW1990.

(5) After designing siRNA silencing P62, the expressions of ADRB3 and Rab7 in cells MCF-7/A549/SW1990 are reduced. Rapamycin increases the expression of ADRB3. After expressing the silent P62, ADRB3 could not increase the expressions of mTOR, Rictor, SIRT1 and ADRB3.

(6) The ADRB3 antibody decreases the expressions of mTOR, Rictor, p-AKT (S473), p-4EBP1 (T37/46), HK2, P62, Rab7, SIRT1, ADRB3, VDAC and Rheb, but increases the expression of P53 in MCF-7 tumor transplanted into nude mice.

(7) The ADRB3 antibody decreases the expressions of HK2, P62, p-mTOR (S2481), Rictor and IL-6 in MCF-7 tumor transplanted into nude mice.

(8) after agitation, the ADRB3 increases phosphorylation of the proteins, such as mTOR, Rictor, 4EBP1, CENPA, P62, Drp1, AKT and AMPK in downstream signal paths of cells MCF-7/A549/SW1990.

Example 10 Mitochondrial Autophagy Test

1. Test Method

MCF-7 cells were treated using the ADRB3 antibody at a final concentration of 20 ng/ml, and was immobilized 2 h or 8 h later. After the mitochondria were stained with Mitotracker, LC3II expression was detected by immunofluorescence, and observed under a confocal microscope. After JC-1 (10 ug/ml) staining for 15 min, it was observed in a living cell state under a confocal microscope at excitation light wavelengths of 510 nm and 580 nm. ROS was stained with 10 uM H2DCFDA for 15 min, and observed under a confocal microscope. Intracellular lipofuscin was observed at a fluorescence of 488 nm. Cells were marked with 10 uM P-glycoprotein (P-gP) substrate 5-CFDA-AM, and observed under a confocal microscope at an excitation light wavelength of 510 nm. Cells were stained with rhodamine 123, and detected by flow cytometry. The expression of β-galactosidase in cell MCF7 was detected after in situ β-galactosidase staining.

2. The test results are shown in FIG. 75-78: the expression of LC3II in the ADRB3 antibody group is significantly increased with the extension of the action time. The ADRB3 antibody inhibits the elimination of mitochondrial autophagosome to accumulate the autophagosome in cells. ADRB3 promotes elimination of the autophagosome to ensure smoothly carrying out the process of mitochondrial autophagy. The ADRB3 antibody reduces the mitochondrial membrane potential, which is reflected as green after JC1 staining. The ADRB3 antibody increases intracellular ROS, lipofuscin and β-galactosidase. The ADRB3 antibody blocks autophagy, so that the autophagosome, damaged mitochondria, lipofuscin and other metabolic wastes are accumulated in cells, thereby reducing the cell activity, and accelerating cell aging and apoptosis. 5-CFDA staining shows that a lot of filamentous synapses grow from the cells, and also indicates that the cells are aging. The ADRB3 antibody increases the contents of 5-CFDA and rhodamine 123 in MCF-7, indicating that the ADRB3 antibody reverses multidrug resistance of MCF-7 cells.

Example 11 ADRB3 Antibody Reduces Glucometabolism in Tumor Tissues

1. Test Method

After being treated with the ADRB3 antibody for 5 weeks, MCF-7 tumor-bearing mice were injected with 18F-FDG via caudal vein at a dose of 1 millicurie (mCi)/mouse. 50 minutes later, the mice were anesthetized with a mixed gas of 3% isoflurane and oxygen (1 L/min) to dynamically acquire images by PET/CT scan in the supine position and iteratively reconstruct images by 18F-FDG tumor metabolic imaging. The gray values of target tissues (T) and adjacent normal tissues (non-target tissues N) on reconstructed images were analyzed with software Fluorchem 8900 to calculate the value of T/N. The transplanted tumor tissues were homogenized in ice pre-cooled RIPA lysis buffer and at a high speed, and the ATP content and the activity of hexokinase (HK) in the tissues were detected with a corresponding kit.

Figure 79:
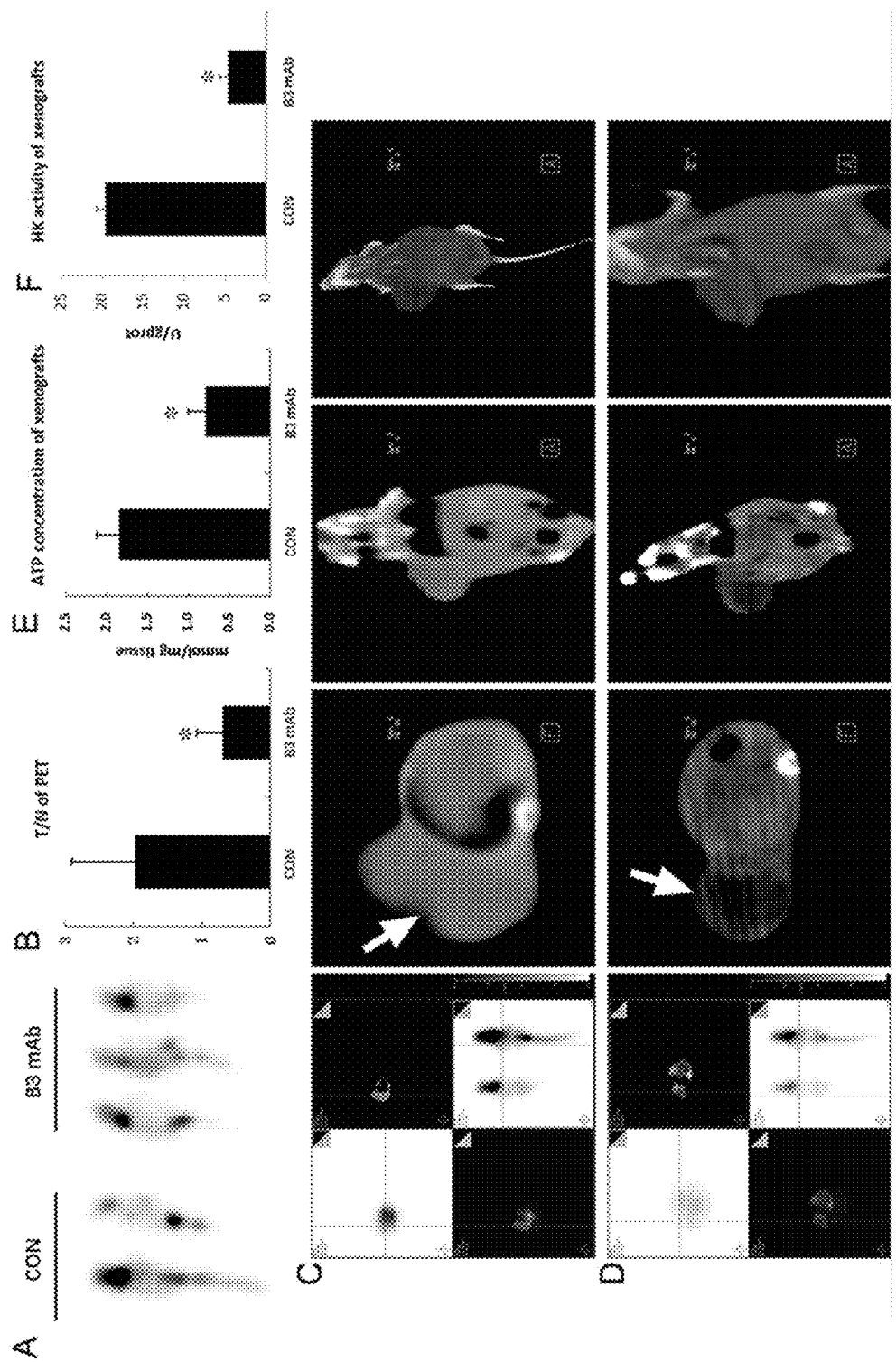
FIG. 79: the ADRB3 antibody reduces uptake of 18F-FDG by tumor tissues transplanted with MCF7 in nude mice; (A) 18F-FDG PET scannogram; (B) histogram of the gray scale ratio of target tissues (T) to adjacent normal tissues (non-target tissues N) on a reconstructed image; (C) control group: the transplanted tumor has a radioactive concentrated image. The tumor has similar uptake of FDG to liver without central necrosis, and the white arrow means transplanted tumor; (D) ADRB3 antibody group: the transplanted tumor has radioactive sparseness and defect in the middle thereof. The tumor has less uptake of FDG than liver with central liquefaction necrosis; (E) the ADRB3 antibody decreases the ATP output of tumor tissues; and (F) the ADRB3 antibody decreases the HK activity of tumor tissues.

2. The test results show that (as shown in FIG. 79): radiative accumulation is observed at the transplanted tumor site in the control group, and the radioactivity at the transplanted tumor site in the ADRB3 antibody group is reduced by about 60% (0.78+0.44 vs 1.96+0.94, P<0.01), compared with that in the control group. The ADRB3 antibody reduces the output of ATP in tumor tissues, and the activity of HK in tumor tissues.

Example 12 Observation of Mitochondria and Autophagosome of Transplanted Tumor Cells Under a Transmission Electron Microscope 1. Test Method The transplanted tumor was immobilized in 2.5% glutaraldehyde, and cut into about 1 mm$^3$ tissue blocks to prepare samples for electron microscope. After dehydration, penetration and embedment, samples were sliced with a Reichert ultra-thin slicing machine to obtain 70 nm slices, which were stained with lead citrate solution for 15 min, stained with 50% ethanol saturated solution of uranyl acetate for 15 min, and observed under a FEI (Czech Republic) transmission electron microscope.

2. Test Results

Figure 80:
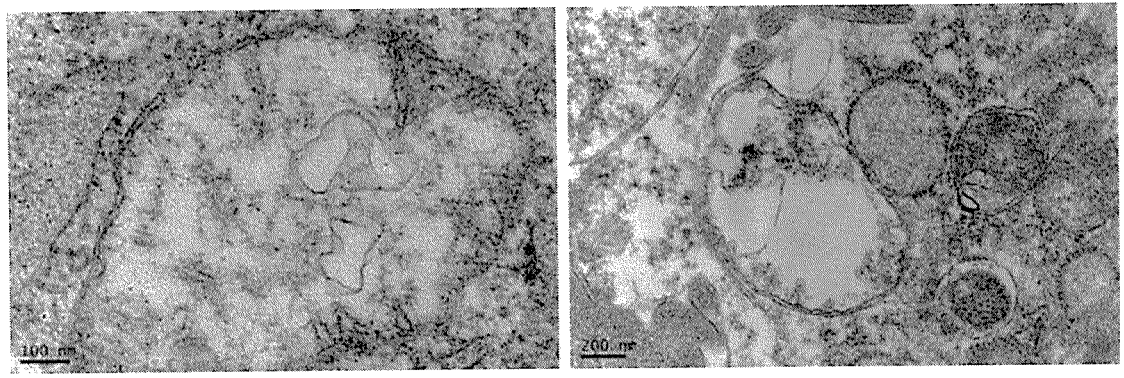
FIG. 80: TEM of the tissue of the tumor transplanted with MCF7 cells of the ADRB3 antibody group, and the ADRB3 antibody results in mitochondrial *crista* decrease and volume expansion.
Figure 81:
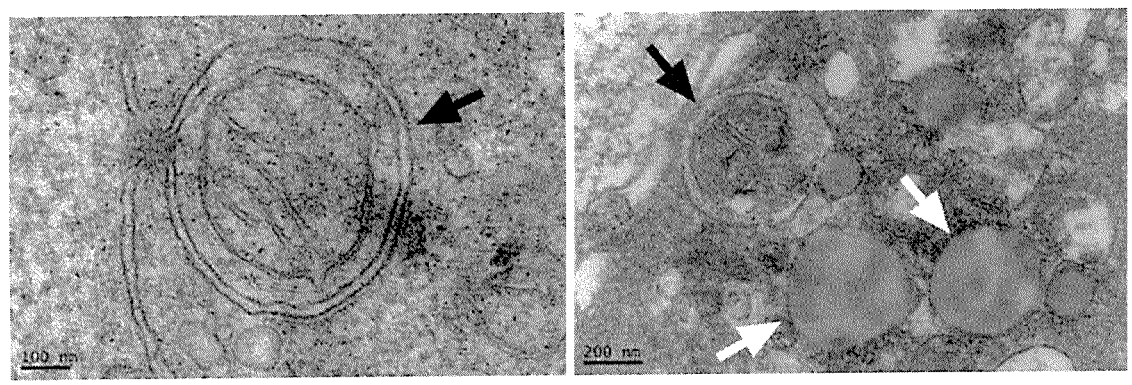
FIG. 81: in tumor cells transplanted with MCF7 cells of nude mice of the ADRB3 antibody group, mitochondrial autophagosome is accumulated in cytoplasm, and is not removed. The black arrowhead shows the mitochondrial autophagy, and the white arrowhead shows the lipid droplet.

There are a lot of defective mitochondria in MCF-7 transplanted tumor cells of the ADRB3 antibody group, which is reflected as mitochondrial *crista* decrease, disappearance and volume expansion (FIG. 80). Mitochondrial autophagosomes of the transplanted tumor cells in the antibody group are accumulated in cytoplasm, thereby accelerating the aging of cells. Blocking the ADRB3 on the mitochondrial outer membrane will destroy the mitochondrial membrane potential, and damage the mitochondrial structure and function, thereby resulting in a lot of defective mitochondria in cytoplasm. If autophagy of cells is normal, the defective mitochondria will be removed by the autophagy. The blocking of ADRB3 destroys the fusion of autophagy and lysosomes, so that autophagosomes cannot be removed. The black arrowhead shows the mitochondrial autophagosome, and the white arrowhead shows the lipid droplet (FIG. 81).

Example 13 Immunofluorescence Detection of MPO/ADRB3 Expressions in Cells of Hydrothorax Smears of Lung Cancers 1. Test Method Hydrothorax was collected from 20 patients with lung cancer definitely diagnosed, about 5 ml of liquid at the bottom of the container was transferred to centrifuge tubes, and centrifuged at 2000 rpm for 10 min. After the supernatant was discarded, the remaining 0.5 ml of liquid and precipitate was retained, and fully mixed with a thin glass rod. The fully mixed liquid was transferred onto slides with a pipette (1-2 drops/slide) to prepare uniform smears by pushing the slides, which were immobilized in 95% alcohol for 15 min, taken out, and dried for later use. After transparentizing with 0.1% TritonX-100 for 10 min and closing with BSA for 1 h, MPO/ADRB3 antibody (1:100) was added dropwise, and the slides were closed in a wet box and kept at 4° C. overnight. After FITC and PE-labeled secondary antibody was added dropwise, the slides were kept at room temperature for 1 h, stained with 0.5 ug/ml DAPI for 3 min, sealed with 50% glycerol/PBS, observed under a laser scanning confocal microscope randomly for 5-7 fields, and photographed. The mean red fluorescence intensity and the mean green fluorescence intensity of cells were measured with software Fluorchem 8900.

Figure 82:
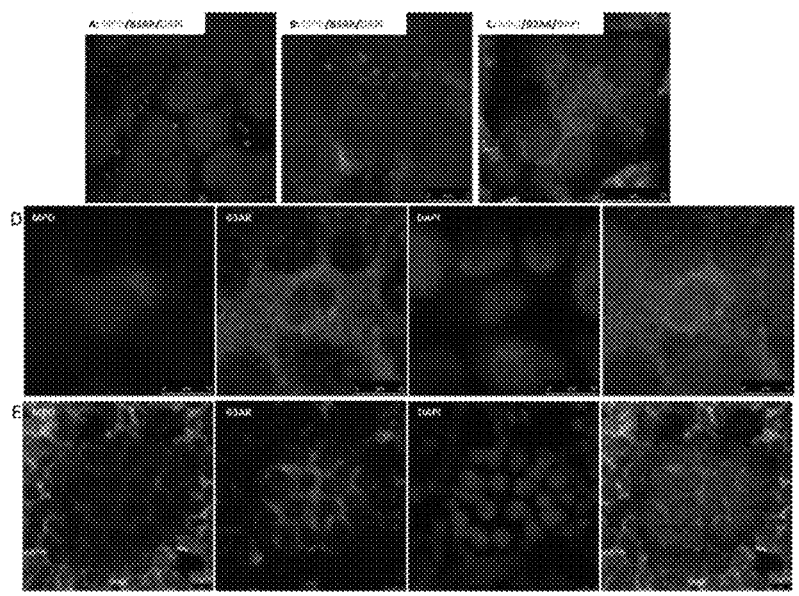
FIG. 82: immunofluorescence of hydrothorax cell smears stained with MPO and ADRB3 of lung cancer patients; A.

2. Test Results (as Shown in FIG. 82):

(1) There are a lot of soluble ADRB3 (soluble B3, sB3) in the hydrothorax of lung cancer patients, suggesting that cancer cells and granulocytes release sB3 into blood and tissue spaces by degranulation.

(2) There are lots of ADRB3 in granulocyte cytoplasm of the hydrothorax. Granulocytes rich in ADRB3 tend to be adhered to lung cancer cells and stimulate the proliferation of cancer cells by direct contact.

(3) The ADRB3 is highly expressed in exfoliated lung cancer cells in the hydrothorax.

Example 14 Immunofluorescence Detection of ADRB3 Expression in Cells in Peripheral Blood Smears of Normal Subjects and Breast Cancer Patients 1. The test method is the same as that in Example 1.

2. Test Results (1) The ADRB3 is expressed in neutrophils and lymphocyte progenitor cells of normal subjects (FIG. 83A), is less expressed in mature CD4+ and CD8+T cells, and is highly expressed in naive or primitive T-lymphocytes (cytoplasm containing lots of CD4 lymphocytes) (FIG. 83B). The ADRB3 is highly expressed in cells of early mitosis (FIG. 83C). The expression level of ADRB3 in lymphocytes is less than that in granulocytes. In the peripheral blood of breast cancer patients, there a lot of abnormal lymphocytes, cytoblast has granulocyte-like changes, which are reflected as reniform, lobulated and irregular shapes. The ADRB3 is highly expressed in lymphocytes, the karyotypes of which have granulocyte-like changes (FIG. 84A). There are a lot of foot processes in the granulocytes of cancer patients, and there are a lot of ADRB3 in the foot processes. There are a few foot processes on the surface of granulocytes of normal subjects, and the ADRB3 content is significantly less than that of granulocytes in cancer patients (FIG. 84B).

(2) The ADRB3 and Ki-67 are highly expressed in neutrophils and lymphocytes of breast cancer patients. Tumor cells and granulocytes induce lymphocytes to express ADRB3 and inhibit the activation of lymphocytes. The expression level of ADRB3 in some lymphocytes is more than that in granulocytes. Lymphocytes highly expressing ADRB3 and Ki-67 can express a small amount of marker proteins-MPO of myeloid cells (FIG. 85), suggesting that such cells are differentiated to myeloid cells, indicating that lymphocytes in breast cancer patients become dedifferentiated and become naive or primitive lymphocytes. The ADRB3 inhibits the differentiation of T cells.

(3) There are a large number of neutrophils extracellular networks (NET) in the blood of breast cancer patients, and the lymphocytes are adhered to the NETs, and ADRB3 is the main ingredient of NET (FIG. 86), suggesting that lymphocytes will receive signals from granulocytes in the nearby microenvironment (niche), and the ADRB3 in cancer cells and granulocytes form NET, which surrounds lymphocytes and regulates the differentiation and proliferation of lymphocytes. NET creates an inhibitory immune environment, and inhibits the anti-cancer function of lymphocytes.

(4) The granulocytes of breast cancer patients were adhered to the lymphocytes by ADRB3 (FIG. 85). Granulocytes are less adhered to lymphocytes in the peripheral blood of normal subjects. Granulocytes are more firmly and frequently adhered to lymphocytes in cancer patients, which is closely associated with the enhancement of the ADRB3 adhesion factor-like activity on the surface of granulocytes and lymphocytes in cancer patients. The MPO is expressed in lymphocytes adhered to by granulocytes, indicating that the ADRB3 in granulocytes induces to dedifferentiate lymphocytes to lymphocyte progenitor cells or myeloid cells.

(5) The expression level of Ki-67 in lymphocytes of cancer patients is positively correlated with the expression level of ADRB3, and Ki-67 is expressed in ADRB3 positive lymphocytes (FIG. 87). After granulocytes contact with lymphocytes, if the Ki-67 is expressed in lymphocytes, the ADRB3 content in cells will be more than that in granulocytes, suggesting that granulocytes or cancer cells increase the ADRB3 expression in lymphocytes, and the ADRB3 induces to dedifferentiate lymphocytes to primitive cells or progenitor cells with proliferation capacity. The ADRB3 is highly expressed, and Ki-67 and MPO are less expressed in a part of lymphocytes of breast cancer patients, which are naive lymphocytes (FIG. 88).

(6) There are a large number of DNA fragments in the blood of breast cancer patients, and the ADRB3 is adhered to the DNA fragments (FIG. 89), which provide nucleic acid for cancer cell replication. The higher the contents of DNA/ADRB3 complex in the blood are, the stronger the proliferation capacity of cancer cells is, and the easier the distant metastasis will take place.

(7) The ADRB3 is highly expressed in the cytoplasm of primitive plasmocytes, which have the characteristics that the cytoplasm contains a lot of dense rough-surfaced endoplasmic reticulums, there are a lot of ADRB3 in the cytoplasm (FIG. 90), and the cytoblast of primitive plasmocyte is larger than that of T cells. There are a lot of ADRB3 in the cytoplasm of mature plasmocytes (FIG. 91), and mature plasmocytes have the characteristics that there is no CD4 or CD8, but a lot of ADRB3 in the cytoplasm. The ADRB3 is expressed on the CD19$^+$B cell membrane (FIG. 92). The ADRB3 can promote plasmocytes to synthesize antibodies.

Example 15 ADRB3 Antibody Promotes Apoptosis of Pancreatic Cancer Cell PANC-1

1. Test Method

The PANC-1 was cultured, and treated with 50 ng/ml ADRB3 antibody for 12 h, while the control group was treated with mouse IgG. The apoptosis rate was detected with flow cytometry by Annexin V/PI double staining.

2. Test results: Compared with the control group, the ADRB3 antibody increases the apoptosis rate of PANC-1 (45.3±7.3% vs 9.7±3.4%, P<0.01). Breast cancer MDA231 and lung cancer H1299 have similar results, all of which show that ADRB3 antibodies promote cell apoptosis.

Example 16 ADRB3 Plasmid Carrying Green Fluorescent Protein (GFP) Kill Pancreatic Cancer Cell SW1990

1. Test Method

The carrier plasmid pENTER-ADRB3-GFP and plasmid pcDNA3/FLAG-ADRB3 are transfected into pancreatic cancer cells SW1990 and MCF7, and were observed under a confocal microscope 24 h later.

2. Test Results:

All cells with GFP expression will have apoptosis, which is reflected as karyopyknosis and cytoclasis, but there is no GFP in the cytoblast (FIG. 93), suggesting that an exogenous ADRB3 carrying GFP cannot enter the cytoblast, is accumulated on the nuclear membrane, and affects the exchange of substances inside and outside the cytoblast, thereby resulting in cell apoptosis. ADRB3 carrying Flag tag proteins cannot enter the cytoblast, either, but does not affect the cell activity. ADRB3 is localized on the microtubule, cytoblast and mitochondria of MCF7 cells (FIG. 94).

Example 17 Chromatin Immunoprecipitation-Chip Test (ChIP-Chip)

1. Test Method

The test group was treated with 50 ng/ml ADRB3 antibody for 24 h, while the control group was treated with mouse IgG. 270 ul 37% formaldehyde was added into a 10 cm culture dish (MCF7), gently fully mixed, and kept at room temperature for 10 min. 1 ml of 1.25M glycine was added, and kept at room temperature for 5 min to neutralize formaldehyde. The mixed solution in the dish was sucked out. The cells were washed with precooled PBS/EDTA twice, and then added 1 ml of PBS containing protease inhibitor cocktail was added. Cells at the bottom of the dish were scraped down by a cell scraper, collected into a 1.5 ml centrifuge tube, and centrifuged at 2000×g for 5 min. The supernatant was discarded. The collected samples were sent to the company for testing. The antibodies used in the immunoprecipitation were ADRB3 antibody and H3K9AC antibody. In different active states of ADRB3, the binding site of ADRB3 in the whole genome and the acetylation level of H3K9 in the promoter were analyzed.

2. Test Results (as Shown in FIG. 95)

A promoter sequence (a promoter of more than 3000 genes) specifically binding to the transcription factor ADRB3 was obtained by ChIP-chip screening from ADRB3 antibody, including but not limited to the following genes: FABP5 (fatty acid-binding protein, epidermal. 82191426 to 82191897 bases with ADRB3 bound to No. 8 chromosome), FABP4, FABP3, PTPRA (receptor-type tyrosine-protein phosphatase alpha), PTPRCAP (protein tyrosine phosphatase receptor type C-associated protein), PTPN7, PTPRZ1 (receptor-type tyrosine-protein phosphatase zeta isoform), PTPRD (receptor-type tyrosine-protein phosphatase delta isoform), PTPRR, LILRB2, LILRB4, LILRA4, LILRA3, LILRP2, FES (tyrosine-protein kinase Fes/Fps), TUMOR NECROSIS FACTOR-RELATED APOPTOSIS-INDUCING LIGAND RECEPTOR, STAT5B, TCL1 (T-cell leukemia/lymphoma protein 1A), CD8A (T-cell surface glycoprotein CD8 alpha chain), C8G (coding complement C8, 139838398 to 139838876 bases with ADRB3 bound to No. 9 chromosome), C5AR1 (complement C5a receptor, 47812870 to 47813391 bases with ADRB3 bound to No. 19 chromosome), AKT1 (105260668 to 105261174 bases with ADRB3 bound to No. 14 chromosome), LDHAL6B (coding lactic dehydrogenase A-like protein 6B, 59497805 to 59498262 bases with ADRB3 bound to No. 15 chromosome), SLC16A3 (The gene encodes a monocarboxylic acid transport protein and regulates the transmembrane transport of lactic acid. 80185203 to 80186585 bases with ADRB3 bound to No. 17 chromosome), RRP9 (51975065 to 51975538 bases with ADRB3 bound to No. 3 chromosome, the gene codes U3 small nucleolar RNA-interacting protein 2), DKC1 (153989742 to 153990209 bases with ADRB3 bound to X chromosome, the gene is associated with the telomere stability), IZUMO1 (izumo sperm-egg fusion protein 1, 49250722 to 49251290 bases with ADRB3 bound to No. 19 chromosome), TSKS (testis-specific serine kinase substrate, 50266261 to 50266930 bases with ADRB3 bound to No. 19 chromosome), TSSK6 (testis-specific serine/threonine-protein kinase 6), amyloid beta A4 protein isoform d, EDA2R, EDAR, PDE10A, PDE12, PDE1C, PDE4A, PDE4B, PDE4C, PDE6, PDE7, PDE9 multidrug resistance-associated protein 1 (MRP1), PSPN, brain-derived neurotrophic factor, NGDN, insulin-like growth factor II, X-linked inhibitor of apoptosis protein (XIAP), vesicle transport protein SFT2A, poly [ADP-ribose]polymerase 1, GPBP1, MYL3, GJA9-MYCBP, INHBC, SEH1L, TNPO2, NUP50, NUSAP1, GAR1, DKC1, GTPBP4, NOP56, NEXN, ACVR1, TNNT2, KCNQ1, KCNH2, ACTL6A, ATP6V0B, PAX6, DCX, TSKS, regulator of telomere elongation helicase 1, PCSK1, PCSK4, LDLRAD1, SCARF1, S1PR3, SMG6, DKC1, NOP10, BAD, BCL2, CASP12, CFLAR, LAMB3, ITGA2, ITGA7, MMP2, MMP9, RYR3, syntaxin-1B, PACRG, transcription factor Dp-2, transcription factor MafB, transcription factor E2F8, transcription factor E2-alpha isoform E47, hepatocyte nuclear factor 1, mitofusin-1, FGFR2, FGF16, FGF21, HEY1, HEY2, TLE3, TXNIP, RIZ1, IFT140, NPHP3, GATA1, GATAD1, BDNF, PDGF, CDY1, CDY2, APP (Amyloid Beta Precursor Protein), PNMT, COMT, ZMIZ2, DNMT1, SETDB2, SUV39H1, CEACAM1, CEACAM16, KAZN, CEACAM21, CEACAM5, ENO1, FGF1, FGF4, GREM1, TMC6, TMEM43, STK36, IRF1 (interferon regulatory factor 1), WHSC1, IRF3, IRF7, IRF9, cardiotrophin-like cytokine factor 1, tumor protein 63 (189349333 to 189349707 bases with ADRB3 bound to No. 3 chromosome), TPRG1, FKBP5, PRR5 (45063166 to 45063715 bases with ADRB3 bound to No. 22 chromosome), SETD1B, p16, myb-related protein B (42294360 to 42294625 bases with ADRB3 bound to No. 20 chromosome), RPL18A, optineurin, bone morphogenetic protein receptor type-1B, prostacyclin receptor (PTGIR), pentraxin-4, CTBP1, FES, ZAP70, IGSF11, IRF7, KLRC1, TARDBP, MRPL19, MRPL2, MRPL41, MRPS17, MRPS26, RPL14, RPL18A, RPL19, RPS6KL1, atypical chemokine receptor 3, CCL3L1, CCR5, EEF1D, DNMT1, PDE4B, FOXP3 (49121975 to 49122469 bases with ADRB3 bound to X chromosome), DCANP1, DCST1, DCST2, leukemia inhibitory factor, IL17RB, TRAF6, p62, hexokinase-2 (75059882 to 75060125 bases with ADRB3 bound to No. 2 chromosome), TCIRG1, HK1, CAMKK2, GAPDH, G1/S-specific cyclin-D3 (42016706 to 42017624 bases with ADRB3 bound to No. 6 chromosome), Cyclin D1, cyclin-dependent kinase 3 (73995762 to 73996227 bases with CDK3 and ADRB3 bound to No. 17 chromosome), CDK4, CDK15, CDK18, cyclin-dependent kinase 2-associated protein 1, Rb, Ki-67, mTOR, Rictor, AKT, tubulin, Src (proto-oncogene tyrosine-protein kinase Src), PD-L1, p53, interleukin 1 (IL-1), interleukin 6 (IL-6), IL25, IL27, IL17RB, IL16, LEF, ADRB3, TGFB1I1, TAB2, LTBP2, RAS, ARHGAP21, TGF- and TNF.

CHIP-chip results of H3K9AC antibody show that: K9 of the H3 histone in the CDK3 promoter area to which ADRB3 is bound (73995762 to 73996227 bases of No. 17 chromosome) is acetylated, showing that ADRB3 is acetylase transferring the acetyl to H3K9. ADRB3 affects the transcription of target genes by regulating the acetylation level of H3K9 within the target gene promoter. ADRB3 can bind to the promoter of neurotrophic factor, indicating that ADRB3 regulates the expression of neurotrophic factor, suggesting that ADRB3 antibodies can treat Alzheimer disease, Parkinson's disease and other neurodegenerative diseases.

Example 18 Endotoxin-Induced Death Test

1. Test Method

LPS was intraperitoneally injected into mice (10 normal FVB mice and 10 ADRB3 knockout mice) at a dose of 30 mg/kg. LPS was dissolved in water for injection to prepare into 1 mg/ml solution. The injection dosage (ml) was obtained by multiplying the mouse weight (g) by 0.03. The death of mice was observed, and the death time was recorded to draw the survival curve of mice in each group. Inflammatory necrosis and granulocytic infiltration of liver and lung tissues were observed after HE staining. Neutrophils in the abdominal secreta were detected by immunofluorescence of cell smears. Expressions of IL-6, MPO and Elastase in liver and lung tissues were detected by immunohistochemical analysis.

2. Test Results

After injection of endotoxin, the vitality of mice was significantly reduced, their body temperature was decreased, the eyes of some mice were festered, and they showed pyohemia. Within 16 hours after injection of LPS, 10 FVB mice all died, 2 ADRB3$^{-/-}$ mice died, but 8 ADRB3$^{-/-}$ mice survived. Compared with normal mice, the mortality of ADRB3$^{-/-}$ mice caused by pyohemia was significantly reduced (FIG. 96), and the area of inflammatory necrosis of liver and lung tissues was significantly reduced. There were a lot of festers in the abdomen of both groups, and the mice had peritonitis accompanied with phohemia. The count of neutrophils recruited to the peritoneal lesion was significantly reduced in ADRB3 knockout mice with peritonitis. The expressions of IL-6 and Elastase protein in liver and lung tissues of ADRB3$^{-/-}$ mouse were significantly reduced, indicating that inflammatory response and neutrophilic infiltration of liver and lung tissues were inhibited.

Example 19 ADRB3 Antibody Inhibits Adenovirus and Hepatitis B Virus (HBV) from Infecting Cells 1. Test Method Coverglass for growth of A549 were pretreated with the ADRB3 antibody for 30 min, inoculated with $10^6$ PFU/ml adenovirus carrying GFP, and incubated in an incubator at 37° C. for 24 hours. The control group was treated with mouse IgG. The expression of phosphorylated mTOR (S2448) was detected by immunofluorescence. The method is the same as that in Example 1.

Liver tissue samples of patients with chronic hepatitis B were collected to detect the expression of ADRB3 by immunohistochemical analysis following the method of Example 2.

Coverglass for growth of HepG2 were pretreated with the ADRB3 antibody for 30 min, inoculated with 1 ml of HBV, and incubated in an incubator at 37° C. for 24 hours. The control group was treated with mouse IgG. The coverglass was immobilized with 4% paraformaldehyde, and HBcAg was detected with rabbit anti-HBC (1:100). The coverglass was kept at 4° C. overnight, and sheep anti-rabbit IgG was added on the next day. The coverglass was kept at 37° C. for 1 hour, and washed. PAP (1:50) was added. The coverglass was incubated at 37° C. for 1 h, washed 3 times, and then developed with DAB for microscopic examination.

2. Test Results (1) When ADRB3 was suppressed, adenovirus was unable to infect lung cancer cells A549. The ADRB3 antibody plays a role in inhibiting adenovirus infection by inhibiting phosphorylation of 2448th serine of mTOR (FIG. 97). Phosphorylation of 2448th serine will activate mTOR and promote autophagy, and autophagy promotes the replication and release of adenovirus. The ADRB3 antibody plays a role in inhibiting autophagy by inhibiting activation of mTOR, thereby inhibiting the replication and release of adenovirus. After blocking ADRB3, the ADRB3 antibody can increase the expression of C8, which can dissolve the virus and prevent viral infection.

(2) Both the ADRB3 and adenovirus are localized in nucleoli of lung cancer cell A549, and the ADRB3 may be a key protein required for viral replication (FIG. 98). Adenovirus can cause cell carcinogenesis by activating ADRB3 in the nucleolus.

(3) The ADRB3 in cytoplasm of liver of a hepatitis B patient is higher than that of normal subjects, and almost no ADRB3 is expressed in the cytoblast. The ADRB3 in the cytoplasm enhances ribosomal functions, and contributes to synthesis of the proteins required for HBV replication. The ratio of cytoplasmic ADRB3 to nuclear ADRB3 is increased significantly, and the higher the ratio is, the more active the viral replication is. This ratio can be used as an index for detecting hepatitis B virus replication. The ADRB3 in cytoplasm mediates HBV to enter HepG2 and promotes HBV replication. The ADRB3 antibody inhibits the HBV from infecting HepG2 (FIG. 99), indicating that the antibody has the potential for treating hepatitis B.

Example 20 Research on the Effect of High Cholesterol (HCD) and Low Cholesterol Feeding (LCD) on Atherosclerotic Plaque in ADRB3 Deficient ApoE$^{-/-}$ Mice (B3$^{-/-}$ApoE$^{-/-}$)

1. Test Method

The effect of high cholesterol (HCD) and low cholesterol feeding (LCD) on atherosclerotic plaque in ADRB3 deficient ApoE$^{-/-}$ mice (B3$^{-/-}$ApoE$^{-/-}$) was researched, and the B3$^{+/+}$ApoE$^{-/-}$ mice feeding on HCK were selected as the control group. The laboratory mice were divided into four groups: 1. High cholesterol (HCD) feeding group of B3$^{-/-}$ ApoE$^{-/-}$ mice; 2. HCD group of B3$^{-/-}$ ApoE$^{-/-}$ mice; 3. low cholesterol feeding (LCD) group of B3$^{-/-}$ ApoE$^{-/-}$ mice; and 4. HCD feeding and ADRB3 antibody combined treatment group of B3$^{+/+}$ApoE$^{-/-}$ mice. 10 male mice of 8 weeks old were selected for each group, and were fed with high fat (20% triglyceride, 1.25% cholesterol) and common feed. The ADRB3 antibody was fed at a dose of 10 mg/kg. The mice were intraperitoneally injected once every 6 days. The aorta was taken after feeding with high fat for 12 weeks, and stained with oil red O. The number and size of arterial plaques in 4 groups were compared. Inflammatory cells in plaques were detected after HE staining. The expression of inflammatory factor in plaques was detected by immunohistochemical analysis. Inflammatory cytokines IL-6, VEGF, IL-10 and MPO in serum were detected by ELISA.

2. Test Results (as Shown in FIG. 100)

After feeding with high fat feed for 3 months, ApoE$^{-/-}$ mice were extremely aged with hunchback, hair slip, subcutaneous fat, movement function loss, etc., but B3$^{-/-}$ ApoE$^{-/-}$ mice had unconspicuous aging characteristics. The number and area of aortic plaques in B3$^{-/-}$ ApoE$^{-/-}$ mice of HCD group and B3$^{+/+}$ ApoE$^{-/-}$ mice of ADRB3 antibody treatment group were significantly less than those in B3$^{+/+}$ ApoE$^{-/-}$ mice, and the area of aortic plaques was reduced by 80%-90%. ADRB3 deficient ApoE$^{-/-}$ mice had hard plaques, which were stable plaques. In B3$^{-/-}$ ApoE$^{-/-}$ mice, the blood fat concentration of HCD group was significantly higher than that of LCD group, but there is no difference between the number and area of aortic plaques of both groups. Compared with B3$^{+/+}$ ApoE$^{-/-}$ mice of HCD group, B3$^{-/-}$ ApoE$^{-/-}$ mice of HCD group and B3$^{+/+}$ ApoE$^{-/-}$ mice of ADRB3 antibody treatment group had thickened fibrous caps of aortic plaques, reduced CD4$^+$T cell and granulocyte infiltration, MPO in foam cells of plaques, neutrophil Elastase, IL-6, ADRB3 and reduced MIF. The concentration of IL-10 in serum of B3$^{-/-}$ ApoE$^{-/-}$ mice is increased, but the concentrations of IL-6, VEGF and MPO are reduced.

Conclusions: (1) ADRB3 promotes the formation of atherosclerotic plaques, results in plaque instability, and is one of the factors causing acute coronary syndrome; and (2) ADRB3 promotes aging.

Example 21 ADRB3 Monoclonal Antibody Reduces Blood Pressure of Spontaneously Hypertensive Rats 1. Test Method Male spontaneously hypertensive rats (SHR) of 14 weeks old with the systolic pressure higher than 140 mmHg were randomly divided into 2 groups with 8 rats in each group, and were intraperitoneally injected once every 6 days for 6 consecutive weeks. The groups were as follows: (1) antibody group: 10 mg/kg ADRB3 antibody; (2) control group: intraperitoneally injected with mouse IgG. The systolic pressure and heart rate were indirectly examined at caudal artery of rats in a waking state using a RBP-1B rat blood pressure gauge by tail cuff method. The systolic pressure, heart rate and body weight were examined at caudal artery before and after injection every week to calculate the pressure reduction extent=(systolic pressure before treatment−systolic pressure after treatment)/systolic pressure before treatment. Rats were put to death 6 weeks after injection, and their chests were cut open. Their hearts were immediately cut out and put in KH solution at 4° C., residual blood in their cardiac chambers was squeezed out, their ascending aortas were separated, and their aortas were hung, after retrograde intubation, on a Langendorff perfusion device for retrograde perfusion with KH solution fully oxygenated with 95% O$_2$ and 5% CO$_2$ at a constant temperature of 37° C. The catheter balloon was inserted into the left ventricle through the left atrium catheter, the catheter was connected to a pressotransducer, water was injected into the balloon to enhance the internal pressure therein to 40 mmHG and keep under the internal pressure. After the indexes were stable by prefilling for 20 min, Pclab biological signals were used to acquire and record the cardiac function indexes of the system: left ventricular pressure (LVP), left ventricular systolic pressure (LVSP), left ventricular end-diastolic pressure (LVEDP) and left ventricular developed pressure (LVDP), maximum rate of left ventricular systolic pressure rise (+dp/dtmax), maximum rate of left ventricular diastolic pressure descendent (dp/dtmax) and heart rate (HR). The coronary flow (CF) was collected and recorded. After stopping filling, the heart was taken out and dried with filter paper. The aorta was cut out and weighed to calculate the heart weight/body weight (HW/BW); the free wall and atrium of the right ventricle were cut out, the left ventricle (including the ventricular septum) was weighed, and the left ventricular hypertrophy degree was expressed as the ratio of the left ventricle weight to the body weight (LVW/BW).

SPSS19 was used for statistical analysis, and the measurement data were expressed as mean±standard deviation, and t-test was used in the mean comparison between two groups.

2. Test Results

The blood pressure of the ADRB3 antibody treatment group was reduced to normal blood pressure (Table 4), and was decreased significantly compared with that before treatment and that of the control group (P<0.01). The pressure reduction difference and extent of the ADRB3 antibody group were significantly increased, compared with those of the control group, and the difference was statistically significant (P<0.01). The effect of ADRB3 antibody on cardiac functions is shown in Table 5. LVEDP of the antibody treatment group was significantly lower than that of the control group (P<0.05), and the HR was significantly reduced, compared with that of the control group (P<0.05), indicating the improvement of cardiac functions. The changes of heart weight/body weight and left ventricle weight/body weight of each group were shown in Table 6. HW/BW and LVW/BW of the antibody group were significantly lower than those of the control group, and the difference was statistically significant (P<0.05). The ADRB3 antibody effectively reduces SHR blood pressure to normal range, improves cardiac functions of SHR, and blocks left ventricular hypertrophy caused by hypertension.

TABLE 4

Changes of Systolic Pressure of Spontaneously Hypertensive Rats Before and After Treatment (mmHg) ($\bar{x} \pm s$, n = 8)

| Group | Before treatment | After treatment | Pressure reduction difference | Pressure reduction extent (%) |
|---|---|---|---|---|
| Control group | 174.5 ± 12.2 | 180.5 ± 8.0 | −5.5 ± 4.5 | −3.6 ± 3.2 |
| Antibody group | 177.6 ± 4.4 | 98.5 ± 14.4*# | 80.1 ± 12.5# | 45.4 ± 8.6# |

Note:
compared with that before treatment,
*P < 0.01; compared with the control group,
P < 0.01.

TABLE 5

Cardiac Functions of Spontaneously Hypertensive Rats ($\bar{x} \pm s$, n = 8)

| Group | LVSP | LVEDP | LVDP | +dp/dtmax | −dp/dtmax | HR | CF |
|---|---|---|---|---|---|---|---|
| Control group | 105 ± 10 | 36 ± 4 | 87 ± 16 | 2765 ± 607 | 1456 ± 356 | 202 ± 18 | 4.4 ± 2.1 |
| Antibody group | 90 ± 32 | 22 ± 3* | 80 ± 22 | 1729 ± 759 | 732 ± 280 | 152 ± 26 | 2.4 ± 0.9 |

Note:
compared with the control group, *P < 0.05;
LVP, LVSP, LVEDP and LVDP: mmHg; CF: ml/min.

TABLE 6

Heat Weight/Body Weight, Left Ventricle Weight/Body Weight of Spontaneously Hypertensive Rats ($\bar{x} \pm s$, n = 8)

| Group | HW/BW (mg/g) | LVW/BW (mg/g) |
|---|---|---|
| Control group | 5.6 ± 0.2 | 2.5 ± 0.3 |
| Antibody group | 4.1 ± 0.3* | 1.5 ± 0.2* |

Note:
compared with the control group,
*P < 0.05.

Example 22 ADRB3 Antibody Induces Peripheral Blood Mononuclear Cell (PBMC) to Differentiate Toward Cytotoxic T Cells 1. Test Method 3-5 ml of peripheral blood samples were taken from each of 5 normal subjects, 5 pancreatic cancer patients, 5 liver cancer patients, 5 lung cancer patients and 5 leukemia patients. PBMC was separated with Ficoll by density gradient centrifugation, cultured in 5% fetal bovine serum DMEM, and inductively cultured with different concentrations of ADRB3 antibody. ADRB3 antibodies were not used in the control group. Cells were collected respectively on 0th, 2nd, 4th, 6th, 8th and 10th days of inductive culture to quantitatively analyze $CD4^+$, $CD8^+$T cells and Treg cells by flow cytometry. Induced cells were lysed and centrifuged, and the supernatant was taken to validate the killing effect of induced differentiation on target cells by MTT assay. SW1990, MCF-7 and other adherent tumor cells were selected as target cells, and were inoculated into 96-well culture plate. In the experimental group, the supernatant was lysed with different concentrations of cells, and the control group was cultured in a culture medium containing equivalent volume of solvent at 37° C. under 5% $CO_2$ for 5 d. 200 μl of a fresh serum free medium containing 0.5 mg/ml MTT was added to each well, and further continued for another 4 h. After the liquid in each well was fully sucked out, 200 ul of DMSO was added, and shaken for 10 min to measure the optical density value with an ELIASA at a wavelength of 570 nm and a reference wavelength of 450 nm.

2. Test Results:

In the 0.5-100 ug/ml dose range, the ADRB3 antibody promotes PBMC to differentiate into $CD8^+$T cells, and decrease the proportion of Treg cells. When the given concentration of antibody was applied for 6 to 8 days, the anticancer cytokines in induced cells had higher effects. The highest dose of cell lysate could kill about 80% target cells. The ADRB3 antibody induces immune incompetent lymphocytes to become functional cells and play an anti-cancer role.

Example 23 ADRB3 Antibody Promotes Complement Activation

Cells MCF-7, A549 and SW1990 were treated with different concentrations of ADRB3 antibody. Endotoxin (LPS) was used as a positive control. 2 days later, cell protein was collected, and complements C3, C8 and C5 (C5R) were detected by western blot. C8 and B3AR were detected by immunofluorescence.

The test results show that the ADRB3 antibody dose-dependently increases expressions of C3, C8 and C5R (FIG. 101). After ADRB3 antibody treatment, a large number of C8 arise on the cell membrane, but B3AR disappears, and there are karyopyknosis and apoptosis (FIG. 101B). C8 is a membrane attack complex (MAC), and forms an indispensable important material. The ADRB3 antibody promotes MAC assembly and insertion into the cell membrane, thereby resulting in cell rupture and death.

Example 24 Effect of ADRB3 Antibody on Cardiovascular System

The research results show that the ADRB3 antibody has different degrees of antagonism to experimental myocardial infarction or arrhythmia, and other animal models, improves the imbalance between supply and demand of oxygen in ischemic myocardium. ADRB3 antibody alleviates the myocardial ischemia degree in the model of anterior descending ligation of myocardial infarction and narrows the infarct range after coronary artery occlusion. The rats are intraperitoneally injected with ADRB3 antibody to antagonize arrhythmia caused by aconitine. ADRB3 antibody reduces aging myocardial cells and improves cardiac functions.

Example 25 Effect of ADRB3 Antibody on Blood System

The research results show that ADRB3 is located on the platelet membrane (FIG. 102). The ADRB3 antibody can improve microcirculation, inhibit platelet aggregation, and have a significant inhibitory effect on in-vitro thrombosis in rats.

Example 26 Effect of ADRB3 Antibody on Respiratory System

The research results show that the ADRB3 antibody reduces the flow rate in lungs of perfused guinea pigs, has the bronchocnstricting effect, and has antispasmodic effect on isolated intestinal spasm caused by acetylcholine.

Example 27 Antifatigue Effect of ADRB3 Antibody

Rats were loaded with 5% body weight of lead sheath at the root of the tail, and were placed in a swimming pool with the water depth of 30±1 cm and at a water temperature of 25±1° C., where four legs of each rat were kept moving. The time since the mice began to swim to death time (min) was recorded as the swimming time of the mice. The results show that the mice injected with the ADRB3 antibody have longer swimming time in ice water than the control group, and the ADRB3 antibody has anti-fatigue effect.

Example 28 ADRB3 Antibody Improves Sleep Function

The results show that the ADRB3 antibody could shorten the sleep latency of mice, increase the number of sleeping mice, and significantly prolong the sleep duration of mice administered with threshold dose of pentobarbital sodium.

Example 29 Therapeutic Effect of ADRB3 Antibody on Mouse Model of Alzheimer Disease (AD)

The research results show that the ADRB3 antibody could improve the learning and memory of AD mice, increase the expression of brain-derived neurotrophic factor (BDNF) gene, and reduce the senile plaque formation caused by intracerebral Aβ deposition.

Example 30 ADRB3 Antibody has the Effect of Regulating Blood Lipids

The research results show that injection of the ADRB3 antibody could reduce the blood triglyceride, total cholesterol and LDL level of rabbits with experimental hypercholesterolemia, enhance HDL, stabilize plaques, and reduce aortic and coronary atherosclerotic plaque formation.

Example 31 ADRB3 Antibody Inhibits Adenovirus and Hepatitis B Virus (HBV) from Infecting Cells The research results show that the ADRB3 antibody can reduce the liver fibrosis degree of C57BL mice model of liver cirrhosis by intraperitoneal injection of CCL4, inhibit inflammatory cell infiltration around liver tissue portal area and bile duct, reduce ascites caused by liver cirrhosis, and improve liver functions.

Example 32 ADRB3 Antibody Inhibits Replication of Hepatitis B Virus (HBV)

The ADRB3 antibody is transfected into HBV transgenic mice by caudal vein injection, and blood samples were taken from their angular veins respectively on 6th day and 21st day, in 1st month, 3rd month and 9th month after injection to quantitatively detect the HBsAg level in serum of mice by chemiluminescence and detect the HBV-DNA level by PCR. The results show that the ADRB3 antibody could significantly reduce the HBsAg and HBV-DNA level in serum of transgenic mice.

Example 33 ADRB3 Antibody Improves Fertility and Sexual Function

The ADRB3 antibody can enhance the sexual behavior ability of mice. The results of mating experiments show that the immune cell lysate can significantly increase the number of sexual impulses of impotence model mice, increase the mating rate, prolong the mating time, and increase the impregnation rate of female mice, the frequency of giving births and the survival rate of baby mice.

Example 34 Effect of ADRB3 Antibody on Autoimmunity and Survival Time of Lupus Mice The research results show that the ADRB3 antibody could prolong the survival time of BXSB lupus mice, reduce the expression levels of anti-ds-DNA antibody and IgG in the peripheral blood, and inhibit the expression of IFN-γ in spleen and kidney.

Example 35 Research on Treatment of Aged Mice

Healthy C57BL/6 mice, regardless of male and female, were selected and divided into 2 groups: 10 mice in the ADRB3 antibody treatment group and 10 mice in the normal saline control group. Treatment was started when the mice were 12 months old. The ADRB3 antibody treatment group was intraperitoneally injected with 0.1 mg of ADRB3 antibody once every week for a total of 3 months; the normal saline control group was injected with normal saline. Behavioral tests were performed when the mice were 12, 15, 18 and 21 months old, including passive avoidance experiment, Morris water maze experiment, open field maze experiment and elevated plus maze experiment.

Behavioral results show that in the Morris water maze experiment, as shown by the positioning navigation experiment, mice in the normal saline control group show a longer escape latency; as shown by the space exploration experiment, the distance percentage in the platform quadrant of mice in the normal saline control group is decreased and the time percentage was decreased, which are significantly different from the ADRB3 antibody treatment group.

The anxiety index was detected from the perspective of behavioristics: as shown by the open field maze experiment results, the distance percentage of mice in the normal saline control group in the central area is significantly decreased, which is significantly different from the ADRB3 antibody treatment group.

As shown by the elevated plus maze experiment results, the distance percentage in the arm opening area and the frequency percentage of arm opening of mice in the normal saline control group are significantly decreased, which are significantly different from the ADRB3 antibody treatment group.

The passive avoidance experiment results show that compared with the ADRB3 antibody treatment group, the normal saline control group has more errors and shorter latent period.

The HE staining results show that the ADRB3 antibody treatment group is close to healthy mice of 12 months old, has a large number of brain cells arranged in order, and has complete neuron cells. However, mice in the normal saline control group have obvious neuron vacuole-like degenerations, and the cells are loosely arranged.

Example 36 Research on Glioma Treatment

Human glioma cells U87 were subcutaneously transplanted into the back of nude mice of 6 weeks old, which were used as the tumor model after tumor formation. In the experiment, the mice were divided into 4 groups with 8 mice in each group: normal control group, model control group, ADRB3 antibody treatment group, Gemcitabine and CD40 antibody combined treatment group. The ADRB3 antibody treatment group was intraperitoneally injected with 0.1 mg of ADRB3 antibody once every 5 days for a total of 6 weeks. The model control group was intraperitoneally injected with equivalent amount of normal saline.

The results show that compared with the control group and Gemcitabine treatment group, no metastatic lesion is seen in the lung of the ADRB3 antibody treatment group, metastatic lesions are seen in the control group, and some metastases are found in the Gemcitabine treatment group; and the survival period of the ADRB3 antibody treatment group is significantly longer than that of other groups.

Example 37 Research on Treatment of In-Situ Bladder Cancer in Rats

The in-situ bladder cancer model was constructed by inducing N-methylnitrosourea (MNU). In the experiment, the mice were divided into 4 groups with 8 mice in each group: normal control group, model control group, ADRB3 antibody treatment group, Gemcitabine and CD40 antibody combined treatment group. The ADRB3 antibody treatment group was intraperitoneally injected with 0.5 mg of ADRB3 antibody once every 5 days for a total of 7 weeks. The model control group was intraperitoneally injected with equivalent amount of normal saline.

The results show that the tumor size of the ADRB3 antibody treatment group is reduced by 70% on average, and the tumor no longer continue to grow after 30 days of continuous treatment.

Example 38 Research on Treatment of Leukemia in Mice

The leukemia mouse model was constructed by transplanting human B-lymphocytic leukemia cells NALM-6 into highly immunodeficient NCG mice via caudal vein. In the experiment, the mice were divided into 4 groups with 8 mice in each group: normal control group, model control group, ADRB3 antibody treatment group, Gemcitabine and CD40 antibody combined treatment group. The ADRB3 antibody treatment group was intraperitoneally injected with 0.1 mg of ADRB3 antibody once every 5 days for a total of 5 weeks. The model control group was intraperitoneally injected with equivalent amount of normal saline.

The results show that compared with other groups, the body weight, survival state and survival period of the ADRB3 antibody treatment group are better than those of other groups; the count of NALM-6 cells is decreased significantly, and the surface markers of T cells detected by flow cytometry suggest that the immune function of T effector cells in the treatment group is significantly better than that of the control groups.

Example 39 Research on Treatment of Diabetes in Mice

After diabetic mice (db/db mouse) of 8 weeks old were fasted without water fasting for 12 hours, blood samples were taken from the inner canthus to measure the fasting blood glucose (FGB). The mice with the FGB of above 11.1 mmol/L were randomly divided into 2 groups: 8 mice in the model control group and 8 mice in the ADRB3 antibody treatment group. The ADRB3 antibody treatment group was intraperitoneally injected with 0.1 mg of ADRB3 antibody once 5 five days for a total of 5 weeks. The model control group was intraperitoneally injected with equivalent amount of normal saline. After the last administration, blood samples were taken from the orbit to measure the blood glucose and blood lipid indexes.

The results show that: (1) the ADRB3 antibody group reduces blood glucose in db/db mice (P<0.01). (2) The ADRB3 antibody reduces the total cholesterol and LDL-C content and enhances the HDL-C content in db/db mice, which contributes to recovery of the blood lipid level in diabetic mice (P<0.01).

Example 40 Research on Treatment of Schizophrenia in Mice

The schizophrenia mouse model was established by intraperitoneally injecting C57BL/6 male mice of 8 weeks old with 0.5 mg/kg dizocilpine maleate (MK801). Symptoms similar to schizophrenia were observed: after hyperlocomotion and stereotypy, the mice were divided into the model control group (without injection of MK801), model group (injection of MK801) and ADRB3 antibody treatment group (injection of MK801+ADRB3 antibodies). The ADRB3 antibody treatment group was intraperitoneally injected with 0.1 mg of ADRB3 antibody once 5 five days for a total of 5 weeks. The model control group and the model group were intraperitoneally injected with equivalent amount of normal saline. The open field test and prepulse inhibition (PPI) test were conducted to evaluate and compare the spontaneous activity and sensorimotor gating function of mice in each group.

The results show that: compared with the control group, mice in the model group show significantly increased activity [total movement distance (1622±146.7) cm vs (5502±432.4) cm; spontaneous movement times (122±16.5) vs (332.6±24.3) times; P<0.001] and PPI damaged [78 dB: (35.5±1.6) vs (11.4±2.1), 84 dB: (46.2±5.6) vs (17.4±3.6); P<0.01). Compared with the model group, the ADRB3 antibody treatment group has significantly decreased activity [(2655±331.4) cm, (192.3±17.3), and significantly improved PPI abnormality.

Example 41 Position and Functions of ADRB3 in NK Cells

By double staining umbilical cord blood and adult blood smears with ADRB3 and CD56, it is found that there is a lot of ADRB3 in NK cells of umbilical cord blood, and a little ADRB3 in lymphocytes of cord blood (FIG. 103). There is also ADRB3 in adult NK cells. ADRB3 increase in adult lymphocytes is associated with aging. The ADRB3 in NK cells is positively correlated with contents of CD56, and the more ADRB3, the more CD56. $CD56^{bright}$ is naive NK, while ADRB3 increases CD56, and inhibits NK differentiation and maturation. NK92 cells are made into cell smears to detect ADRB3 and MPO. It is found that ADRB3 and MPO are highly expressed in NK92 cells (FIG. 104). The ADRB3 antibody (5-50 ng/ml) was used to treat NK92 cells. 2 days later, the cells were lysed to detect MPO/CD56 protein contents by western blot. It is found that the ADRB3 antibody dose-dependently reduces MPO and CD56 proteins. ADRB3 has the effects of inhibiting NK cells and preventing NK cells from attacking autologous normal cells.

Example 42 ADRB3 Regulates Monocytes and Megakaryocytes

Immunofluorescence was used to detect the distributions and contents of ADRB3 in monocytes and megakaryocytes in the peripheral blood of normal subjects and patients with acute myocardial infarction. It is found that ADRB3 is highly expressed in monocytes (FIG. 105) and megakaryocytes of the patients with acute myocardial infarction, is significantly more than that of normal subjects, and there is ADRB3 in the mononuclear cytoblast in proliferation phase.

In patients with acute coronary syndrome, the ADRB3 content in megakaryocytes of patients with positive cardiac troponin T (cTnT) is higher than that in megakaryocytes of patients with negative cTnT (FIG. 106).

In animal experiments, Balb/c mice were intraperitoneally injected with the ADRB3 antibody (1 mg/kg body weight) once every 3 days. 2 weeks later, the coagulation function was detected in mice. It is found that the ADRB3 antibody reduces the platelet count, inhibits platelet aggregation, and has a significant inhibitory effect on in-vitro thrombosis in rats. It is found that the ADRB3 antibody reduces the platelet count, inhibits platelet aggregation, and has a significant inhibitory effect on in-vitro thrombosis in rats.

Example 43 ADRB3 Fusion Gene Detection

The ADRB3 fusion genes in the pancreatic cancer cell Panc-1, cancer tissues of pancreatic cancer patients and paracancerous normal tissues were detected by exon sequencing method. It is found that the ADRB3 gene forms fusion genes with a large number of cancer-associated genes, such as MYC, RAS, SRC, MPO, PML, Her2, EGFR, B7, CD8 and CD28. When Panc-1 is treated with ADRB3 antibody, ADRB3 fusion genes are significantly reduced.

Example 44 ADRB3 Antibody Treats Heroin Addiction

SD adult male rats were randomly divided into 2 groups: heroin addiction group and treatment group. The rat model of heroin addiction was established by subcutaneously injecting the rats with heroin 3 times every day at an increasing dose from 10 mg/kg on 1st day to 100 mg/kg on 10th day. Rats in the treatment group were intraperitoneally injected with the ADRB3 antibody (5 mg/kg) after injection of heroin every day. On the next day after the last injection of heroin, rats were intraperitoneally injected with naloxone hydrochloride (4 mg/kg) for 2 h, and then had withdrawal symptoms, such as body torsion, wet dog-like tremble, gritting their teeth, jumping and standing. Thus the animal model of addiction was successfully established. After scoring the withdrawal symptoms, animals in each group were anesthetized to take the whole brain for determination of ADRB3 protein expression in related brain regions of rats by immunohistochemical analysis.

The results show that the withdrawal score of rats in the heroin addiction group is 21.7+4.4, that in the ADRB3 antibody treatment group is 11.7+2.8, and there is significant difference between the two groups (P<0.05). The number of ADRB3-positive neurons expressed in rats of the heroin addiction group is significantly reduced than that in rats of the treatment group (P<0.05). Conclusions: ADRB3 antibody reduces heroin addiction in rats, and the mechanism thereof is related to regulation of the neuronal ADRB3 signal transduction.

SUMMARY

In conclusion, the ADRB3 is a key receptor in nerve-endocrine-immunoregulatory network, and an ADRB3-mediated signaling pathway regulates proliferation and differentiation of neutrophils, lymphocytes and tumor cells. Under normal circumstances, the ADRB3 maintains the non-specific immunocompetence and specific immunocompetence of an organism, and eliminates exogenous pathogenic microorganisms and aged organism tissues to play a role in protecting the organism and anti-aging. Under pathological conditions, excessive activation of the signaling pathway will cause systemic chronic inflammation, and destroy immune homeostasis. A monoclonal antibody for the ADRB3 can specifically bind to the ADRB3, regulate (block or excite) its activity, and be used to treat inflammation, viral infection, atherosclerosis, diabetes, neurodegeneration, autoimmune disease, lalignant tumor, aging disease and the like.

The invention claimed is:

1. A method for treating a malignant tumor, comprising administering an anti-human beta-3 adrenergic receptor (ADRB3) monoclonal antibody to a patient with the malignant tumor, wherein the anti-human ADRB3 monoclonal antibody regulates the functions of an ADRB3 affected by the malignant tumor, wherein the anti-human ADRB3 monoclonal antibody is a monoclonal antibody produced from hybridoma cell line 5D9 deposited with the China Center for Type Culture Collection (CCTCC) under accession number C2016203 on Dec. 12, 2016, wherein the malignant tumor is selected from the group consisting of breast cancer, pancreatic cancer, lung cancer, and melanoma, wherein the step of administering the anti-human ADRB3 monoclonal antibody to the patient comprises administering the anti-human ADRB3 monoclonal antibody at an mice-equivalent dose range of 1-10 mg/kg.

2. The method according to claim 1, wherein the anti-human ADRB3 monoclonal antibody is an anticancer drug.

* * * * *